US010092639B2

(12) United States Patent
Toro

(10) Patent No.: US 10,092,639 B2
(45) Date of Patent: *Oct. 9, 2018

(54) ADAPTATION OF ATTENUATED INFECTIOUS BRONCHITIS VIRUS (IBV) TO EMBRYONIC KIDNEY CELLS AND VACCINE THEREBY PRODUCED

(71) Applicant: Auburn University, Auburn, AL (US)

(72) Inventor: Haroldo E. Toro, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/703,640

(22) Filed: Sep. 13, 2017

(65) Prior Publication Data

US 2018/0008698 A1 Jan. 11, 2018

Related U.S. Application Data

(63) Continuation of application No. 14/887,965, filed on Oct. 20, 2015, now Pat. No. 9,764,025.

(60) Provisional application No. 62/066,135, filed on Oct. 20, 2014.

(51) Int. Cl.
| | |
|---|---|
| *A61K 39/215* | (2006.01) |
| *C12N 7/00* | (2006.01) |
| *C07K 14/165* | (2006.01) |
| *A61K 39/12* | (2006.01) |
| *A61K 39/00* | (2006.01) |

(52) U.S. Cl.
CPC ............ *A61K 39/215* (2013.01); *A61K 39/12* (2013.01); *C07K 14/165* (2013.01); *C12N 7/00* (2013.01); *A61K 2039/5254* (2013.01); *A61K 2039/545* (2013.01); *A61K 2039/552* (2013.01); *A61K 2039/57* (2013.01); *C12N 2770/20034* (2013.01); *C12N 2770/20064* (2013.01); *C12N 2770/20071* (2013.01)

(58) Field of Classification Search
None
See application file for complete search history.

(56) References Cited

U.S. PATENT DOCUMENTS

| | | | |
|---|---|---|---|
| 9,764,025 B2 * | 9/2017 | Toro ..................... | A61K 39/12 |
| 2011/0097353 A1 | 4/2011 | Sellers et al. | |
| 2014/0141043 A1 | 5/2014 | Toro Guzman et al. | |

OTHER PUBLICATIONS

Ammayappan, A., C. Upadhyay, J. Gelb Jr., and V. N. Vakharia. Identification of sequence changes responsible for the attenuation of avian infectious bronchitis virus strain Arkansas DPI Arch. Virol. 154:495-499. 2009.

Armesto, M., D. Cavanagh, and P. Britton. The replicase gene of avian coronavirus infectious bronchitis virus is a determinant of pathogenicity. PLoS One 4:e7384. 2009.

Ballesteros, M. L., C. M. Sa'nchez, and L. Enjuanes. Two amino acid changes at the N-terminus of transmissible gastroenteritis coronavirus spike protein result in the loss of enteric tropism. Virology 227:378-388. 1997.

Baric, R. S., B. Yount, L. Hensley, S. A. Peel, and W. Chen. Episodic evolution mediates interspecies transfer of a murine coronavirus. J. Virol. 71:1946-1955. 1997.

Callison, S. A., D. A. Hilt, T. O. Boynton, B. F. Sample, R. Robison, D. E. Swayne, and M. W. Jackwood. Development and evaluation of a real-time taqman rt-PCR assay for the detection of infectious bronchitis virus from infected chickens. J. Virol. Methods 138:60-65. 2006.

Casais, R., B. Dove, D. Cavanagh, and P. Britton. Recombinant avian infectious bronchitis virus expressing a heterologous spike gene demonstrates that the spike protein is a determinant of cell tropism. J. Virol. 77:9084-9089. 2003.

Cavanagh, D. Severe acute respiratory syndrome vaccine development: experiences of vaccination against avian infectious bronchitis coronavirus. Avian Pathol. 32:567-582. 2003.

Cavanagh, D., and P. J. Davis. Coronavirus IBV: removal of spike glycopolypeptide S1 by urea abolishes infectivity and haemagglutination but not attachment to cells. J. Gen. Virol. 67:1443-1448. 1986.

Cavanagh, D., P. J. Davis, J. H. Darbyshire, and R. W. Peters. Coronavirus IBV: virus retaining spike glycopolypeptide S2 but not S1 is unable to induce virus-neutralizing or haemagglutination-inhibiting antibody, or induce chicken tracheal protection. J. Gen. Virol. 67:1435-1442. 1986.

Cavanagh, D., K. Mawditt, A. Adzhar, R. E. Gough, J. P. Picault, C. J. Naylor, D. Haydon, K. Shaw, and P. Britton. Does IBV change slowly despite the capacity of the spike protein to vary greatly? Adv. Exp. Med. Biol. 440:729-734. 1998.

Domingo, E., E. Baranowski, C. M. Ruiz-Jarabo, A. M. Martin-Hemandez, J. C. Saiz, and C. Escarmis. Quasispecies structure and persistence of RNA viruses. Emerg. Infect. Dis. 4:521-527. 1998.

Enjuanes, L., D. Brian, D. Cavanagh, K. Holmes, M. M. C. Lai, H. Laude, P. Masters, P. Rottier, S. G. Siddell, W. J. M. Spaan, F. Taguchi, and P. Talbot. Coronaviridae. In: Virus taxonomy. Classification and nomenclature of viruses. M. H. V. van Regenmortel, C. M. Fauquet, D. H. L. Bishop, E. B. Carstens, M. K. Estes, S. Lemon, J. Maniloff, M. Mayo, D. J. McGeoch, C. R. Pringle, and R. B. Wickner, eds. Academic Press, New York. pp. 835-849. 2000.

(Continued)

*Primary Examiner* — Shanon A Foley
(74) *Attorney, Agent, or Firm* — Andrus Intellectual Property Law, LLP

(57) ABSTRACT

Disclosed are methods for preparing a vaccine against infection by infectious bronchitis virus (IBV). The methods typically include passing a heterogeneous attenuated population of IBV in chicken embryonic kidney cells, and optionally may include further passaging the heterogeneous attenuated population of IBV in embryonated chicken eggs (ECE) in order to obtain passaged attenuated population of IBV. Also disclosed are passaged attenuated populations of IBV in which the populations display a desired degree of homogeneity. Also disclosed are vaccines comprising the passaged attenuated populations of IBV and methods of vaccination comprising administering the disclosed vaccines.

9 Claims, 7 Drawing Sheets

Specification includes a Sequence Listing.

(56) References Cited

OTHER PUBLICATIONS

Enjuanes, L., W. J. Spaan, E. J. Snijder, and D. Cavanagh. Nidovirales. In: Virus taxonomy. Classification and nomenclature of viruses. M. H. V. van Regenmortel, C. M. Fauquet, D. H. L. Bishop, E. B. Carsten, M. K. Estes, S. M. Lemon, D. J. McGeoch, J. Maniloff, M. A. Mayo, C.R. Pringle, and R. B. Wickner, eds. Academic Press, New York. pp. 827-834. 2000.

Fang, S. G., S. Shen, F. P. Tay, and D. X. Liu. Selection of and recombination between minor variants lead to the adaptation of an avian coronavirus to primate cells. Biochem. Biophys. Res. Comm. 336:417-423. 2005.

Fazakerley, J. K., S. E. Parker, F. Bloom, and M. J. Buchmeier. The V5A13.1 envelope glycoprotein deletion mutant of mouse hepatitis virus type-4 is neuroattenuated by its reduced rate of spread in the central nervous system. Virology 187:178-188.1992.

Gallardo, R. A., V. L. van Santen, and H. Toro. Host intraspatial selection of infectious bronchitis virus populations. Avian Dis. 54:807-813. 2010.

Gallardo, R. A., F. J. Hoerr, W. D. Berry, V. L. van Santen, and H. Toro. Infectious bronchitis virus in testicles and venereal transmission. Avian Dis 55:255-258. 2011.

Gallardo, R. A., V. L. van Santen, and H. Toro. Effects of chicken anemia virus and infectious bursal disease virus-induced immunodeficiency on infectious bronchitis virus replication and genotypic drift. Avian Pathol. 41:451-458. 2012.

Gelb, J., Jr., and M. W. Jackwood. Infectious bronchitis. In: A laboratory manual for the isolation, identification and characterization of avian pathogens. L. Dufour-Zavala, D. E. Swayne, J.R. Glisson, J. E. Pearson, W. M. Reed, M. W. Jackwood, and P. R. Woolcock, eds. American Association of Avian Pathologists, Athens, GA. pp. 146-149. 2008.

Ghetas, A. M., G. E. Thaxton, C. Breedlove, V. L. v. Santen, and H. Toro. Effects of Adaptation of Infectious Bronchitis Virus Arkansas Attenuated Vaccine to Embryonic Kidney Cells. Avian Dis. 59:106-113. 2015.

Hingley, S. T., J. L. Gombold, E. Lavi, and S. R. Weiss. MHV-A59 fusion mutants are attenuated and display altered hepatotropism. Virology 200:1-10. 1994.

International Search Report and Written Opinion for PCT/US2015/056416 dated Jan. 29, 2016.

International Preliminary Report on Patentability for PCT/US2015/056416 dated May 4, 2017.

Jackwood, M. W., D. A. Hilt, C. W. Lee, H. M. Kwon, S.A. Callison, K. M. Moore, H. Moscoso, H. Sellers, and S. Thayer. Data from 11 years of molecular typing infectious bronchitis virus field isolates. Avian Dis. 49:614-618. 2005.

Jackwood, M. W., D. A. Hilt, A. W. McCall, C. N. Polizzi, E. T. McKinley, and S. M. Williams. Infectious bronchitis virus field vaccination coverage and persistence of Arkansas-type viruses in commercial broilers. Avian Dis. 53:175-183. 2009.

Koch, G., L. Hartog, A. Kant, and D. J. van Roozelaar. Antigenic domains on the peplomer protein of avian infectious bronchitis virus: correlation with biological functions. J. Gen. Virol. 71:1929-1935. 1990.

Kusters, J. G., E. J. Jager, J. A. Lenstra, G. Koch, W. P. Posthumus, R. H. Meloen, and B. A. van der Zeijst. Analysis of an immunodominant region of infectious bronchitis virus. J. Immunol. 143:2692-2698. 1989.

Kusters, J. G., H. G. Niesters, N. M. Bleumink-Pluym, F. G. Davelaar, M. C. Horzinek, and B. A. van der Zeijst. Molecular epidemiology of infectious bronchitis virus in The Netherlands. J. Gen. Virol. 68:343-352. 1987.

Kwon, H. M., M. W. Jackwood, and J. Gelb Jr. Differentiation of infectious bronchitis virus serotypes using polymerase chain reaction and restriction fragment length polymorphism analysis. Avian Dis. 37:194-202. 1993.

Lai M. M. C., and K. V. Holmes. Coronaviridae: the viruses and their replication. In: Fundamental virology. D. M. Knipe and P. M. Howley, eds. Lippincott Williams and Wilkins, Philadelphia. pp. 641-663. 2001.

Leparc-Goffart, I., S. T. Hingley, M. M. Chua, X. Jiang, E. Lavi, and S. R. Weiss. Altered pathogenesis of a mutant of the murine coronavirus MHV-A59 is associated with a Q159L amino acid substitution in the spike protein. Virology 269:1-10. 1997.

Li, W., C. Zhang, J. Sui, J. H. Kuhn, M. J. Moore, S. Luo, S. K. Wong, I. C. Huang, K. Xu, N. Vasilieva, A. Murakami, Y. He, W. A. Marasco, Y. Guan, H. Choe, and M. Farzan. Receptor and viral determinants of SARS-coronavirus adaptation to human ACE2. EMBO J. 24:1634-1643. 2005.

McKinley, E. T., D. A. Hilt, and M. W. Jackwood. Avian coronavirus infectious bronchitis attenuated live vaccines undergo selection of subpopulations and mutations following vaccination. Vaccine 26:1274-1284. 2008.

Ndegwa, E. N., K. S. Joiner, H. Toro, F. W. van Ginkel, and V. L. van Santen. The proportion of specific viral subpopulations in attenuated ArkDPI infectious bronchitis vaccines influences vaccination outcome. Avian Dis. 56:642-653. 2012.

Ndegwa, E. N., H. Toro, and V. van Santen. Comparison of vaccine subpopulation selection, viral loads, vaccine virus persistence in trachea and cloaca, and mucosal antibody responses after vaccination with two different Arkansas Delmarva Poultry Industry-derived infectious bronchitis virus vaccines Avian Dis 58:102-110. 2014.

Nix, W. A., D. S. Troeber, B. F. Kingham, C. L. Keeler, Jr., and J. Gelb, Jr. Emergence of subtype strains of the Arkansas serotype of infectious bronchitis virus in Delmarva broiler chickens. Avian Dis. 44:568-581. 2000.

Ontiveros, E., T. S. Kim, T. M. Gallagher, and S. Perlman. Enhanced virulence mediated by the murine coronavirus, mouse hepatitis virus strain JHM, is associated with a glycine at residue 310 of the spike glycoprotein. J. Virol. 77:10260-10269. 2003.

Phillips, J. E., M. W. Jackwood, E. T. McKinley, S. W. Thor, D. A. Hilt, N. D. Acevedol, S. M. Williams, J. C. Kissinger, A. H. Paterson, J. S. Robertson, and C. Lemke. Changes in nonstructural protein 3 are associated with attenuation in avian coronavirus infectious bronchitis virus. Virus Genes 44:63-74. 2012.

Schat et al., Cell-culture methods. In: A laboratory manual for the isolation and identification of avian pathogens. D. E. Swayne, J. Glisson, M. W. Jackwood, J. E. Pearson, and W. M. Reed, eds. American Association of Avian Pathologists, Inc., Kenneth Square, PA. pp. 223-234. 1998.

Sperry, S. M., L. Kazi, R. L. Graham, R. S. Baric, S. R. Weiss, and M. R. Denison. Single-amino-acid substitutions in open reading frame (ORF) 1b-nsp14 and ORF 2a proteins of the coronavirus mouse hepatitis virus are attenuating in mice. J. Virol. 79:3391-3400. 2005.

Toro, H., J. W. Jackwood, and V. L. van Santen. Genetic diversity and selection regulates evolution of infectious bronchitis virus. Avian Dis. 56:449-455. 2012.

Toro, H., P. Lavaud, P. Vallejos, and A. Ferreira. Transfer of IgG from serum to lachrimal fluid in chickens. Avian Dis. 37:60-66. 1993.

Toro, H., D. Pennington, R. A. Gallardo, V. L. van Santen, F. W. van Ginkel, J. F. Zhang, and K. S. Joiner. Infectious bronchitis virus subpopulations in vaccinated chickens after challenge. Avian Dis. 56:501-508. 2012.

Toro, H., V. L. van Santen, L. Li, S. B. Lockaby, E. van Santen, and F. J. Hoerr. Epidemiological and experimental evidence for immunodeficiency affecting avian infectious bronchitis. Avian Pathol. 35:1-10. 2006.

Toro, H., J. F. Zhang, R. A. Gallardo, V. L. v. Santen, F. W. v. Ginkel, K. S. Joiner, and C. Breedlove. S1 of Distinct IBV Population Expressed from Recombinant Adenovirus Confers Protection Against Challenge. Avian Dis 58:211-215.2014.

van Ginkel, F. W., V. L. van Santen, S. L Gulley, and H. Toro. Infectious bronchitis virus in the chicken Harderian gland and lachrymal fluid: viral load, infectivity, immune cell responses, and effects of viral immunodeficiency. Avian Dis. 52:608-617. 2008.

Van Santen et al., ArkDPI-derived IBV vaccines and their subpopulations selected in chickens: differences outside the S gene VII.

(56) References Cited

OTHER PUBLICATIONS

International Symposium Avian Corona- and Pneumoviruses and Complicating Pathogens. pp. 94

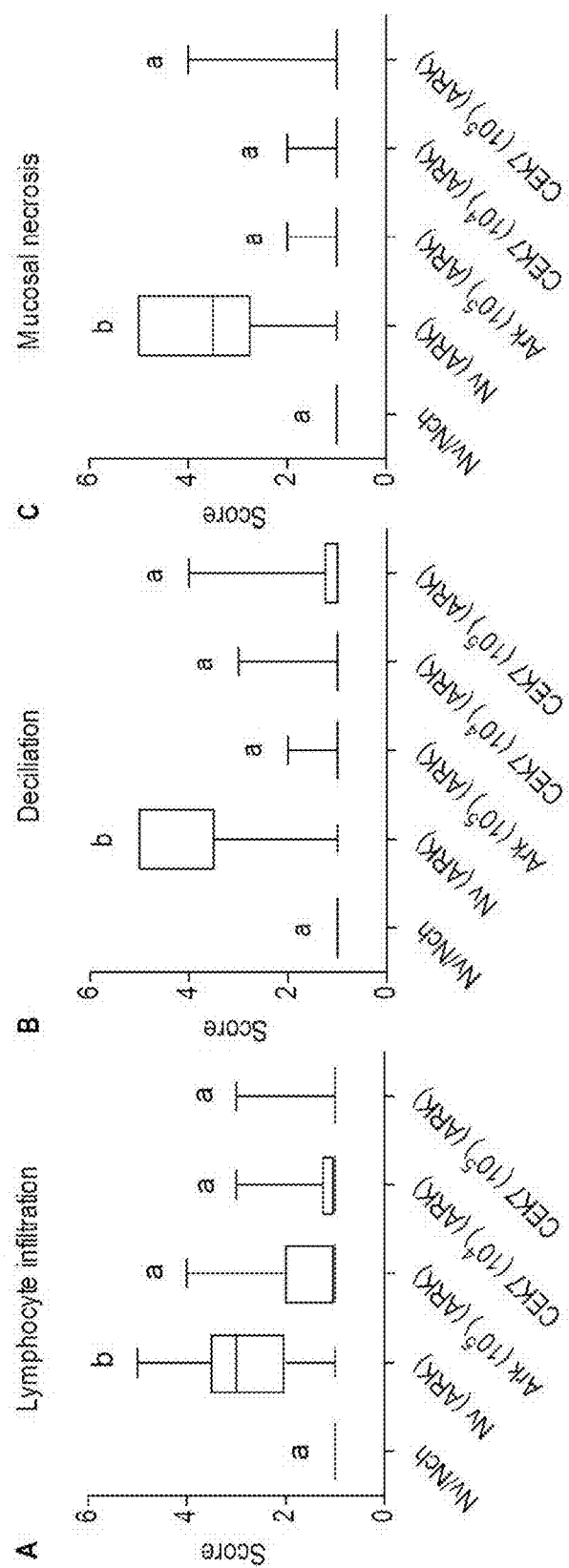

SEQUENCE LISTING

<160> NUMBER OF SEQ ID NOS: 6

<210> SEQ ID NO 1
<211> LENGTH: 27636
<212> TYPE: DNA
<213> ORGANISM: Infectious Bronchitis Virus

<400> SEQUENCE: 1

```
acttaagata gatattaata tatatctatt gcactagcct tgcgctagat ttccaactta      60
acaaaacgga cttaaatacc tacagctggt ccccataggt gttccattgc agtgcacttt     120
agtgccctgg atggcacctg ccacctgtc aggttttgt tgttaaaata tcattgttgc       180
tggtatcact gcttgttttg ccgtgtctca ctttatacat ccgttgcttg ggctacctag     240
tatccagcgt cctacgggcg ccgtggtcgg ttcgagtgcg aaggacctct ggttcatcta     300
gcggtaggcg ggtgtgtgga agtagcgctt cagacgtact ggttctgttg cgtgaaacgc     360
ggggtcacct cccccacat acctctaagg gcttttgagc ctagcgttgg gctacgttct      420
cgcacaaggt cggctatacg acgtttgtag ggggtagtgc caaacaaccc ctgaggtgac     480
aggttctggt ggtgtttagt gagcagacat acaatagaca gtgacaacat ggcttcaagc    540
ctaaaacagg gagtatctcc caaccaagg gatgtcattc ttgtttccaa agacattccc     600
gaacaactct gtgacgcttt attttctac acgtcacata accctaagga ttacgctgat    660
gcttttgcat ttaggcaaaa gtttgaccgt aatctgcaga ctgggaagca gttcaaattt   720
gaaactgttt gtggtctctt cctattgaag ggagttgaca aaataacacc tggcgtccca   780
gcaaaagttt taaaagccac ttctaagttg gcagatttag aagacatctt tggtgtctct   840
ccttttgcac ggaagtaccg tgaattgttg aaaacagcat gccagtggtc tcttactgta   900
gaaacactgg atgctcgtgc acaaacgctt gacgaaattt ttgactctac tgaaatactt  960
tggcttcagg tggctgcaaa aattcaagtt tcagctatgg caatgcgcag gcttgttgga  1020
gaagtaactg caaaagtcat ggaagctctt ggctcaaatt tgagtgttct ctttcaaatt  1080
gttaaacaac aaatagccag aatctttcaa aaggcactgg ctattttga aaatgtgagt  1140 gaattaccac agcgtattgc agcacttaag atggccttg ccaagtgtgc caagtcaatt  1200
actgttgtgg ttgtggaaag aactctagtt gttagagagt tcgcaggaac ttgtcttgca  1260
agcatcaatg gtgctgttgc aaaattcttt gaagaacttc caaatggctt catgggttct  1320
aaaatcttca caacattggc cttctttaaa gaagcagctg tgaaaattgt ggaaaatata  1380
ccaaatgcac caagaggtac tagaggtttt gaagtcgttg gtaacgccaa gggaacgcaa  1440
gttgttgtgc gtggcatgcg aaatgattta actctgctcg accaaaaagc tgacattcct  1500
gttgagaaag aaggttggtc tgcaattctt gaaggacatc tgtgttatgt ctttaagagt  1560
ggtgatcgtt tttatgcggc acctctttct gggaattttg cattgcatga tgtgcattgt  1620
tgtgagcgtg ttgtctgtct gtctgatggt gtaacaccag agataaatga tggactcatt  1680
ctagcagcaa tctattcatc ttttagtgtc tcagaactcg tggcagcact taaaagggt  1740 gaaccattca agttcttggg tcataaattt gtgtatgcga aggatgcagc agtctctttc  1800
actcttgcaa aagcagccac tattgcagat gtactgaagc tgtttcaatc agctcgtgtg  1860
caaacggaag atgtgtggtc tgcatttact gaaaagtctt ttaatttctg gaaactcgca  1920 tatggaaag tgcgtaatct tgaagaagtt gtgaagactc atttttgtaa agctcaaatg  1980
tcaattatca ttctagcagc agtgcttggc gaaggcattt ggcatcttgt tcacaggtc   2040 atctataaag taggtggtct ttttactaga gtcgttgact tttgtgaaaa acactggaag  2100
```

```
ggtttctgtg cacaacttaa aaaggctaag ctcgttgtca cagaaactct ttgtgttctt    2160
aagggagtgg cacagcattg ttttcaacta ttgctggatg caatacattc tttgtatatg    2220
agttttaaga agtgtgcact tggtagaatt catggagact tactcttctg gaaaggggt     2280 gtacacaaaa ttgttcaaga tggcgatgaa gtttggtttg acgccattga tagtattgat    2340
gttgaagatc tgggtgttgt ccaagaaaaa cccatagatt ttgaggtttg tgaagacgta    2400
acacttccag aaaatcaacc tggtcatatg gttcaaatcg aggatgacgg aaagaactat    2460
atgttcttcc gcttcaaaag ggatgagaac atctactata caccaatgtc tcaacttggt    2520
gtaattaatg tagtttgcaa agcaggcggt aaaaccgtta cctttggaga caccattgtg    2580
aaagaaatac cgccacctga tgttgtgcct attaaggtta gcatagagtg ttgtggtgaa    2640
ccatggaata caatcttcaa gaaagcttat aaagagccca ttgaagttga aactgacctc    2700
acagtagaac aattgctctc tgtgatctat gagaaaatgt gcgacgacct caaattgttt    2760
ccagaggcac cagagccacc gccatttgag aatgtcgcac ttgttgataa aaacggtaaa    2820
gacttggatt gcataaaatc atgccatctt atctaccgtg attatgagag tgatgatgac    2880
atcgaggaag aagatgctga ggagtgtgat actgatttag aatgtgaaga agaggatgag    2940
gatactaaag tgttggctct tatacaagac cctgcaagta ataaatacc  tcttcctctt    3000 gatgatgatt atagcgtctt taatggatgt attgtacata aggacgctct tgacgtcgta    3060
aatctaccat ctggtgaaga aacctttgtt gtcaacaact gctttgaggg agctgtaaaa    3120
ccactgcctc agaaagttgt tgatgttcta ggtgactggg gtgaggctgt tgatgcgcaa    3180
gagcaaattg cacaaactac ttcagaggaa acccctatca gtagtttgga ggcaactatt    3240
gagcaagttt tgttgagga  acagaaaata atttctgttg ttgaagaaga acagcaggtg    3300
gcggtctaca cacctgcaga cctacaagtt gttgaagaaa caccagatga gtttattctt    3360
actgctgatg tttccacaga agaaattgtg cctcatgaag aaaaggagtc acagattgaa    3420
caggagccta ttcaagttgt taaatcacaa cgtgaaaaga aggctaaaaa gttcaaggtt    3480
aaatctacta catgtgagaa acccaaattt ttggagtaca caacatgtgt gggtgaccta    3540
acggtagtga ttgccaaagc attggatgag tttaaagagt tctgcattgt aaatgctgct    3600
aatgagcata tgtctcacgg tggcggcgtt gctaaggcaa ttgcggactt ttgtggacct    3660
gattttgtgg agtattgtga ggactatgtt aagaaacatg gcctcaaca  aagacttgtc    3720 acaccttcat ttgtcaaagg cattcaatgt gtgaacaatg ttgtaggacc tcgccatgga    3780
gacagtaact tgcatgataa gcttgttgct gcttacaaga atgttcttgt agatggtgtt    3840
gtcaattatg ttgtgccagt cctctcatca ggaattttg  tgttgatttt aagatgtct    3900 atagacgcta tgcgcaaggc ttttgaaggt tgcgacatac gcgttcttct tttctccttg    3960
tctcaagaac acatcgatta tttcgatgtt acttgtaaac agaagacaat ttatcttaca    4020
gaggacggtg ttaaataccg ctctgctact gtgaaaccag gtgactcttt gagtcaatt     4080 ggaccggttt ttgctagaaa caagacagtc tttacagcag acgatgttga ggataaagaa    4140
attctcttca ttcctactac tgacaagact gtccttgaat attatgggtt ggatgcgcaa    4200
aagtatgtaa tatacttgca aactcttgca cagaagtgga atgtccaata tagggacaat    4260
tttgttatac ttgagtggcg tgatggaaat tgctggatta atgcagcagt agtgctcctt    4320
caagctgcta agattaggtt taaaggtttt cttgcagaag catgggcaca acttttgggt    4380
ggagacccaa ctgattttgt agcctggtgc tatgcaagtt gcaatgctaa tgttggtgag    4440
```

```
ttttcagatg ctaattggct tcttgctaat ttggcagaat actttgatgc tgattacacg    4500
aatgcattcc ttaagaggcg tgtgtcatgt aactgtgggg ttaagaattg tgaagttaga    4560
ggccttgaag cttgtattca accagtaaag gcacccaatc ttcttcattt taagactcag    4620
tacacaaatt gtacagtgtg tgatgcaaat agtgtggatg aggtggtaga agcctcacta    4680
ccatatctgt tgctccttgc tactgatggt cctactacag tggattgtga tgaaaatgct    4740
gtagggaatg ttgttttcat tggctctact aatagtggcc attgttacac gcaagccatt    4800
ggtaaggctt ttgataatct tgctaaggat agaaaatttt caaagaattc gccatacatt    4860
acagcaatgt atacgcgctt ctctcttaag agtgaaagct ctctgtctgt tgttaaacag    4920
agtaagagta aaactaaagt agtaaaagaa gatgttgcca accttgctac tagttctaaa    4980
gccagttttg atgatcttac tgactttgaa cattggtatg atagtaacat ctatgaaagt    5040
cttaaagttc aggaaatacc tgtgaatttg gatgagtatg tgtcatttac aacgaaagaa    5100
gatactaagt tgccactgac acttaaagtt agaggtatca atcagttgtt gactttatt    5160 tcaagagacg gtttctctta taagttaaca cctgacattg aagaaaattc aaaagcgcca    5220
gtctactacc cagtcttaga ctctattagt cttaaggcaa tatgggtaga cggcagtgct    5280
aattttgttg ttggtcatcc aaactactat agtaagtctc ttcgcattcc tacttttggg    5340
gaaaatgcag agagctttgt taagataggt gacaaagttg atggtgtaac tatgggcctt    5400
tggcgtgcag aacatcttaa caaacctaat cttgaaagaa ttttcaacat tgctaagaaa    5460
gctattgttg gatccagtgt tgttactaca caatgtagta aattaattag taaagcagct    5520
acattcattg ctgataaagt aggtgggggt gtagttcgta atattacaga tagaattaag    5580
ggtctttgtg gatttacacg tgggcatttt gaaagaaaat tgtctccaca attcataaaa    5640
acacttatat tcttcttctt ttactttgta aaggctagtg ctaagagtgt tgccactagt    5700
tataagcgtg tgttatgtaa ggtggttttt accacgctat ttatattatg gtttatgtac    5760
acaagtaaac cagtaacttt tactggaaca cgtgtgctag acttcttatt tgagggttct    5820
ttatgtggtc cctataatga ctatggtaaa gactcatttg acgtactacg ctattgtgga    5880
gatgatttta cttgtcgtgt atgtttacat gataaagatt cacttcattt gtataagcat    5940
gcttatagcg tagaacaggt ttataaagat gcagcttctg gcattagttt taattggaat    6000
tggctttatt tggtctttct aatatattt gttaaaccag tagcaggttt cgttattatt    6060
tgctattgtg ttaagtactt ggtattgagt tcaactgtgt tgcaaactgg tgtaggtttt    6120
atggactggt ttattcaaac agtttttact cactttaatt ttatgggtgc aggtttctat    6180
ttctggctct tctataaatt gtacatacag gttcatcata tactgtattg taaggatata    6240
acatgtgaag tgtgtaagag agttcacgc agtaacaggc atgaggttag tgttgttgtt    6300
ggtggacgca agcaaattgt gcacgtgtac actaactctg gttacaactt tgtaagaga    6360 cataattggt attgtaggaa ttgtgatgta tatggtcacc aaaacacatt tatgtctcct    6420
gaagttgctg gcgagctttc tgaaaagctt aaacgccatg ttaaacctac agcacatgct    6480
taccacgttg tggatgaggc ttgcgtagtt gatgattttg ttaacttaaa atacaaagct    6540
gcaactcctg gtaaggatgg tgcacctcct gcagttaaat gtttcagtgt tacagatttc    6600
ttgaagaaag ctgttttttct taaggatgcg ctgaaatgtg aacaaatatc taatgatggt    6660
tttatagtgt gtaatacgca gagtgcgcat gctttagagg aagcaaagaa tgcagccatc    6720
tattatgcgc aatacctgtg taaacctata cttatactcg accaggcact ctaccagaat    6780
ttaatagtgg aacctgtatc gaagagcgtt gtcaacaaag tgtgtgacat tttgtctagg    6840
```

```
ataatttctg tagatactgc atctttggat tataaagcag gtacaattcg tgatgccttg    6900
ctgtctgtta ctaaagatga agaagctgta gatatggcta tcttctgtca taatcatgaa    6960
gttgaatata caggtgatgg ttttactaat gttataccgt catatggtat agacactgat    7020
aaattaacac ctcgtgatag agggttttg ataaatgcag atgcttctgt tgctaactta     7080
agagttaaaa atgctccgcc ggtagtatgg aagttctctg atcttattaa gttgtctgac    7140
agttgtctta aatatttaat ctcagcaact gtcaagtcag ggtctcgttt ctttataaca    7200
agatctggtg ctaaacaaat ttttcttgt agtactcaga aattgttggt agagaaaaag     7260
gctggtggtg tcgttagtgg tacctttaat tggtttaaga gttgttgtaa atggctcttg    7320
atcttctatg tgcttttac attgtgttgt ttggttgtt atcatatgga gacgaataaa      7380
agttttgttc atcctatgta tgatgttaac tctacaatgc atgttgaagg ctttaaggtt    7440
atagataaag gtgttattag agacattgta ccagaggatg cttgtttctc taataagttt    7500
gctaactttg atgcattttg gggtaaacca tatgtaata gtagagactg tccaattgtt     7560
acagcagtca tagatggcgc tggaacaata gtagctggtg ttcctggttt tgtagactgg    7620
gttcttgatg tgttatgtt tgtacacatg acacaaacag aaagaaaacc ctggtacatt     7680
cccatgtggt ttaacagaga aattgttggt tacactcagg attcaattat tactgaaggt    7740
agttttata catctatagc tttgttttca gctaggtgtt tatatttaac agccagcaat     7800
acaccacaat tgtattgttt taatggtcat aatgatgctc ctggagcctt accatttagc    7860
agtatcactt cacacagggt ctacttccaa ccaaatggtg ttaggcttat aattcctcaa    7920
caaataatgc acacacccta cgtagtaaag tttttatcag acagctattg tagaggtagt    7980
gtatgtgagt atactaaacc gggttattgt gtttcactaa attcccaatg gttttattt     8040
aatgacgaat acacaagtaa accaggagta ttctgtggtt ctactgttag agaacttatg    8100
tttaatatgg ttagtacatt ttttactggt gtcaaccta atatttatat gcagctggcg     8160
actatgttct taatactagt tgttgttgtg ttaattttg caatggttat aaagtttcaa     8220
tgtgttttta agcttatgc aaccattgtg tttataataa tgctagtttg ggttgttaat    8280
gcatttattt tgtgtgtaca tagttataat agtgttgtgg ctgttatact actagtaatc    8340
tattgttatg catcattggt tacaagtcgt aatactgcta taataatgca ttgttggctt    8400
gtgtttacct ttggtttaat tgtacccata tggttggcgt gttgctacct ggcatttgtt    8460
ttatatatgt acacaccatt gcttttctgg tgttacggta ctactaaaaa tactcgtaag    8520
ttgtatgatg gcaacgagtt tgttggtaat tatgaccttg ctgcgaagag cacttttgtt    8580
attcgtggta ctgaatttgt taagcttacg aatgagatag gtgataaatt tgaatcctat    8640
ctttctgcgt atgctagact taaatattat tcaggcactg gcagtgagca agattacttg    8700
caagcctgtc gtgcatggtt agcttatgct ttggaccaat atagaaatag tggtgtggaa    8760
attgtgtata ctccaccacg ttactctatt ggtgttagta gattacaggc tggttttaag    8820
aaactagttt ttcctagtag tgctgttgaa aagtgcattg ttagtgtctc ttatagaggt    8880
aataatctta atggactatg gctaggtgat actatctact gtccgcgaca tgttctaggc    8940
aagttttcag gtgatcaatg gagtgatgta cttaatcttg ctaataatca tgagtttgag    9000
gttgcaactc aaaatggtgt tactttgaat gttgttagta ggcggttgag aggcgcagtt    9060
ttaattttac aaactgctgt cgccaatgct gacactccta agtataagtt tgttaaagct    9120
aattgtggtg atagtttcac tatagcttgt tcttatggtg gtacagttgt gggactctac    9180
```

```
cctgttacta tgcgttctaa tggtactatt agagcttctt tccttgcagg agcttgtggc    9240
tcagttggtt ttaatataga gaagggtgta gttaatttct tttatatgca ccatcttgag    9300
ttacctaatg cattacacac tggaactgac ctaatgggtg atttctatgg tggttatgtg    9360
gacgaagagg ttgcacaaag ggtgccacca gataatttag ttactaataa tattgtagca    9420
tggctttatg ccgcaattat tagtgttaag gagagtagtt tctcactgcc taaatggttg    9480
gagagtacta ctgtcagtgt tgaagactat aataagtggg ctggtgataa tggttttaca    9540 ccatttttcta ctagtactgc tattactaaa ttaagtgcta taacgggagt agatgtttgt    9600
aaactccttc gcactattat ggtaaaaagt agtcaatggg gtagtgatcc cattttagga    9660
caatataatt ttgaagatga attgacacca gagtctgttt tcaaccagat aggtggtgtt    9720
aggttacagt catctattgt aagaagagtc acatcttggt tttggagtag atgtgtgtta    9780
gcttgcttct tatttgtgtt gtgtgctatt gtcttgttta cggcagtacc acttaaatac    9840
tatgtacatg cagctgttat tttgttaaca gctgtacttt ttatttcttt tactgttaaa    9900
catgttatgg catatatgga tacttttctg ttgcctacat tgattacagt tattattgga    9960
gtttgtgctg aagtcccttt catatacaat actctaatta gtcaagttgt tattttctta   10020
agccaatggt atgatcctgt agtctttgat actatggtac catggatgtt attgccatta   10080
gtgttgtaca ctgctttaa gtgtgtacaa ggttgctata tgaattcttt caatacttct   10140
ttgttaatgc tgtatcagtt tatgaagtta ggttttgtta tttacacctc ttctaacact   10200
cttactgcat atacagaagg taattgggag ttatttttttg agttagttca cactactgtg   10260
ttggctaatg ttagtagcaa ttctttaatt ggtctacttg tgtttaagtg tgctaagtgg   10320
atgttgtatt attgcaatgc aacatacttt aataattatg tgttaatggc agtcatggtt   10380
aatggcatag gctggctttg tacttgttac tttggattgt attggtgggt taataaggtt   10440
tttggtttaa ctttaggtaa atacaatttt aaagtctcag tagatcaata taggtatatg   10500
tgtttgcata agataaatcc acctaaaact gtgtgggaag tcttttcgac aaatatactt   10560
atacaaggaa ttggtggtga tcgtgtgttg cctattgcta cagttcaatc taaattgagt   10620
gatgtaaagt gtacaactgt tgtttaatg cagcttttga ctaagcttaa tgttgaagca   10680
aattcaaaaa tgcatgctta tcttgttgag ttacacaata aaatccttgc atctgatgat   10740
gttgagagag catggataa tttgttgggt atgcttatta cactgttttg tatagattct   10800
actattgatt tgagtgagta ttgtgatgat atacttaaga ggtcaactgt cttacagtca   10860
gttactcaag agttctcaca catacccctct tatgctgaat atgaaagagc taagaatctt   10920
tatgaaaagg ttttaactga ttctaaaaat ggtggtgtaa cacagcaaga gcttgctgca   10980
tatcgtaaag ctgccaatat tgcaaagtca gttttttgata gagacttggc tgttcaaaag   11040
aagttagaca gcatggcaga acgtgctatg acaacaatgt ataaagaggc gcgtgtaact   11100
gatagacgag caaaattagt ttcatcacta catgcgttac tcttttcaat gcttaagaaa   11160
atagattctg aaaagcttaa tgtcttattt gatcaggcta gtagcggtgt tgtacctcta   11220
gctactgttc caattgtttg tagtaataag cttacccttg taataccaga tccagaaact   11280
tgggtcaagt gtgtggaagg tatgcatgtt acatattcaa cagttgtttg gaatatagac   11340
actgttattg atgctgatgg tacagagtta catccaactt ctataggtag tggattgaca   11400
tactgtataa gtggtgacaa tatagcatgg cctttaaagg tcaacttgac taggaatggg   11460
cataacaagg ttgatgctgc tttgcagaat aatgagctta gcctcatgg tgtaaaaaca   11520 aaggcttgcg tagcaggtgt agatcaagca cattgtagcg tagagtctaa atgttattat   11580
```

```
acaaatatta gtggcaattc agttgtagct gctattactt cttcaaatcc aaatctgaaa    11640
gtagcttcgt ttttgaacga ggcaggcaat cagatttatg tagacttaga cccaccatgt    11700
aaatttggca tgaaggtggg tgacaaggtt gaggttgttt acttgtattt tataaagaat    11760
acaaggtcga ttgttagggg tatggtactt ggtgctatat ctaatgttgt tgtcttacag    11820
tctaaagggc atgaaacaga ggaagtggag gctgttggca ttctttcact ttgctcattt    11880
gcagtagatc ccgctgatac atattgtaaa tatgtggcgg caggtaatca acctttaggt    11940
aactgtgtta aaatgttgac agtacataat ggtagtggct ttgctataac atcaaagcca    12000
agtccaactc ctgatcagga ttcttatgga ggagcttctg tgtgtctcta ttgtagagca    12060
cacatagcac acccaggagg tgcaggaaat ttagatggac gttgtctatt taaaggttct    12120
tttgtgcaaa tacctactac ggagaaagac cccgtcggat tctgtctacg taataaggtt    12180
tgtactgttt gtcagtgttg gattggttat ggctgtcagt gcgatgcact tagacaacct    12240
aaaccttttg ttcagtcagt tgctggtgca tctgatttg ataagaatta tttaaacggg    12300
tacggggtag cagtgaggct cggctgatac cccttgctag tggatgtgat cctgatgttg    12360
taaagcgagc ctttgatgtt tgtaataagg aatcatctgg tatgtttcga aactttaagc    12420
gtaactgtgc gagattccaa gaagtacgtg atactgaaga tggaaatctt gagtattgtg    12480
attcgtactt tgtggttaaa caaaccactc ctagtaatta tgaacatgag cggtcttgtc    12540
acgaagactt aaagtcagac gtaatagccg atcatgattt ctttgtgttc aataagaaca    12600
tttataatat tagtaggcag aggcttacta aatatactat gatggacttt tgctacgctt    12660
tgaggcattt tgacccaaag gactgcgaag ttcttaaaga aatacttgtc acttatggtt    12720
gtatagaaga ttatcaccct aagtggtttg aagagaataa ggattggtac gacccaatag    12780
aaaacccaaa atattatgcc atgttggcta aaatggggcc tattgtacga cgtgctctat    12840
tgaatgctat tgagttcgga aaccttatgg ttgaaaaagg ttatgttggt gttgttacac    12900
ttgataacca agatcttaac ggtaaatttt atgattttgg tgattttcaa aaaacagcac    12960
ctggtgctgg tgttcctgtt tttgatacat attattctta catgatgccc atcatagcca    13020
tgacggatgc tttggcacct gaaaggtatt ttgaatatga tgtgcataag ggttataagt    13080
cttatgatct cctcaagtat gattatactg aggagaaaca agagttgttt cagaaatact    13140
ttaagtattg ggaccaggag taccatccta actgccgtga ctgtattgat gacaggtgtt    13200
tgatacattg tgcaaacttc aacatcttgt tttctacact gataccgcag acttctttg    13260 gtaatttgtg tagaaaggtg tttgttgatg gtgtaccttt tatagctact tgtggctatc    13320
attccaaaga acttggtgtt attatgaatc aagataacac tatgtcgttc tcaaaaatgg    13380
gtttaagtca actcatgcag tttgttggag accctgcctt gttagtggga acatccaata    13440
atttaatcga tcttagaacg tcttgtttta gtgtttgtgc attggcgtct ggtattactc    13500
atcaaacggt aaaccaggt cactttaaca aggatttcta tgattttgca gagaaggctg    13560
gtatgtttaa ggaaggttct tctataccac ttaaacattt cttctaccct cagactggta    13620
atgctgctat aaacgattat gattattatc gttataacag gcctaccatg ttcgatatac    13680
gtcaacttct attttgttta gaagtgactt ctaaatactt tgaatgctat gaaggcggct    13740
gtataccagc aagccaagtt gtagttaata atctagataa gagcgcaggc tacccattta    13800
ataagtttgg aaaagcccgt ctctattatg aaatgagtct agaggaacag gaccaactct    13860
ttgagagtac aaagaagaat gtcctgccca ctataactca aatgaattta aaatatgcca    13920
```

```
tatccgcgaa aaatagagcg cgtacagtgg caggtgtgtc tatcctttct actatgacta    13980
ataggcagtt tcatcagaag attcttaagt ctatagtcaa cactagaaac gctcctgtag    14040
ttattggaac aaccaagttt tatggcggtt gggacaatat gttgagaaac cttattcagg    14100
gtgttgaaga tccgattctt atgggttggg actatccaaa gtgtgataga gcaatgccaa    14160
atttgctacg tatagcagca tctttggtac ttgctcggaa acacactaac tgttgtactt    14220
ggtctgagcg catttatagg ttgtataatg aatgcgctca ggttttatca gaaactgtcc    14280
tagctacagg tggtatttat gtaaaacctg gtggtactag cagtggtgat gctactactg    14340
cttatgcaaa cagtgttttt aatataaatac aagctcatc tgctaatgtt gcgcgtcttt    14400
tgagtgttat aacgcgtgat attgtttatg atgacattaa gagcctgcag tatgagttgt    14460
accagcaggt ttataggcga gttaattttg acccagcctt tgtagaaaag ttttattctt    14520
acttatgtaa gaatttctct ttgatgatct tgtccgacga cggtgttgtt tgttataaca    14580
atacactagc caaacaaggt cttgtagcag atatttctgg ttttagagaa gttctctact    14640
accaaaataa tgtctttatg tctgacgcta aatgttgggt ggaaccagat ttagaaaaag    14700
gccctcatga attttgttca cagcatacaa tgctagtgga agtggatggt gagcctaaat    14760
acttgccata tccagaccct tcacgcattt taggtgcatg tgttttttgta gatgatgtgg    14820 ataagacgga acctgtggct gttatggagc gttatatagc tctagccata gacgcttacc    14880
cgctagtaca tcatgaaaat gaggagtaca agaaggtgtt ctttgtgctt ctttcataca    14940
tcagaaaact ctatcaagag ctttctcaga atatgcttat ggactactct tttgtaatgg    15000
atatagacaa gggtagtaaa tttttgggaac aggagttcta tgagaatatg tatagagctc    15060
ctacgacttt acaatcttgt ggtgtctgtg tagtttgtaa tagtcaaact atactgcgct    15120
gtggtaattg tattcgcaaa ccattttgt gttgtaaatg ttgctatgac catgtcatgc    15180
atacagacca caaaatgtt ttgtctataa atccatacat ttgctcacag cccggttgtg    15240
gcgaggcaga tgttactaaa ttgtacctcg gaggtatgtc atacttctgt ggtaatcata    15300
aaccaaaatt gtcaataccg ttggtatcta atggtactgt ttttggaatt tacagggcta    15360
attgtgctgg tagcgaaagt gttgatgatt taatcaact agctactact aattggtcta    15420
ctgtggaacc ttatatttg gcaaatcgct gtagtgactc attgagacgc ttcgctgcgg    15480
aaacagtaaa agctacagag gagttgcata gcagcagtt tgctagtgct gaagtgcgag    15540
aagttctctc agatcgtgag ttgattctat catgggagcc aggtaaaact aggcctccat    15600
tgaataggaa ttatgtcttt acaggctatc actttacaag aactagtaag gtgcagcttg    15660
gtgattttac atttgaaaaa ggtgaaggta agatgttgt ctattatagg gcaacgtcca    15720
ctgctaaatt gtctgttgga gacatttttg ttttaactc acgcaatgtt gtttctcttg    15780
tagcaccaac attgtgtcca caacagacct tttctaggtt tgtaaactta agacctaatg    15840
taatggtacc agaatgtttt gtgaacaaca ttccactcta ccattagta ggtaagcaga    15900 agcgtactac agtacaaggt cccccaggca gtggtaaatc acattttgct ataggccttg    15960
cagcatactt tagtaacgct cgtgttgtct ttactgcatg ttctcatgca gctgttgatg    16020
ctttatgtga aaaagcttt aagttttaaaa agttgatga ttgcactagg atagtacctc    16080
aaagaactac tatcgactgc ttttcaaagt ttaaagctaa tgacacaggc aaaaagtata    16140 ttttagtac tataaatgcc ttgccagaag ttagttgtga cattctttg gttgacgagg    16200 ttagtatgtt gaccaattat gaattgtctt ttattaatgg taagataaac taccaatatg    16260
ttgtgtatgt aggtgatccc gctcaattac cggcacctcg tacttacctt aatggttcac    16320
```

```
tttcaccaaa ggattataat gttgtaacaa accttatggt ttgcgttaaa cccgatatct   16380
tccttgcgaa gtgttaccgt tgtcctaagg aaattgtaga cactgtgtct actcttgttt   16440
atgatggaaa gtttattgca aataacccag aatcacgtca gtgtttcaag gttatagtta   16500
ataatggcaa ttctgatgta ggacatgaaa gtggttcagc ctacaacaca actcaattag   16560 aattttgtgaa agattttgtt tgtcgcaata aggagtggcg ggaagcaaca ttcatttcac   16620
cttataatgc tatgaaccag agagcctatc gtatgcttgg acttaatgtt cagacagtag   16680
actcgtctca aggttcagag tatgattatg ttatattctg tgttacagca gattcgaatc   16740
atgcactgaa tattaacaga ttcaatgtag cgcttacaag agctaagcgt ggtatactag   16800
ttgtcatgcg tcagcgtgat gaattgtatt cggctcttaa gtttacagag cttgatagtg   16860
aaacaagtct gcaaggtaca ggtttgttta aaatttgcaa caaggacttt agtggtgtcc   16920
atcctgctta tgcagtcaca actaaggctc ttgccgcaac ttataaagtt aatgatgaac   16980
ttgctgcact tgttaatgtg gaagctggtt cagaaataac atataaacat cttatttctc   17040
ttttaggatt taagatgagt gttaatgttg aaggctgcca caacatgttt ataacacgtg   17100
aagaggcaat tcgtaatgtg agaggttggg taggttttga tgtagaagct acacatgctt   17160
gtggtactaa catcggcact aacttgcctt tcaagtaggt ttctctact ggtgctgact   17220 ttatagtcac gcctgaggga attgtagata cttcaatagg caataatttt gagcctgtta   17280
attctaaggc acctccaggt gaacaattta atcacttaag ggctttattt aaaagtgcta   17340
aaccttggca tgttataaga ccaaggattg tacaaatgtt agcagacaac ctatgcaatg   17400
tttcagattg cgtagttttt gtaacttggt gtcatggtct agaactaact actttgcgct   17460 atttgttaa aataggcaaa gaacaagtat gttcttgtgg ttctagagct acaacattta   17520
attctcatac tcaagcttat gcttgttgga gcattgttt gggttttgat tttgtttata   17580
acccacttct agtggatgtt caacagtggg gttactctgg taacctacaa tttaatcatg   17640
acttgcactg taatgtgcat ggacacgcgc atgttgcctc tgcggatgct attatgacgc   17700
gttgtcttgc aattaacaat gcattttgtc aagatgtcaa ctgggatttg acataccctc   17760
atattgcaaa tgaggatgaa gtcaattcta gttgtagata cttacaacgc atgtatctta   17820
atgcatgtgt tgatgctctt aaaattaacg ttgtctatga tataggcaac cctaaaggta   17880
taaaatgtgt tagacgtgga gacttgagtt ttagattcta tgataagaat ccaatagtac   17940
ccaacgtcaa gcagtttgag tatgactata atcagcataa agataagttt gctgatggtc   18000
tttgtatgtt ctggaattgt aatgtggatt gttatcctga taattccttg gtttgcaggt   18060
atgacacacg aaatttgagt gtgtttaact taccaggttg taatggtggt agcctgtatg   18120
tcaataaaca tgcattccac acacctaaat tgatcgcat tagctttcgt aatttgaaag   18180
ctatgccatt cttttctat gactcatctc cttgcgaaac cattcaagtg gatggagttg   18240
cacaggatct tgtgtcacta gctactaaag attgtatcac aaaatgcaac ataggcggtg   18300
ctgtttgtaa gaaacatgcg cagatgtatg cagagtttgt gacttcttat aatgcagcgg   18360
taacagctgg ttttacttt tgggttacta ataattttaa cccatataat ttgtggaaaa   18420
gtttttcagc tctccagtct atcgataaca ttgcttataa tatgtataag ggtggtcatt   18480
acgacgctat tgcaggagaa atacccacca tcgtaactgg agataaagtt tttgttattg   18540
atcaaggtgt agaaaggca gttttttgtta atcaaacaac actgcctact tctgtggcgt   18600
ttgaactgta tgcgaagaga aatattcgca cactgccaaa caaccgtatt ttgaagggtc   18660
```

```
ttggtgtaga tgtaaccaat ggttttgtaa tttgggatta tgcgaaccaa acaccattat    18720
atcgtaatac tgttaaggta tgtgcataca cagacattga gccaaatggc ctaatagttc    18780
tgtatgatga tagatatggt gattaccaat ctttctcttgc cgctgataat gctgttctag   18840
tttctacaca gtgttataag cgatattcat atgtagaaat accgtcaaac atgcttgttc    18900
agaatggtat gccattaaaa gacggagcga atctgtatgt ctataagcgt gttaatggag    18960
cgtttgttac gctacctaac acactaaaca cacaaggtcg cagttatgaa acttttgaac    19020
ctcgtagcga cgttgagcgt gattttctcg acatgtcgga agaggatttt gtagaaaagt    19080
atggtaaaga cttaggtcta caacacatac tgtatggtga agttgataaa ccacaattgg    19140
gcggtttaca cactgttata ggtatgtaca gacttttacg tgcgaataag ttgaatgcaa    19200
agtctgttac taattcagat tctgatgtca tgcaaaatta ttttgtgttg gcagataatg    19260
gttcttacaa gcaagtgtgc actgttgtgg atttactgct tgatgatttc ttagaactgc    19320
ttaggaacat actgaatgag tatggtacta ataagtcaaa agttgtaaca gtgttaattg    19380
attaccatag cataaatttt atgacttggt ttgaagatgg cagtattaaa acatgttatc    19440
cacagcttca atcagcatgg acgtgtggtt ataatatgcc tgaactctat aaagtccaga    19500
attgtgttat ggaaccttgc aacattccta attatggtgt tggaataacg ttgccaagtg    19560
gtattatgat gaatgtggca aagtacacac aactttgtca ataccttcg aaaacaacaa     19620 tgtgtgtgcc gcataatg cgcgttatgc attttggagc tggcagtgat aaaggagtgg      19680
ctccaggtag tactgttctt aaacagtggc ttcctgaagg gacactcctt gtagataatg    19740
atattgtaga ttatgtgtct gatgcacatg tttctgtgct ttcagattgc aataaatata    19800
agacagagca caagtttgat cttgtgatat ctgatatgta tacagacaat gattcaaaaa    19860
gaaagcatga aggcgtgata gccaacaatg gcaatgatga cgttttcata tatctttcag   19920
actttcttcg taacaatttg gctcttggcg gcagttttgc tgtaaaggtg acagagacaa    19980
gttggcacga gaatttatat gacattgcac aagattgtgc atggtggaca atgtttgta    20040 ctgcagtgaa tgcttcttct tcagaagcat ttctggttgg tgttaattat ttgggtgcaa    20100
gtgaaaagct taaagttaat ggaaaaaccc tgcacgcaaa ttatatattt tggaggaatt    20160
gtaattattt acaaacctca gcttatagta tatttgacgt tgctaagttt gatttgaaat    20220
taaaagcaac gccagttgta aatttgaaaa ctgaacaaaa gaccgactta gtagttaatt    20280
tactaaggaa cggtaaattg ttagttagag atgttggtga agtcactgtt tctagtgacc    20340
attttgtttg cactatgtag tgctaatta tatgacaacg aatcttttgt gtattactac     20400
cagagtgctt ttaggccagg acatggttgg catttacatg gaggtgctta tgcagtagtt    20460
aatgtgtcta gtgaaaataa taatgcaggt actgccccaa gttgcactgc tggtgctatt    20520
ggctacagta agaatctcag tgcggcctca gtagccatga ctgcaccact aagtggtatg    20580
tcatggtctg ccaactcttt ttgtacagcc cactgtaatt ttacttctta tagtgtttt    20640 gttacacatt gttataagag cggatctaat agttgtcctt tgacaggtct tattccaagc    20700
ggttatattc gtattgctgc tatgaaacat ggaagtgcta tgcctggtca cttatttat     20760 aatttaacag tttctgtgac taaatatcct aagtttagat cgctacaatg tgttaataat    20820
catacttctg tatatttaaa tggtgacctt gttttcacat ctaactatac tgaagatgtt    20880
gtagctgcag gtgtccattt taaaagtggt ggacctataa cttataaagt tatgagagag    20940
gttaaagcct tggcttattt tgtcaatggt actgcacatg atgtcattct atgtgatgac    21000
acacctagag gtttgttagc atgccaatat aatactggca atttttcaga tggcttctat    21060
```

```
cctttttacta atactagtat tgttaaggat aagtttattg tttatcgtga aagtagtgtc  21120
aatactactt taacattaac taatttcacg tttagtaatg aaagtggtgc ccctcctaat  21180
acaggtggtg ttgacagttt tattttatac cagacacaaa cagctcagag tggttattat  21240
aattttaact tttcatttct gagtagtttt gtttataggg aaagttatta tatgtatgga  21300
tcttaccatc cacgttgtag ttttagacct gaaacccctta ataatggttt gtggtttaat  21360
tccctttctg tttcattaac atacggtccc attcaaggtg gttgtaagca atctgtattt  21420
aatggtaaag caacttgttg ttatgcttat tcatacggag gacctcgtgg ttgtaaaggt  21480
gtctatagag gtgagctaac acagcatttt gaatgtggtt tgttagttta tgttactaag  21540
agcgatggct cccgtataca aactgcaaca caaccacctg tattaaccca aaatttttat  21600
aataacatca atttaggtaa gtgtgttgat tataatatat atggcagaat tggccaaggt  21660
cttattacta atgtaaccga cttagctgtt agttataatt atttatcaga cgcaggtttg  21720
gctattttag atacatctgg tgccatagac atcttcgttg tacaaggtga atatggtcct  21780
aactattata aggttaatcc atgtgaagat gtcaaccaac agtttgtagt ttctggtggt  21840
aaattagtag gtattctcac ttcacgtaat gaaacaggtt ctcagcttct tgagaaccag  21900
ttttatatta aaatcactaa tggaactcgt cgttctagac gttctgttac tgaaaatgtt  21960
acaaattgcc cttatgttag ttatggcaag ttttgtataa aacctgatgg ttcaatttct  22020
gtaatagtac caaaagaact ggatcagttt gtggcaccctt tacttaatgt tactgaatat  22080
gtgctcatac ctaacagttt taattttaact gttacagatg agtacataca aacgcgtatg  22140
gataagatcc aaattaattg cctgcagtat gttttgtggca attctttggc ctgtagaaag  22200
ctgtttcaac aatatgggcc tgtttgtgac aacatattgt ctgtagtaaa tagtgttggt  22260
caaaaagaag atatggaact tttaaatttc tattcttcta ctaaaccagc tcgttttaat  22320
acaccagttt ttagtaatct tagcactggt gagtttaata tttctctttt gttaacaccc  22380
cctagtagtc ctaggaggcg ttcttttatt gaagatcttt tatttacaag tgttgaatct  22440
gtaggattac caacagatga cgcatacaaa aagtgcactg caggacccttt aggctttctt  22500 aaagaccttg catgtgctcg tgaatataat ggtttgcttg tgttgcctcc tattataaca  22560
gcagaaatgc aaactttgta tactagttct ttagtagctt ctatggcttt tggtggtatt  22620
actgcagctg gtgccatacc ttttgccaca caactgcagg ctagaattaa tcacttgggt  22680
attacccagt cacttttgtt gaagaatcaa gaaaaaattg ctgcttcctt taataaggcc  22740
attggtcata tgcaggaagg ttttagagt acatctctag cattcaaaca aattcaagat  22800
gttgttaata gcagagtgc tattcttact gagactatgg cagcacttaa taaaaatttt  22860
ggtgctattt cttctgtgat tcaagacatt accagcaac ttgattccat acaagcagat  22920
gctcaagtgg atcggctcat aactggtaga ttgtcatcac tttctgtctt agcatctgct  22980
aagcagtcgg agtacattag agtgtcacaa cagcgtgagt tagctactca gaaaattaat  23040
gagtgtgtta aatcacagtc tattaggtat tccttttgtg gtaatggacg acatgttta  23100 accataccac aaaatgcccc taatggtata gtgtttatac actttactta tacaccagag  23160
agctttatta tgttactgc aatagtgggt tttttgtaa gtcctgctaa tgctagtcag  23220
tatgcaatag tgcccgctaa tggtaggggt attttatac aagttaatgg tagttactac  23280
atcactgcac gagatatgta tatgccaaga gatattactg caggagatat agttacgcct  23340
acttcttgtc aagcaaatta tgtaagtgta ataagaccg tcattactac atttgtagac  23400
```

```
aatgatgatt ttgattttga tgatgaattg tcaaaatggt ggaatgatac taagcatgag   23460
ctaccagact ttgacaaatt caattacaca gtacctatac ttgacattga tagtgaaatt   23520
gatcgtattc aaggcgttat acagggtctt aacgactctc taatagacct tgaaacacta   23580
tcaatactca aaacttatat taagtggcct tggtatgtgt ggttagccat agcttttgcc   23640
actattatct tcatcttaat actaggatgg ttgttttttca tgactggttg ttgtggttgt   23700
tgttgtggat gctttggcat tattccttta atgagtaagt gtggtaagaa atcttcttat   23760
tacacgactt ttgataatga tgtggtaact gaacaataca gacctaaaaa gtctgtttaa   23820
tgattcaaag tcccacatct tttctaatag tattaattttt tctttggtgt aaacttgcac   23880
taagttgttt taaagagtgt gttatagcac tccagcaact aatacaagtt ttactccaaa   23940
ttattaatag taacttacag tctagacttc tgctttggca cagtctagac taatgttaga   24000
ttttgaagca attattgaaa ctggtcagca ataattcaa caaatcagtt tcgatttaca   24060
gcaaatttca agtgtgctaa gcactgaatt atttgacccc tttgaagtct gtgtttacag   24120
aggaggtaat tattgggagt tagagtcagc tgacgagttt tcaggtgatg acgaatatat   24180
tgagtaaatc gctagaggag aacggaagtt tcctaacagc agtttacata tttgttggat   24240
ttttagcatt ttacctatta ggtagagcac tccaagcatt tgtacaagct gctgatgctt   24300
gttgtttatt ttggtataca tgggtagtag ttcctggagc taagggtaca gcctttgtgt   24360
ataatcatac atatggtaaa aaacttaaca aaccggagtt agaagcggtt attgttaacg   24420
agttccccaa gaacggttgg aataataaaa gtccagcaaa tttccaatat gatggaaaat   24480
tgcacactta acttagagca ggcaactctg cttttttaaag aatataatttt atttataacc   24540 gcattcctat tgtttcttac tatactactt cagtatgggt acgcaactag gagtcggttt   24600
atttatatac tgaaaatgat agtgttatgg tgcttttggc cccttaacat tgcagtaggt   24660 gtaattttcat gtatatatcc accaaataca ggaggtcttg tcgcagcgat aatacttact   24720
gtgtttgctt gtctttcttt tgtaggttat tggattcaga gttgtagact ctttaaaagg   24780
tgtaggtctt ggtggtcttt taaccccgag tctaatgccg taggttcaat actcctcaca   24840
aatggtcaac aatgtaattt tgctatagag agtgtgccta tggtgcttgc tccaattata   24900
aagaacggtg tccttttattg tgagggtcag tggcttgcta aatgtgaacc agaccacttg   24960
cctaaagaca tatttgtatg cacaccggat agacgtaata tctatcgtat ggtgcagaaa   25020
tacactggtg accaaagcgg aaataagaaa aggtttgcta catttgtcta tgcaaagcag   25080
tcagtagaca ctggcgagct agaaagtgta gcaacaggag gaagtagtct ttacacataa   25140
atgtgtgtgt gtagagagta tttaagacta ttctttaata gtgcctctat tttaagagcg   25200
catacgagta tttatttga ggatattaat ataaatcctc tttgttttat actctctttt   25260
caagagctat tatttaaaaa acagtttttc cactctttttg tgccaaaaac tattgttgtt   25320
aacggtgtta cctttcaagt ggataatgga aaagtctact acgaaggaac accagttttc   25380
caaaaaggtt gttgtagaat gtggtccaat tataagaaag attagaataa ttaagccacc   25440
aactacactt attttttataa gaggcgtttt atcttacaaa cgcttaacaa atacggacga   25500
tgaaatggct gactagtttt ggaagagcag ttatttcatg ttataaagcc ctactattaa   25560
ctcaattaag agtgttagat aggttaatttt taggtcacgg accaaaacgc gttttaacgt   25620
gtagtaggcg agtgcttttg tttcagttag atttagttta taggttggcg tttacgccca   25680
cccaatcgct ggtatgaata atagtaaaga taatccttttt cgcggagcaa tagcaagaaa   25740
agcgcgaatt tatctgagag aaggattaga ttgtgtttac tttcttaaca aagcaggaca   25800
```

-continued

```
agcagagcct tgtcccgcgt gtacctctct agtattccaa gggaaaactt gtgaggcaca    25860
cataaataat aataatcttt tgtcatggca agcggtaagg caactggaaa gacagacgcc    25920
ccagcgccag tcatcaaact aggaggacca aagccaccta agttggttc ttctggaaat     25980 gcatcttggt ttcaagcaat aaaagccaag aagctaaatt cacctccacc taagtttgaa    26040
ggtagcggtg ttcctgataa tgaaaatctt aaaacaagcc agcaacatgg atactggaga    26100
cgccaagcta ggtttaagcc aggtaaaggc ggaagaaaac cagtcccaga tgcttggtac    26160
ttctattata ctggaacagg accagccgct gacctgaatt ggggtgatag ccaagatggt    26220
atagtgtggg ttgctgcaaa gggtgctgat gttaaatcta gatctaacca gggtacaagg    26280
gaccctgaca gtttgacca atatccacta cgattctcgg acggaggacc tgatggtaat     26340
ttccgttggg acttcattcc tctgaatcgt ggtaggagtg aagatcaac agcagcttca     26400 tcagcagcat ctagtagagc accgtcgcgt gacggctcgc gtggtcgtag aagtggttct    26460
gaagatgatc ttattgctcg tgcagcaaag ataatccagg atcagcagaa gaagggttct    26520
cgcattacta aggctaaggc tgatgaaatg gctcatcgcc ggtattgcaa gcgcattatt    26580
ccacctggtt ataaggttga tcaagtcttt ggtccccgta ctaaaggtaa ggagggaaat    26640
tttggtgatg acaagatgaa tgaggaaggt attaaggatg gcgtgttac ggcaatgctc     26700 aacctagtcc ctagcagcca tgcttgcctt tttggaagta gggtgacgcc caaacttcaa    26760
ccagatgggc ttcacttgag atttgaattt actactgtgg tcccgcgtga tgatccgcag    26820
tttgataatt atgtgaaaat ttgtgaccag tgtgttgatg gtgtaggaac acgtccaaaa    26880
gatgacgaac cgagaccaaa gtcacgctca agttcaagac ctgctacaag aacaagttct    26940
ccggcgccaa gacaacaacg cccaaagaag gagaaaaagt caagaagca ggatgatgaa     27000 gtagataaag cattgacctc agatgaggag aggaacaatg cacagctgga atttgatgat    27060
gaacccaagg ttattaactg gggggattca gctttaggtg agaatgaact ttgagtaaca    27120
taatggacct gctgcatttt ttggtacatt ttgttaaaca ctatttctgt gctttcctat    27180
caattattac aggcattgat tgtgattatg tgcaatattt aagcttcttt tggttgcttt    27240
ttgcttgttg tgttgttgct gtgcttttta ttattgtgat tctcattagt ttgttttatc    27300
gtagaagttc aatagtaaga gttaaggaag ataggcatgt agcttagcac ctacatgtct    27360
atcgccaggg aaatgtctaa tctgtctact tagtagcctg gaaacgaacg gtagaccctt    27420
agattttaat ttagtttaat ttttagttta gtttaagtta gtttagagta ggtataaaga    27480
tgccagtgcc ggggccacgc ggagtacgat cgagggtaca gcactaggac gcccattaag    27540
ggaagagcta aattttagtt taagttaagt ttaattggct aagtatagtt aaaatttgta    27600
ggctagtata gagttagagc aaaaaaaaaa aaaaaa                              27636
```

<210> SEQ ID NO 2
<211> LENGTH: 3510
<212> TYPE: DNA
<213> ORGANISM: Infectious Bronchitis Virus

<400> SEQUENCE: 2

```
atgttggtga agtcactgtt tctagtgacc attttgtttg cactatgtag tgctaattta     60
tatgacaacg aatcttttgt gtattactac cagagtgctt ttaggccagg acatggttgg    120
catttacatg gaggtgctta tgcagtagtt aatgtgtcta gtgaaaataa taatgcaggt    180
actgccccaa gttgcactgc tggtgctatt ggctacagta agaatctcag tgcggcctca    240
```

```
gtagccatga ctgcaccact aagtggtatg tcatggtctg ccaactcttt ttgtacagcc    300
cactgtaatt ttacttctta tatagtgttt gttacacatt gttataagag cggatctaat    360
agttgtcctt tgacaggtct tattccaagc ggttatattc gtattgctgc tatgaaacat    420
ggaagtgcta tgcctggtca cttattttat aatttaacag tttctgtgac taaatatcct    480
aagtttagat cgctacaatg tgttaataat catacttctg tatatttaaa tggtgacctt    540
gttttcacat ctaactatac tgaagatgtt gtagctgcag gtgtccattt taaaagtggt    600
ggacctataa cttataaagt tatgagagag gttaaagcct tggcttattt tgtcaatggt    660
actgcacatg atgtcattct atgtgatgac acacctagag gtttgttagc atgccaatat    720
aatactggca attttcaga tggcttctat cctttacta atactagtat tgttaaggat    780
aagtttattg tttatcgtga aagtagtgtc aatactactt taacattaac taatttcacg    840
tttagtaatg aaagtggtgc ccctcctaat acaggtggtg ttgacagttt tatttatac    900 cagacacaaa cagctcagag tggttattat aattttaact tttcatttct gagtagtttt    960
gtttataggg aaagttatta tatgtatgga tcttaccatc cacgttgtag ttttagacct   1020 gaaacccctta ataatggttt gtggtttaat tcccttttctg tttcattaac atacggtccc   1080
attcaaggtg gttgtaagca atctgtattt aatggtaaag caacttgttg ttatgcttat   1140
tcatacggag gacctcgtgg ttgtaaaggt gtctatagag gtgagctaac acagcatttt   1200
gaatgtggtt tgttagttta tgttactaag agcgatggct cccgtataca aactgcaaca   1260
caaccacctg tattaaccca aaatttttat aataacatca atttaggtaa gtgtgttgat   1320
tataatatat atggcagaat tggccaaggt cttattacta atgtaaccga cttagctgtt   1380
agttataatt atttatcaga cgcaggtttg gctatttag atacatctgg tgccatagac   1440
atcttcgttg tacaaggtga aatggtcct aactattata aggttaatcc atgtgaagat   1500
gtcaaccaac agtttgtagt ttctggtggt aaattagtag gtattctcac ttcacgtaat   1560
gaaacaggtt ctcagcttct tgagaaccag ttttatatta aaatcactaa tggaactcgt   1620
cgttctagac gttctgttac tgaaaatgtt acaaattgcc cttatgttag ttatggcaag   1680
ttttgtataa aacctgatgg ttcaatttct gtaaatagtac caaaagaact ggatcagttt   1740
gtggcacctt tacttaatgt tactgaatat gtgctcatac ctaacagttt taatttaact   1800
gttacagatg agtacataca aacgcgtatg gataagatcc aaattaattg cctgcagtat   1860
gtttgtggca attctttggc ctgtagaaag ctgtttcaac aatatgggcc tgtttgtgac   1920
aacatattgt ctgtagtaaa tagtgttggt caaaagaag atatggaact tttaaatttc   1980
tattcttcta ctaaaccagc tcgttttaat acaccagttt ttagtaatct tagcactggt   2040
gagtttaata tttctctttt gttaacaccc cctagtagtc ctaggaggcg ttctttatt   2100 gaagatcttt tatttacaag tgttgaatct gtaggattac caacagatga cgcatacaaa   2160
aagtgcactg caggacctt aggctttctt aaagaccttg catgtgctcg tgaatataat   2220
ggtttgcttg tgttgcctcc tattataaca gcagaaatgc aaactttgta tactagttct   2280
ttagtagctt ctatggcttt tggtggtatt actgcagctg gtgccatacc ttttgccaca   2340
caactgcagg ctagaattaa tcacttgggt attacccagt cacttttgtt gaagaatcaa   2400
gaaaaaattg ctgcttcctt taataaggcc attggtcata tgcaggaagg ttttaggagt   2460
acatctctag cattacaaca aattcaagat gttgttaata agcagagtgc tattcttact   2520
gagactatgc cagcacttaa taaaaatttt ggtgctattt cttctgtgat tcaagacatt   2580
taccagcaac ttgattccat acaagcagat gctcaagtgg atcggctcat aactggtaga   2640
```

```
ttgtcatcac tttctgtctt agcatctgct aagcagtcgg agtacattag agtgtcacaa    2700
cagcgtgagt tagctactca gaaaattaat gagtgtgtta atcacagtc tattaggtat      2760 tccttttgtg gtaatggacg acatgtttta accataccac aaaatgcccc taatggtata    2820
gtgtttatac actttactta tacaccagag agctttatta atgttactgc aatagtgggt    2880
ttttgtgtaa gtcctgctaa tgctagtcag tatgcaatag tgcccgctaa tggtaggggt    2940 attttttatac aagttaatgg tagttactac atcactgcac gagatatgta tatgccaaga    3000
gatattactg caggagatat agttacgctt acttcttgtc aagcaaatta tgtaagtgta    3060
aataagaccg tcattactac atttgtagac aatgatgatt ttgattttga tgatgaattg    3120
tcaaaatggt ggaatgatac taagcatgag ctaccagact ttgacaaatt caattacaca    3180
gtacctatac ttgacattga tagtgaaatt gatcgtattc aaggcgttat acagggtctt    3240
aacgactctc taatagacct tgaaacacta tcaatactca aaacttatat taagtggcct    3300
tggtatgtgt ggttagccat agcttttgcc actattatct tcatcttaat actaggatgg    3360 ttgttttttca tgactggttg ttgtggttgt tgttgtggat gctttggcat tattcccttta    3420 atgagtaagt gtggtaagaa atcttcttat tacacgactt ttgataatga tgtggtaact    3480
gaacaataca gacctaaaaa gtctgtttaa                                      3510
```

<210> SEQ ID NO 3
<211> LENGTH: 1169
<212> TYPE: PRT
<213> ORGANISM: Infectious Bronchitis Virus

<400> SEQUENCE: 3

```
Met Leu Val Lys Ser Leu Phe Leu Val Thr Ile Leu Phe Ala Leu Cys
1               5                   10                  15

Ser Ala Asn Leu Tyr Asp Asn Glu Ser Phe Val Tyr Tyr Gln Ser
                20                  25                  30

Ala Phe Arg Pro Gly His Gly Trp His Leu His Gly Gly Ala Tyr Ala
            35                  40                  45

Val Val Asn Val Ser Ser Glu Asn Asn Ala Gly Thr Ala Pro Ser
        50                  55                  60

Cys Thr Ala Gly Ala Ile Gly Tyr Ser Lys Asn Leu Ser Ala Ala Ser
65                  70                  75                  80

Val Ala Met Thr Ala Pro Leu Ser Gly Met Ser Trp Ser Ala Asn Ser
                85                  90                  95

Phe Cys Thr Ala His Cys Asn Phe Thr Ser Tyr Ile Val Phe Val Thr
            100                 105                 110

His Cys Tyr Lys Ser Gly Ser Asn Ser Cys Pro Leu Thr Gly Leu Ile
        115                 120                 125

Pro Ser Gly Tyr Ile Arg Ile Ala Ala Met Lys His Gly Ser Ala Met
    130                 135                 140

Pro Gly His Leu Phe Tyr Asn Leu Thr Val Ser Val Thr Lys Tyr Pro
145                 150                 155                 160

Lys Phe Arg Ser Leu Gln Cys Val Asn Asn His Thr Ser Val Tyr Leu
                165                 170                 175

Asn Gly Asp Leu Val Phe Thr Ser Asn Tyr Thr Glu Asp Val Val Ala
            180                 185                 190

Ala Gly Val His Phe Lys Ser Gly Gly Pro Ile Thr Tyr Lys Val Met
        195                 200                 205

Arg Glu Val Lys Ala Leu Ala Tyr Phe Val Asn Gly Thr Ala His Asp
```

```
            210                 215                 220
Val Ile Leu Cys Asp Asp Thr Pro Arg Gly Leu Leu Ala Cys Gln Tyr
225                 230                 235                 240

Asn Thr Gly Asn Phe Ser Asp Gly Phe Tyr Pro Phe Thr Asn Thr Ser
                    245                 250                 255

Ile Val Lys Asp Lys Phe Ile Val Tyr Arg Glu Ser Ser Val Asn Thr
                260                 265                 270

Thr Leu Thr Leu Thr Asn Phe Thr Phe Ser Asn Glu Ser Gly Ala Pro
            275                 280                 285

Pro Asn Thr Gly Gly Val Asp Ser Phe Ile Leu Tyr Gln Thr Gln Thr
        290                 295                 300

Ala Gln Ser Gly Tyr Tyr Asn Phe Asn Phe Ser Phe Leu Ser Ser Phe
305                 310                 315                 320

Val Tyr Arg Glu Ser Tyr Tyr Met Tyr Gly Ser Tyr His Pro Arg Cys
                325                 330                 335

Ser Phe Arg Pro Glu Thr Leu Asn Asn Gly Leu Trp Phe Asn Ser Leu
                340                 345                 350

Ser Val Ser Leu Thr Tyr Gly Pro Ile Gln Gly Gly Cys Lys Gln Ser
            355                 360                 365

Val Phe Asn Gly Lys Ala Thr Cys Cys Tyr Ala Tyr Ser Tyr Gly Gly
        370                 375                 380

Pro Arg Gly Cys Lys Gly Val Tyr Arg Gly Glu Leu Thr Gln His Phe
385                 390                 395                 400

Glu Cys Gly Leu Leu Val Tyr Val Thr Lys Ser Asp Gly Ser Arg Ile
                405                 410                 415

Gln Thr Ala Thr Gln Pro Pro Val Leu Thr Gln Asn Phe Tyr Asn Asn
                420                 425                 430

Ile Asn Leu Gly Lys Cys Val Asp Tyr Asn Ile Tyr Gly Arg Ile Gly
            435                 440                 445

Gln Gly Leu Ile Thr Asn Val Thr Asp Leu Ala Val Ser Tyr Asn Tyr
        450                 455                 460

Leu Ser Asp Ala Gly Leu Ala Ile Leu Asp Thr Ser Gly Ala Ile Asp
465                 470                 475                 480

Ile Phe Val Val Gln Gly Glu Tyr Gly Pro Asn Tyr Tyr Lys Val Asn
                485                 490                 495

Pro Cys Glu Asp Val Asn Gln Gln Phe Val Val Ser Gly Gly Lys Leu
                500                 505                 510

Val Gly Ile Leu Thr Ser Arg Asn Glu Thr Gly Ser Gln Leu Leu Glu
            515                 520                 525

Asn Gln Phe Tyr Ile Lys Ile Thr Asn Gly Thr Arg Arg Ser Arg Arg
        530                 535                 540

Ser Val Thr Glu Asn Val Thr Asn Cys Pro Tyr Val Ser Tyr Gly Lys
545                 550                 555                 560

Phe Cys Ile Lys Pro Asp Gly Ser Ile Ser Val Ile Val Pro Lys Glu
                565                 570                 575

Leu Asp Gln Phe Val Ala Pro Leu Leu Asn Val Thr Glu Tyr Val Leu
                580                 585                 590

Ile Pro Asn Ser Phe Asn Leu Thr Val Thr Asp Glu Tyr Ile Gln Thr
            595                 600                 605

Arg Met Asp Lys Ile Gln Ile Asn Cys Leu Gln Tyr Val Cys Gly Asn
        610                 615                 620

Ser Leu Ala Cys Arg Lys Leu Phe Gln Gln Tyr Gly Pro Val Cys Asp
625                 630                 635                 640
```

```
Asn Ile Leu Ser Val Val Asn Ser Val Gly Gln Lys Glu Asp Met Glu
            645                 650                 655

Leu Leu Asn Phe Tyr Ser Ser Thr Lys Pro Ala Arg Phe Asn Thr Pro
            660                 665                 670

Val Phe Ser Asn Leu Ser Thr Gly Glu Phe Asn Ile Ser Leu Leu Leu
            675                 680                 685

Thr Pro Pro Ser Ser Pro Arg Arg Arg Ser Phe Ile Glu Asp Leu Leu
            690                 695                 700

Phe Thr Ser Val Glu Ser Val Gly Leu Pro Thr Asp Asp Ala Tyr Lys
705                 710                 715                 720

Lys Cys Thr Ala Gly Pro Leu Gly Phe Leu Lys Asp Leu Ala Cys Ala
            725                 730                 735

Arg Glu Tyr Asn Gly Leu Leu Val Leu Pro Pro Ile Ile Thr Ala Glu
            740                 745                 750

Met Gln Thr Leu Tyr Thr Ser Ser Leu Val Ala Ser Met Ala Phe Gly
            755                 760                 765

Gly Ile Thr Ala Ala Gly Ala Ile Pro Phe Ala Thr Gln Leu Gln Ala
            770                 775                 780

Arg Ile Asn His Leu Gly Ile Thr Gln Ser Leu Leu Leu Lys Asn Gln
785                 790                 795                 800

Glu Lys Ile Ala Ala Ser Phe Asn Lys Ala Ile Gly His Met Gln Glu
            805                 810                 815

Gly Phe Arg Ser Thr Ser Leu Ala Leu Gln Gln Ile Gln Asp Val Val
            820                 825                 830

Asn Lys Gln Ser Ala Ile Leu Thr Glu Thr Met Ala Ala Leu Asn Lys
            835                 840                 845

Asn Phe Gly Ala Ile Ser Ser Val Ile Gln Asp Ile Tyr Gln Gln Leu
            850                 855                 860

Asp Ser Ile Gln Ala Asp Ala Gln Val Asp Arg Leu Ile Thr Gly Arg
865                 870                 875                 880

Leu Ser Ser Leu Ser Val Leu Ala Ser Ala Lys Gln Ser Glu Tyr Ile
            885                 890                 895

Arg Val Ser Gln Gln Arg Glu Leu Ala Thr Gln Lys Ile Asn Glu Cys
            900                 905                 910

Val Lys Ser Gln Ser Ile Arg Tyr Ser Phe Cys Gly Asn Gly Arg His
            915                 920                 925

Val Leu Thr Ile Pro Gln Asn Ala Pro Asn Gly Ile Val Phe Ile His
            930                 935                 940

Phe Thr Tyr Thr Pro Glu Ser Phe Ile Asn Val Thr Ala Ile Val Gly
945                 950                 955                 960

Phe Cys Val Ser Pro Ala Asn Ala Ser Gln Tyr Ala Ile Val Pro Ala
            965                 970                 975

Asn Gly Arg Gly Ile Phe Ile Gln Val Asn Gly Ser Tyr Tyr Ile Thr
            980                 985                 990

Ala Arg Asp Met Tyr Met Pro Arg Asp Ile Thr Ala Gly Asp Ile Val
            995                 1000                1005

Thr Leu Thr Ser Cys Gln Ala Asn Tyr Val Ser Val Asn Lys Thr
    1010                1015                1020

Val Ile Thr Thr Phe Val Asp Asn Asp Asp Phe Asp Phe Asp Asp
    1025                1030                1035

Glu Leu Ser Lys Trp Trp Asn Asp Thr Lys His Glu Leu Pro Asp
    1040                1045                1050
```

-continued

```
Phe Asp Lys Phe Asn Tyr Thr Val Pro Ile Leu Asp Ile Asp Ser
    1055                1060                1065

Glu Ile Asp Arg Ile Gln Gly Val Ile Gln Gly Leu Asn Asp Ser
    1070                1075                1080

Leu Ile Asp Leu Glu Thr Leu Ser Ile Leu Lys Thr Tyr Ile Lys
    1085                1090                1095

Trp Pro Trp Tyr Val Trp Leu Ala Ile Ala Phe Ala Thr Ile Ile
    1100                1105                1110

Phe Ile Leu Ile Leu Gly Trp Leu Phe Phe Met Thr Gly Cys Cys
    1115                1120                1125

Gly Cys Cys Cys Gly Cys Phe Gly Ile Ile Pro Leu Met Ser Lys
    1130                1135                1140

Cys Gly Lys Lys Ser Ser Tyr Tyr Thr Thr Phe Asp Asn Asp Val
    1145                1150                1155

Val Thr Glu Gln Tyr Arg Pro Lys Lys Ser Val
    1160                1165

<210> SEQ ID NO 4
<211> LENGTH: 544
<212> TYPE: PRT
<213> ORGANISM: Infectious Bronchitis Virus

<400> SEQUENCE: 4

Met Leu Val Lys Ser Leu Phe Leu Val Thr Ile Leu Phe Ala Leu Cys
1               5                   10                  15

Ser Ala Asn Leu Tyr Asp Asn Glu Ser Phe Val Tyr Tyr Gln Ser
            20                  25                  30

Ala Phe Arg Pro Gly His Gly Trp His Leu His Gly Gly Ala Tyr Ala
            35                  40                  45

Val Val Asn Val Ser Ser Glu Asn Asn Asn Ala Gly Thr Ala Pro Ser
        50                  55                  60

Cys Thr Ala Gly Ala Ile Gly Tyr Ser Lys Asn Leu Ser Ala Ala Ser
65                  70                  75                  80

Val Ala Met Thr Ala Pro Leu Ser Gly Met Ser Trp Ser Ala Asn Ser
                85                  90                  95

Phe Cys Thr Ala His Cys Asn Phe Thr Ser Tyr Ile Val Phe Val Thr
            100                 105                 110

His Cys Tyr Lys Ser Gly Ser Asn Ser Cys Pro Leu Thr Gly Leu Ile
            115                 120                 125

Pro Ser Gly Tyr Ile Arg Ile Ala Ala Met Lys His Gly Ser Ala Met
        130                 135                 140

Pro Gly His Leu Phe Tyr Asn Leu Thr Val Ser Val Thr Lys Tyr Pro
145                 150                 155                 160

Lys Phe Arg Ser Leu Gln Cys Val Asn Asn His Thr Ser Val Tyr Leu
                165                 170                 175

Asn Gly Asp Leu Val Phe Thr Ser Asn Tyr Thr Glu Asp Val Val Ala
            180                 185                 190

Ala Gly Val His Phe Lys Ser Gly Gly Pro Ile Thr Tyr Lys Val Met
            195                 200                 205

Arg Glu Val Lys Ala Leu Ala Tyr Phe Val Asn Gly Thr Ala His Asp
        210                 215                 220

Val Ile Leu Cys Asp Asp Thr Pro Arg Gly Leu Leu Ala Cys Gln Tyr
225                 230                 235                 240

Asn Thr Gly Asn Phe Ser Asp Gly Phe Tyr Pro Phe Thr Asn Thr Ser
                245                 250                 255
```

```
Ile Val Lys Asp Lys Phe Ile Val Tyr Arg Glu Ser Ser Val Asn Thr
                260                 265                 270

Thr Leu Thr Leu Thr Asn Phe Thr Phe Ser Asn Glu Ser Gly Ala Pro
            275                 280                 285

Pro Asn Thr Gly Gly Val Asp Ser Phe Ile Leu Tyr Gln Thr Gln Thr
        290                 295                 300

Ala Gln Ser Gly Tyr Tyr Asn Phe Asn Phe Ser Phe Leu Ser Ser Phe
305                 310                 315                 320

Val Tyr Arg Glu Ser Tyr Tyr Met Tyr Gly Ser Tyr His Pro Arg Cys
                325                 330                 335

Ser Phe Arg Pro Glu Thr Leu Asn Asn Gly Leu Trp Phe Asn Ser Leu
            340                 345                 350

Ser Val Ser Leu Thr Tyr Gly Pro Ile Gln Gly Gly Cys Lys Gln Ser
        355                 360                 365

Val Phe Asn Gly Lys Ala Thr Cys Cys Tyr Ala Tyr Ser Tyr Gly Gly
    370                 375                 380

Pro Arg Gly Cys Lys Gly Val Tyr Arg Gly Glu Leu Thr Gln His Phe
385                 390                 395                 400

Glu Cys Gly Leu Leu Val Tyr Val Thr Lys Ser Asp Gly Ser Arg Ile
                405                 410                 415

Gln Thr Ala Thr Gln Pro Pro Val Leu Thr Gln Asn Phe Tyr Asn Asn
            420                 425                 430

Ile Asn Leu Gly Lys Cys Val Asp Tyr Asn Ile Tyr Gly Arg Ile Gly
        435                 440                 445

Gln Gly Leu Ile Thr Asn Val Thr Asp Leu Ala Val Ser Tyr Asn Tyr
    450                 455                 460

Leu Ser Asp Ala Gly Leu Ala Ile Leu Asp Thr Ser Gly Ala Ile Asp
465                 470                 475                 480

Ile Phe Val Val Gln Gly Glu Tyr Gly Pro Asn Tyr Tyr Lys Val Asn
                485                 490                 495

Pro Cys Glu Asp Val Asn Gln Gln Phe Val Val Ser Gly Gly Lys Leu
            500                 505                 510

Val Gly Ile Leu Thr Ser Arg Asn Glu Thr Gly Ser Gln Leu Leu Glu
        515                 520                 525

Asn Gln Phe Tyr Ile Lys Ile Thr Asn Gly Thr Arg Arg Ser Arg Arg
    530                 535                 540

<210> SEQ ID NO 5
<211> LENGTH: 625
<212> TYPE: PRT
<213> ORGANISM: Infectious Bronchitis Virus

<400> SEQUENCE: 5

Ser Val Thr Glu Asn Val Thr Asn Cys Pro Tyr Val Ser Tyr Gly Lys
1

```
                        85                  90                  95
Asn Ile Leu Ser Val Val Asn Ser Val Gly Gln Lys Glu Asp Met Glu
            100                 105                 110

Leu Leu Asn Phe Tyr Ser Ser Thr Lys Pro Ala Arg Phe Asn Thr Pro
            115                 120                 125

Val Phe Ser Asn Leu Ser Thr Gly Glu Phe Asn Ile Ser Leu Leu Leu
            130                 135                 140

Thr Pro Pro Ser Pro Arg Arg Ser Phe Ile Glu Asp Leu Leu
145                 150                 155                 160

Phe Thr Ser Val Glu Ser Val Gly Leu Pro Thr Asp Asp Ala Tyr Lys
                165                 170                 175

Lys Cys Thr Ala Gly Pro Leu Gly Phe Leu Lys Asp Leu Ala Cys Ala
                180                 185                 190

Arg Glu Tyr Asn Gly Leu Leu Val Leu Pro Pro Ile Ile Thr Ala Glu
                195                 200                 205

Met Gln Thr Leu Tyr Thr Ser Ser Leu Val Ala Ser Met Ala Phe Gly
            210                 215                 220

Gly Ile Thr Ala Ala Gly Ala Ile Pro Phe Ala Thr Gln Leu Gln Ala
225                 230                 235                 240

Arg Ile Asn His Leu Gly Ile Thr Gln Ser Leu Leu Lys Asn Gln
                245                 250                 255

Glu Lys Ile Ala Ala Ser Phe Asn Lys Ala Ile Gly His Met Gln Glu
                260                 265                 270

Gly Phe Arg Ser Thr Ser Leu Ala Leu Gln Gln Ile Gln Asp Val Val
                275                 280                 285

Asn Lys Gln Ser Ala Ile Leu Thr Glu Thr Met Ala Ala Leu Asn Lys
290                 295                 300

Asn Phe Gly Ala Ile Ser Ser Val Ile Gln Asp Ile Tyr Gln Gln Leu
305                 310                 315                 320

Asp Ser Ile Gln Ala Asp Ala Gln Val Asp Arg Leu Ile Thr Gly Arg
                325                 330                 335

Leu Ser Ser Leu Ser Val Leu Ala Ser Ala Lys Gln Ser Glu Tyr Ile
                340                 345                 350

Arg Val Ser Gln Gln Arg Glu Leu Ala Thr Gln Lys Ile Asn Glu Cys
                355                 360                 365

Val Lys Ser Gln Ser Ile Arg Tyr Ser Phe Cys Gly Asn Gly Arg His
            370                 375                 380

Val Leu Thr Ile Pro Gln Asn Ala Pro Asn Gly Ile Val Phe Ile His
385                 390                 395                 400

Phe Thr Tyr Thr Pro Glu Ser Phe Ile Asn Val Thr Ala Ile Val Gly
                405                 410                 415

Phe Cys Val Ser Pro Ala Asn Ala Ser Gln Tyr Ala Ile Val Pro Ala
                420                 425                 430

Asn Gly Arg Gly Ile Phe Ile Gln Val Asn Gly Ser Tyr Tyr Ile Thr
                435                 440                 445

Ala Arg Asp Met Tyr Met Pro Arg Asp Ile Thr Ala Gly Asp Ile Val
                450                 455                 460

Thr Leu Thr Ser Cys Gln Ala Asn Tyr Val Ser Val Asn Lys Thr Val
465                 470                 475                 480

Ile Thr Thr Phe Val Asp Asn Asp Asp Phe Asp Phe Asp Asp Glu Leu
                485                 490                 495

Ser Lys Trp Trp Asn Asp Thr Lys His Glu Leu Pro Asp Phe Asp Lys
                500                 505                 510
```

-continued

```
Phe Asn Tyr Thr Val Pro Ile Leu Asp Ile Asp Ser Glu Ile Asp Arg
        515                 520                 525

Ile Gln Gly Val Ile Gln Gly Leu Asn Asp Ser Leu Ile Asp Leu Glu
    530                 535                 540

Thr Leu Ser Ile Leu Lys Thr Tyr Ile Lys Trp Pro Trp Tyr Val Trp
545                 550                 555                 560

Leu Ala Ile Ala Phe Ala Thr Ile Ile Phe Ile Leu Ile Leu Gly Trp
                565                 570                 575

Leu Phe Phe Met Thr Gly Cys Cys Gly Cys Cys Cys Gly Cys Phe Gly
                580                 585                 590

Ile Ile Pro Leu Met Ser Lys Cys Gly Lys Lys Ser Ser Tyr Tyr Thr
            595                 600                 605

Thr Phe Asp Asn Asp Val Val Thr Glu Gln Tyr Arg Pro Lys Lys Ser
    610                 615                 620

Val
625

<210> SEQ ID NO 6
<211> LENGTH: 546
<212> TYPE: PRT
<213> ORGANISM: Infectious Bronchitis Virus

<400> SEQUENCE: 6

Met Leu Val Lys Ser Leu Phe Leu Val Thr Ile Leu Phe Ala Leu Cys
1               5                   10                  15

Ser Ala Asn Leu Tyr Asp Asn Glu Ser Phe Val Tyr Tyr Tyr Gln Ser
            20                  25                  30

Ala Phe Arg Pro Gly His Gly Trp His Leu His Gly Gly Ala Tyr Ala
        35                  40                  45

Val Val Asn Val Ser Ser Glu Asn Asn Asn Ala Gly Thr Ala Pro Ser
    50                  55                  60

Cys Thr Ala Gly Ala Ile Gly Tyr Ser Lys Asn Leu Ser Ala Ala Ser
65                  70                  75                  80

Val Ala Met Thr Ala Pro Leu Ser Gly Met Ser Trp Ser Ala Asn Ser
                85                  90                  95

Phe Cys Thr Ala His Cys Asn Phe Thr Ser Tyr Ile Val Phe Val Thr
            100                 105                 110

His Cys Tyr Lys Ser Gly Ser Asn Ser Cys Pro Leu Thr Gly Leu Ile
        115                 120                 125

Pro Ser Gly Tyr Ile Arg Ile Ala Ala Met Lys His Gly Ser Ala Met
    130                 135                 140

Pro Gly His Leu Phe Tyr Asn Leu Thr Val Ser Val Thr Lys Tyr Pro
145                 150                 155                 160

Lys Phe Arg Ser Leu Gln Cys Val Asn Asn His Thr Ser Val Tyr Leu
                165                 170                 175

Asn Gly Asp Leu Val Phe Thr Ser Asn Tyr Thr Glu Asp Val Val Ala
            180                 185                 190

Ala Gly Val His Phe Lys Ser Gly Gly Pro Ile Thr Tyr Lys Val Met
        195                 200                 205

Arg Glu Val Lys Ser Leu Ala Tyr Phe Val Asn Gly Thr Ala His Asp
    210                 215                 220

Val Ile Leu Cys Asp Asp Thr Pro Arg Gly Leu Leu Ala Cys Gln Tyr
225                 230                 235                 240

Asn Thr Gly Asn Phe Ser Asp Gly Phe Tyr Pro Phe Thr Asn Thr Ser
```

```
                        245                 250                 255
Ile Val Lys Asp Lys Phe Ile Val Tyr Arg Glu Ser Ser Val Asn Thr
            260                 265                 270

Thr Leu Thr Leu Thr Asn Phe Thr Phe Ser Asn Glu Ser Gly Ala Pro
        275                 280                 285

Pro Asn Thr Gly Gly Val Asp Ser Phe Ile Leu Tyr Gln Thr Gln Thr
    290                 295                 300

Ala Gln Ser Gly Tyr Tyr Asn Phe Asn Phe Ser Phe Leu Ser Ser Phe
305                 310                 315                 320

Val Tyr Arg Glu Ser Tyr Tyr Met Tyr Gly Ser Tyr His Pro Arg Cys
            325                 330                 335

Ser Phe Arg Pro Glu Thr Leu Asn Asn Gly Leu Trp Phe Asn Ser Leu
            340                 345                 350

Ser Val Ser Leu Thr Tyr Gly Pro Ile Gln Gly Gly Cys Lys Gln Ser
            355                 360                 365

Val Phe Asn Gly Lys Ala Thr Cys Cys Tyr Ala Tyr Ser Tyr Gly Gly
    370                 375                 380

Pro Arg Gly Cys Lys Gly Val Tyr Arg Gly Glu Leu Thr Gln His Phe
385                 390                 395                 400

Glu Cys Gly Leu Leu Val Tyr Val Thr Lys Ser Asp Gly Ser Arg Ile
            405                 410                 415

Gln Thr Ala Thr Gln Pro Pro Val Leu Thr Gln Asn Phe Tyr Asn Asn
            420                 425                 430

Ile Asn Leu Gly Lys Cys Val Asp Tyr Asn Ile Tyr Gly Arg Ile Gly
            435                 440                 445

Gln Gly Leu Ile Thr Asn Val Thr Asp Leu Ala Val Ser Tyr Asn Tyr
    450                 455                 460

Leu Ser Asp Ala Gly Leu Ala Ile Leu Asp Thr Ser Gly Ala Ile Asp
465                 470                 475                 480

Ile Phe Val Val Gln Gly Glu Tyr Gly Pro Asn Tyr Tyr Lys Val Asn
            485                 490                 495

Pro Cys Glu Asp Val Asn Gln Gln Phe Val Val Ser Gly Gly Lys Leu
            500                 505                 510

Val Gly Ile Leu Thr Ser Arg Asn Glu Thr Gly Ser Gln Leu Leu Glu
        515                 520                 525

Asn Gln Phe Tyr Ile Lys Ile Thr Asn Gly Thr Arg Arg Ser Arg Arg
    530                 535                 540

Ser Val
545
```

ADAPTATION OF ATTENUATED INFECTIOUS BRONCHITIS VIRUS (IBV) TO EMBRYONIC KIDNEY CELLS AND VACCINE THEREBY PRODUCED

CROSS-REFERENCE TO RELATED APPLICATIONS

The present application is a continuation of U.S. application Ser. No. 14/887,965, filed on Oct. 20, 2015, which claims the benefit of priority under 35 U.S.C. § 119(e) to U.S. Provisional Applications No. 62/066,135, filed on Oct. 20, 2014, the contents of which re incorporated herein by reference in their entireties.

BACKGROUND

The field of the present invention relates to infectious bronchitis virus (IBV) and methods for passaging IBV. The disclosed methods may be utilized to prepare vaccine compositions comprising the passaged IBV.

In the poultry industry avian infectious bronchitis (IB) coronavirus (IBV) continues to be the most common contributor to respiratory disease in chicken populations despite worldwide extensive vaccination with a multiplicity of type-specific vaccines. IBV replicates primarily in the upper respiratory tract causing respiratory disease in large chicken populations. IBV's surface (S) glycoprotein is post-translationally cleaved into a S1 subunit (~550 amino acids) and a S2 subunit (~600 amino acids) (Lai and Holmes, 2001). Like other coronaviruses, the S1 subunit of the S glycoprotein is responsible for viral attachment to cells and is important for host protective immune responses as it induces virus neutralizing-antibodies (Cavanagh, 1981, 1983, 1984; Cavanagh and Davis, 1986; Koch et al., 1990; Koch and Kant, 1990; Mockett et al., 1984). Because of the relevance of S1 for the first step of replication (i.e., attachment to cells) and immunological escape, the extensive variation exhibited by the S1 glycoprotein among IBV coronaviruses (Kusters et al., 1987; Kusters et al., 1989b) is likely the most relevant phenotypic characteristic for this virus's "adaptation" and evolutionary success (Toro et al., 2012b). Genetic diversity among coronaviruses is achieved by high mutation frequency and recombination events (Enjuanes et al., 2000a; Enjuanes et al., 2000b; Lai and Cavanagh, 1997; Stadler et al., 2003). Selection acting on diverse populations results in rapid evolution of the virus and the emergence of antigenically different strains (Toro et al., 2012b). More than 30 different IBV types have been identified during the last 5 decades in the U.S. alone. According to a 2012 review, over 50 different genotypes of IBV are currently affecting chicken populations worldwide (Jackwood, 2012). Multiple recent surveillance studies performed in the U.S. have demonstrated that serotypes/genotypes Arkansas (Ark), Massachusetts (Mass), Connecticut (Conn), DE072, Georgia variants GAV and GA98 are currently the most prevalent (Jackwood et al., 2005; Nix et al., 2000; Toro et al., 2006).

Because IBV exists as multiple different serotypes that do not provide for cross-protection after host exposure, a multiplicity of serotype-specific IBV vaccines have been developed worldwide. For example, vaccination programs in the U.S. currently comprise mono- or polyvalent vaccines including Mass, Conn, GA98, DE072, and Ark serotypes. In Europe, IBV vaccines commonly include strains belonging to serotypes UK4/91, D274, and D-1466. However, IBV's high ability to evolve allows it to consistently circulate in commercial poultry and cause outbreaks of disease in spite of extensive vaccination. In addition, accumulating evidence indicates that attenuated IBV vaccines may also be contributing to the emergence and circulation of vaccine-like viruses in host populations (Toro et al., 2012b; Toro et al., 2012c). Indeed, viral sub-populations differing from the predominant live vaccine population have been shown to emerge during a single passage of attenuated IBV vaccine in chickens (McKinley et al., 2008; van Santen and Toro, 2008).

In an effort to understand the mechanisms underlying the emergence of vaccine-like viruses, S1 gene sequences of virus populations of all four commercially available IBV Ark-serotype attenuated vaccines were analyzed before and after replication in chickens (Gallardo et al., 2010; van Santen and Toro, 2008). The results from these analyses demonstrated different degrees of genetic heterogeneity among Ark-derived vaccines prior to inoculation into chickens, ranging from no apparent heterogeneity to heterogeneity in 20 positions in the S gene. In all except one position, nucleotide differences resulted in different amino acids encoded and therefore in phenotypic differences among subpopulations present in the vaccines. Significantly, it has been observed that specific minor subpopulations present in each of the vaccines were rapidly "selected" during a single passage in chickens. Indeed, by 3-days post-ocular vaccination, viral populations with S gene sequences distinct from the vaccine major consensus sequence at 5 to 11 codons were found to predominate in chickens (Gallardo et al., 2010; McKinley et al., 2008; van Santen and Toro, 2008). Thus, the use of attenuated coronavirus vaccines may be contributing to the problem of antigenic variation, and the development of a novel vaccine technology to increase the resistance of chicken populations to IBV and reduce economic losses is essential for the poultry industry.

SUMMARY

Disclosed are methods for preparing a vaccine against infection by infectious bronchitis virus (IBV). The methods typically include passing a heterogeneous attenuated population of IBV in chicken embryonic kidney cells, and optionally may include further passaging the heterogeneous attenuated population of IBV in embryonated chicken eggs (ECE) in order to obtain passaged attenuated population of IBV. Also disclosed are passaged attenuated populations of IBV in which the populations display a desired degree of homogeneity. Also disclosed are vaccines comprising the passaged attenuated populations of IBV, isolated viruses from the passaged attenuated populations of IBV, polypeptides of the passaged attenuated populations of IBV, vaccines thereof, and methods of vaccination comprising administering the disclosed vaccines.

The disclosed methods typically include passing a heterogeneous attenuated population of IBV in chicken embryonic kidney (CEK) cells, and optionally include passaging the heterogeneous attenuated population of IBV in ECE subsequent to passaging the heterogeneous attenuated population of IBV in CEK cells. The present inventor has determined that by passaging a heterogeneous attenuated population of IBV in CEK cells and adapting the heterogeneous attenuated population of IBV to growth in CEK cells, the heterogeneous attenuated population of IBV begins to adapt to growth in the CEK cells, and/or begin to exhibit increasing percentage of homogeneity at one or more nucleotide positions in genes of IBV including the gene for the S1 polypeptide after each passage in CEK cells, and/or begin to exhibit increasing percentage of homogeneity at one or more amino acid positions in polypeptides of IBV including the S1 polypeptide after each passage in CEK cells. As such, in the disclosed methods, the heterogeneous attenuated population of IBV may be passaged in CEK cells for a sufficient number of passages to obtain a population of IBV exhibiting a desired percentage of homogeneity at one or more amino acid positions in polypeptides of IBV including the S1 polypeptide and other polypeptides of IBV. The passaged attenuated population of IBV thus obtained by the disclosed methods, or any isolated virus or polypeptide of the passaged attenuated population of IBV, may be formulated as a vaccine. The vaccine then may be administered to subjects in need thereof in order to vaccinate the subjects against infection by IBV.

BRIEF DESCRIPTION OF THE DRAWINGS

FIG. 7. Histopathology scoring of tracheal (A) lymphocyte infiltration, (B) deciliation, and (C) mucosal necrosis in chickens treated as described in FIG. 6. Different letters indicate significant differences ($P<0.05$).

DETAILED DESCRIPTION

Figure 1:
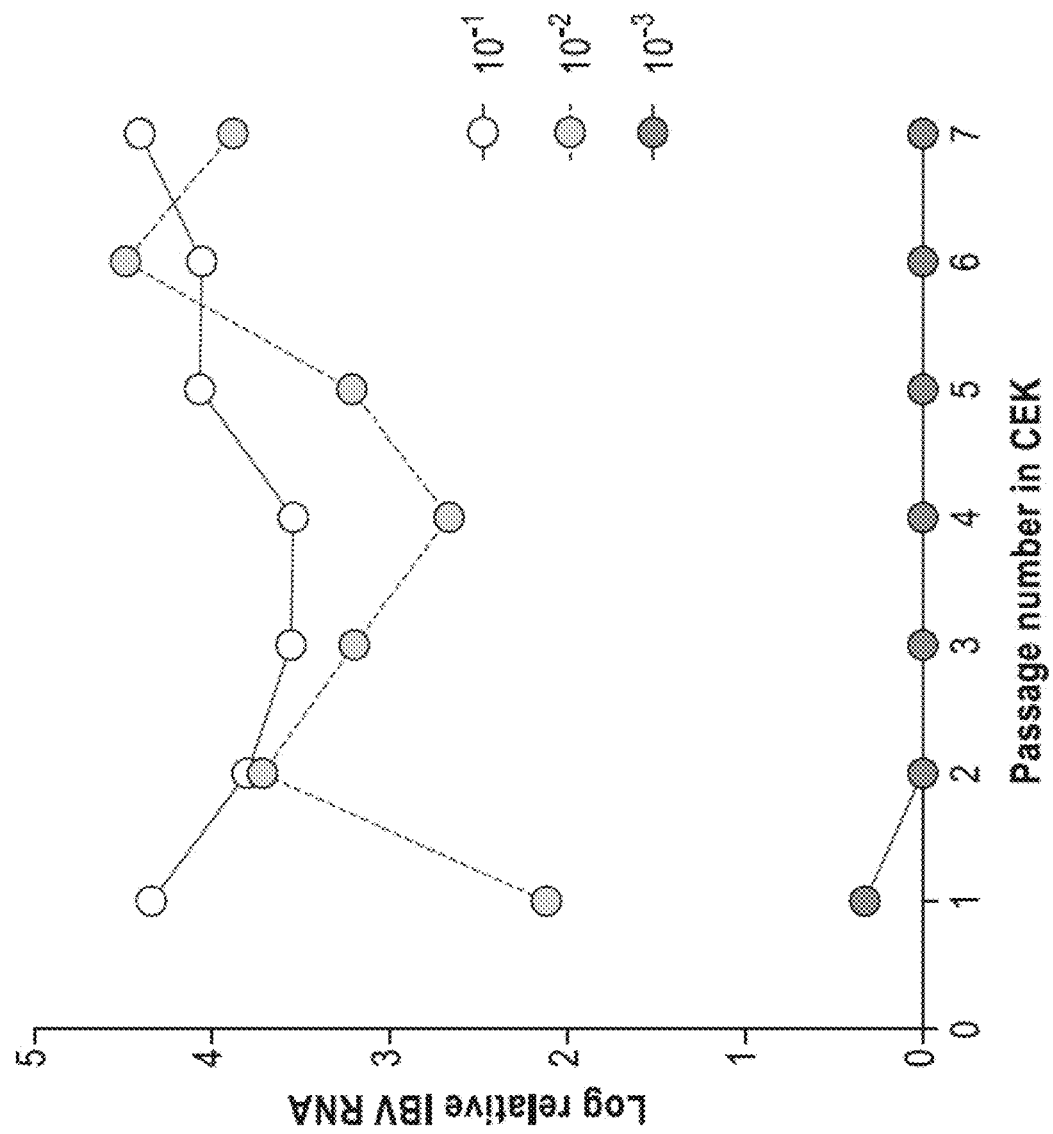
FIG. 1. IBV RNA detected by qRT-PCR of an embryo-attenuated ArkDPI-derived vaccine at different passage levels in chicken embryo kidney (CEK) cells. Cells were initially inoculated independently with tenfold serial dilutions indicated ($10^{-1}$ to $10^{-5}$) of the vaccine stock. No viral RNA was detected in cultures inoculated with the lower ($10^{-4}$; $10^{-5}$) initial virus concentrations used.

Disclosed herein are methods for passaging and propagating infectious bronchitis virus (IBV) and compositions, including vaccine compositions, comprising the passaged IBV. The disclosed methods and compositions may be described using several definitions as discussed below.

Unless otherwise specified or indicated by context, the terms "a", "an", and "the" mean "one or more." In addition, singular nouns such as "a population" should be interpreted to mean "one or more populations," unless otherwise specified or indicated by context.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus $\leq 10\%$ of the particular term and "substantially" and "significantly" will mean plus or minus $>10\%$ of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

As used herein, the terms "subject," "host," or "individual" typically refer to an avian at risk for acquiring an infection by infectious bronchitis virus (IBV). The terms "subject," "host," or "individual" may be used interchangeably. Suitable avians for the disclosed vaccines, compositions, and methods may include poultry such as members of the order Galliformes, and in particular the species *Gallus gallus* or the subspecies *Gallus gallus domesticus*.

As used herein "IBV" refers to "avian infectious bronchitis virus" which is a coronavirus that infects chicken and causes the associated disease "IB." The term "IBV" is meant to encompass numerous serotypes of IBV which have been isolated and characterized including but not limited to: B/D207/84; B/D274/84; B/UK167/84; B/UK142/86; E/D3896/84; E/UK123/82; Brazil/BR1/USP-73/09; 793B/4-91/91; FR/CR88121/88; China/Q1/98; China/LDL971/97 aaz09202; CAV/CAV9437/95; CAV/CAV1686/95; CAV/CAV56b/91; PA/Wolgemuth/98; PA/171/99; CA/557/03 S1; JAA/04 S1 vaccine; HN99 S1; N1/62/S1; GA08 S1 GU301925; Ark/ArkDPI/81 S1; Ark/Ark99/73; CAL99/CAL99/99 S1; CAL99/NE15172/95 S1; Holte/Holte/54; JMK/JMK/64; Gray/Gray/60; Iowa/Iowa609/56; Ca/1737/04 S1; DMA/5642/06 S1; GA07/GA07/07 S1; QX/QXIBV/

99; Mass/H52/S1; Mass/H120/S1; Mass/Mass41/41 S1; Conn/Conn46/51 S1 vaccine; FL/FL18288/71; DE/DE072/92 S1 vaccine; GA98/0470/98 S1; and Dutch/D1466/81.

The serotype of IBV is generally determined by a host's humoral immune response against the S1 polypeptide. Hence, the serotype of IBV is generally determined by the amino acid sequence of the S1 polypeptide. The amino acid sequence of the S1 polypeptide of Ark/ArkDPI/81 S1 is provided as SEQ ID NO:8.

The presently disclosed methods and composition may utilize naturally occurring avirulent strains of IBV. Alternatively, the presently disclosed vaccines, compositions, and methods may utilize live attenuated strains of IBV. Live attenuated strains of IBV are available commercially as vaccines and may include Ark/ArkDPI/81 S1. The complete genomic sequence of Ark/ArkDPI/81 has been reported. (See Ammayappan et al., Virology Journal 2008, 5:157, which is incorporated herein by reference in its entirety). The GenBank accession number for the Ark DPI genomic sequence is EU418976 and is provided herein as SEQ ID NO:1. The nucleotide sequence of the gene for the spike protein ("S") is provided herein as SEQ ID NO:2 and the amino acid sequence of the S protein is provided herein as SEQ ID NO:3. The amino acid sequence of the S1 protein is provided herein as SEQ ID NO:4 and the amino acid sequence of the S2 protein is provided herein as SEQ ID NO:5.

The complete genomes of the following strains are publicly available, for example from GenBank, under the succeeding accession number: TCoVMG10, NC_010800; Beaudette, NC_001451; M41, AY851295; CK/CH/LSD/05I, EU637854; A2, EU526388; LX4, AY338732; SAIBK, DQ288927. The sequences for various structural genes are publicly available, for example from GenBank, under the succeeding accession numbers: (a) for the complete structural genes: HK, AY761141; Vic, DQ490221; KB8523, M21515; TW2296/95, DQ646404; (b) for S1: Jilin, AY839144; Gray, L18989; Conn, EU526403; Holte, L18988; UK/2/91, Z83976; Qu16, AF349620; JMK, L14070; H120, M21970; GAV-92, AF094817; DE072, AF274435; IS/1366, EU350550; (c) for S2: JMK, AF239982; Jilin, AY839146; Holte, AF334685; DE072, AY024337; Conn, AF094818; Gray, AF394180; H120, AF239981; (d) for S: Ark 99, L10384; CU-T2, U04739; (e) for gene 3: Jilin, AY846833; Conn, AY942752; CU-T2, U46036; Ark 99, AY942751; Gray, AF318282 (f) for M: Jilin, AY846833; JMK, AF363608; Conn, AY942741; H120, AY028295; Gray, AF363607; (g) for gene 5: Jilin, AY839142; Gray, AF469011; Conn, AF469013; DE072, AF203000; and (h) for N: Jilin, AY839145.

As used herein, "viral load" is the amount of virus present in a sample from a subject infected with the virus. Viral load is also referred to as viral titer or viremia. Viral load can be measured in variety of standard ways including copy Equivalents of the viral RNA (vRNA) genome per milliliter individual sample (vRNA copy Eq/ml). This quantity may be determined by standard methods that include RT-PCR.

The terms "polynucleotide," "nucleic acid" and "nucleic acid sequence" refer to a polymer of DNA or RNA nucleotide of genomic or synthetic origin (which may be single-stranded or double-stranded and may represent the sense or the antisense strand). The polynucleotides contemplated herein may encode and may be utilized to express one or more IBV polypeptides.

As used herein, polypeptide, proteins, and peptides comprise polymers of amino acids, otherwise referred to as "amino acid sequences." As used herein, the term "amino acid sequence" refers to a polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. A polypeptide or protein is typically of length ≥100 amino acids (Garrett & Grisham, Biochemistry, $2^{nd}$ edition, 1999, Brooks/Cole, 110). A peptide is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110). However, the terms "polypeptide," "protein," and "peptide" may be used interchangeably herein.

The amino acid sequences disclosed and contemplated herein may include "substitutions" related to a reference amino acid sequence. As used herein, a "substitution" means replacement of one or more amino acids at one or more positions in a reference amino acid sequence with a different amino acid at the one or more positions.

The words "insertion" and "addition" refer to changes in an amino acid sequence resulting in the addition of one or more amino acid residues. For example, an insertion or addition may refer to 1, 2, 3, 4, 5, 10, 20, 30, 40, 50, 60, 70, 80, 90, 100, 150, or 200 amino acid residues.

A "deletion" refers to a change in the amino acid or nucleotide sequence that results in the absence of one or more amino acid residues. For example, a deletion may remove at least 1, 2, 3, 4, 5, 10, 20, 50, 100, or 200 amino acids residues. A deletion may include an internal deletion or a terminal deletion (e.g., an N-terminal truncation or a C-terminal truncation of a reference polypeptide).

A "fragment" is a portion of an amino acid sequence which is identical in sequence to but shorter in length than a reference sequence. A "fragment" as contemplated herein refers to a contiguous portion of an amino acid reference sequence. For example, a fragment of a polypeptide refers to less than a full-length amino acid sequence of the polypeptide (e.g., where the polypeptide is truncated at the N-terminus, the C-terminus, or both termini). A fragment may comprise up to the entire length of the reference sequence, minus at least one amino acid residue. For example, a fragment may comprise from 5 to 1000 contiguous amino acid residues of a reference polypeptide. In some embodiments, a fragment may comprise at least 5, 10, 15, 20, 25, 30, 40, 50, 60, 70, 80, 90, 100, 150, 250, or 500 contiguous amino acid residues of a reference polypeptide, respectively. Fragments may be preferentially selected from certain regions of a molecule. The term "at least a fragment" encompasses the full length polypeptide. An "immunogenic fragment" of a polypeptide is a fragment of a polypeptide typically at least 5 or 10 amino acids in length that includes one or more epitopes of the full-length polypeptide.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "variant," "mutant," or "derivative" of a particular polypeptide sequence is defined as a polypeptide sequence having at least 50% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides. A "variant" or a "derivative" may have substantially the same functional activity as a reference polypeptide. For example, a variant or derivative of the IBV S1 polypeptide may have one or more functional activities associated with the wild-type IBV S1 polypeptide including, but not limited to, interacting with the S2 polypeptide, interacting with the viral membrane of IBV, and/or facilitating fusion of IBV with a host cell membrane.

As disclosed herein, "passaging" refers to the process of growing viruses in a suitable host (e.g., CEK cells and/or ECE). Passaging encompasses serial passaging whereby a population of IBV (e.g., a heterogeneous population of IBV) is inoculated at a selected concentration into a first environment (e.g., fresh CEK cells), and after being allowed to grow for a period of time, a sample of the population of IBV is removed, optionally diluted (e.g., ten-fold) and inoculated at a selected concentration into a second environment (e.g. fresh CEK cells and/or ECE).

Formulation of the Vaccine Compositions

The compositions disclosed herein may be formulated as vaccine compositions for inducing an immune response against IBV. Vaccines, compositions, and methods for immunizing against infection by IBV are disclosed in U.S. Published Application No. 2014/0141043, the content of which is incorporated herein by reference in its entirety. As used herein, an "immune response" may include an antibody response (i.e., a humoral response), where an immunized individual is induced to produce antibodies against an administered antigen (e.g., IgY, IgA, IgM, IgG, or other antibody isotypes) and may also include a cell-mediated response, for example, a cytotoxic T-cell response against cells expressing foreign peptides derived from an administered antigen in the context of a major histocompatibility complex (MHC) class I molecule.

As used herein, "potentiating" or "enhancing" an immune response means increasing the magnitude and/or the breadth of the immune response. For example, the number of cells that recognize a particular epitope may be increased ("magnitude") and/or the numbers of epitopes that are recognized may be increased ("breadth").

The compositions disclosed herein may be formulated as vaccine compositions for administration to a subject in need thereof. Such compositions can be formulated and/or administered in dosages and by techniques well known to those skilled in the medical arts taking into consideration such factors as the age, sex, weight, and condition of the particular subject and the route of administration. The compositions may include carriers, diluents, or excipients as known in the art. Further, the compositions may include preservatives (e.g., anti-microbial or anti-bacterial agents such as benzalkonium chloride) or adjuvants.

A "vaccine" is defined herein in its broad sense to refer to any type of biological agent in an administrable form capable of stimulating a protective immune response in an animal inoculated with the vaccine. For purposes of this invention, the vaccine may comprise a passaged attenuated population of IBV.

The compositions may be administered prophylactically. In prophylactic administration, the vaccines may be administered in an amount sufficient to induce immune responses for protecting against IBV infection (i.e., a "vaccination effective dose" or a "prophylactically effective dose").

The composition disclosed herein may be formulated for delivered via a variety of routes. Routes may include, but are not limited to, parenteral administration (e.g., intradermal, intramuscular or subcutaneous delivery), aerosol administration (e.g., using spray cabinets), oral administration, and intraocular administration.

Adjuvants

The disclosed compositions may include an adjuvant. The term "adjuvant" refers to a compound or mixture that enhances the immune response to an antigen. An adjuvant can serve as a tissue depot that slowly releases the antigen and also as a lymphoid system activator that non-specifically enhances the immune response. Examples of adjuvants which may be employed include MPL-TDM adjuvant (monophosphoryl Lipid A/synthetic trehalose dicorynomycolate, e.g., available from GSK Biologics). Another suitable adjuvant is the immunostimulatory adjuvant AS021/AS02 (GSK). These immunostimulatory adjuvants are formulated to give a strong T cell response and include QS-21, a saponin from *Quillay saponaria*, the TL4 ligand, a monophosphoryl lipid A, together in a lipid or liposomal carrier. Other adjuvants include, but are not limited to, nonionic block co-polymer adjuvants (e.g., CRL1005), aluminum phosphates (e.g., AlPO$_4$), R-848 (a Th1-like adjuvant), imiquimod, PAM3CYS, poly (I:C), loxoribine, potentially useful human adjuvants such as BCG (bacille Calmette-Guerin) and *Corynebacterium parvum*, CpG oligodeoxynucleotides (ODN), cholera toxin derived antigens (e.g., CTA1-DD), lipopolysaccharide adjuvants, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions in water (e.g., MF59 available from Novartis Vaccines or Montanide ISA 720), keyhole limpet hemocyanins, and dinitrophenol.

Prime-Boost Vaccination Regimen

As used herein, a "prime-boost vaccination regimen" refers to a regimen in which a subject is administered a first composition one or more times (e.g., two or three times with about 2, 3, or 4 weeks between administrations) and then after a determined period of time (e.g., about 1 week, about 2 weeks, about 4 weeks, about 2 months, about 3 months, about 4 months, about 5 months, about 6 months, or longer), the subject is administered a second composition. The second composition may also be administered more than once, with at least 2, 3, or 4 weeks between administrations. The first and second compositions may be the same or different. For example, the first composition may include a recombinant viral vector and the second composition may include a live, attenuated virus.

Characterization of the Immune Response and Protection in Vaccinated Subjects

The immune response and protection in vaccinated subjects may be evaluated as described herein (e.g., as described in the Examples below) and/or as know in the art. For example, the vaccine compositions disclosed herein may be delivered to subjects at risk for infection with IBV. Subsequently, the efficacy of the vaccine may be assessed based on the immune response induced by administering the vaccine. In order to assess the efficacy of the vaccine, the immune response can be assessed by measuring the induction of antibodies to an antigen or particular epitopes of an antigen or by measuring a T-cell response to an antigen or particular epitopes of an antigen. Antibody responses may be measured by assays known in the art such as ELISA. T-cell responses may be measured, for example, by using tetramer staining of fresh or cultured PBMC, ELISPOT assays or by using functional cytotoxicity assays, which are well-known to those of skill in the art.

Protection against challenge may be evaluated after challenge by clinical signs, viral load, and tracheal histopathology. Respiratory rales (nasal and/or tracheal) may be evaluated blindly by close listening to each challenged subject (e.g., a bird) and scoring as 0 (absent), 1 (mild), 2 (moderate), or 3 (severe). Viral load in tears may be determined by qRT-PCR. Tracheal histopathology may be evaluated and histomorphometry may be performed essentially. Necrosis and deciliation in the tracheal mucosa may be evaluated blindly and scored 1 through 5 based on severity (i.e., normal, mild, moderate, marked, severe). Histomorphometry may be performed on a single digitally photographed microscopic field (200× magnification) containing a representative longitudinal section of the cranial one-third of the tracheal mucosa and the supporting cartilage ring.

Illustrative Embodiments

The following embodiments are illustrative and are not intended to limit the claimed subject matter.

Embodiment 1. A method for preparing a vaccine against infection by infectious bronchitis virus (IBV), the method comprising passing a heterogeneous attenuated population of IBV in chicken embryonic kidney (CEK) cells.

Embodiment 2. The method of embodiment 1, wherein the heterogeneous attenuated population of IBV is passaged for a sufficient number of passages wherein at least about 95%, 96%, 97%, 98%, 99%, or 100% of the passaged attenuated population of IBV exhibits homogeneity at one or more nucleotide positions in the gene for the S1 polypeptide after the sufficient number of passages, and/or wherein at least about 95%, 96%, 97%, 98%, 99%, or 100% of the passaged attenuated population of IBV exhibits homogeneity at one or more amino acid positions in the S1 polypeptide after the sufficient number of passages.

Embodiment 3. The method of any of the foregoing embodiments, wherein the one or more amino acids comprise an amino acid selected from the group consisting of Ser at amino acid position 213 of the S1 polypeptide, Arg at amino acid position 323 of the S1 polypeptide, Arg at amino acid position 386 of the S1 polypeptide, Gln at amino acid position 398 of the S1 polypeptide, and His at amino acid position 399 of the S1 polypeptide, and any combination thereof.

Embodiment 4. The method of any of the foregoing embodiments, wherein the one or more amino acids comprise Ser at amino acid position 213 of the S1 polypeptide.

Embodiment 5. The method of any of the foregoing embodiments, wherein at least about 95%, 96%, 97%, 98%, 99%, or 100% of the passaged attenuated population of IBV further exhibits homogeneity at one or more amino acid positions in a polypeptide selected from the group consisting of NSP2 (e.g., Val at genome position 1097; Phe at genome position 1107; Asn at genome position 2488), NSP3 (e.g., Asp at genome position 4256), NSP14 (e.g., Lys at genome position 17,550, and S2.

Embodiment 6. The method of any of the foregoing embodiments, wherein the heterogeneous attenuated population of IBV comprises a strain of IBV selected from the group consisting of B/D207/84; B/D274/84; B/UK167/84; B/UK142/86; E/D3896/84; E/UK123/82; Brazil/BR1/USP-73/09; 793B/4-91/91; FR/CR88121/88; China/Q1/98; China/LDL971/97 aaz09202; CAV/CAV9437/95; CAV/CAV1686/95; CAV/CAV56b/91; PA/Wolgemuth/98; PA/171/99; CA/557/03 S1; JAA/04 S1 vaccine; HN99 S1; N1/62/S1; GA08 S1 GU301925; Ark/ArkDPI/81 S1; Ark/Ark99/73; PP14/PP13/??; CAL99/CAL99/99 S1; CAL99/NE15172/95 S1; Holte/Holte/54; JMK/JMK/64; Gray/Gray/60; Iowa/Iowa609/56; Ca/1737/04 S1; DMA/5642/06 S1; GA07/GA07/07 S1; QX/QXIBV/99; Mass/H52/S1; Mass/H120/S1; Mass/Mass41/41 S1; Conn/Conn46/51 S1 vaccine; FL/FL18288/71; DE/DE072/92 S1 vaccine; GA98/0470/98 S1; and Dutch/D1466/81.

Embodiment 7. The method of any of the foregoing embodiments, wherein the heterogeneous attenuated population of IBV is Ark/ArkDPI/81 S1.

Embodiment 8. The method of any of the foregoing embodiments, wherein the heterogeneous attenuated population of IBV is passaged in chicken embryonic kidney cells for at least 3 passages.

Embodiment 9. The method of any of the foregoing embodiments, wherein the heterogeneous attenuated population of IBV is passaged in chicken embryonic kidney cells for at least 5 passages.

Embodiment 10. The method of any of the foregoing embodiments, wherein the heterogeneous attenuated population of IBV is passaged in chicken embryonic kidney cells for at least 7 passages.

Embodiment 11. The method of any of the foregoing embodiments, wherein after the heterogeneous attenuated population of IBV is passaged in chicken embryonic kidney cells, the passaged attenuated population of IBV is further passaged in embryonated chicken eggs (ECE).

Embodiment 12. The method of any of the foregoing embodiments, further comprising formulating the passaged attenuated population of IBV as a vaccine by adding a carrier or excipient to the passaged attenuated population of IBV.

Embodiment 13. A vaccine comprising a passaged attenuated population of IBV and a suitable carrier or excipient, wherein at least about 95%, 96%, 97%, 98%, 99%, or 100% of the passaged attenuated population of IBV exhibits homogeneity at one or more amino acid positions in the S1 polypeptide selected from the group consisting of Ser at amino acid position 213 of the S1 polypeptide, Arg at amino acid position 323 of the S1 polypeptide, Arg at amino acid position 386 of the S1 polypeptide, Gln at amino acid position 398 of the S1 polypeptide, His at amino acid position 399 of the S1 polypeptide, and any combination thereof.

Embodiment 14. The vaccine of embodiment 13, wherein at least about 95%, 96%, 97%, 98%, 99%, or 100% of the passaged attenuated population of IBV comprises Ser at amino acid position 213 of the S1 polypeptide.

Embodiment 15. The vaccine of embodiment 13 or 14, wherein at least about 95%, 96%, 97%, 98%, 99%, or 100% of the passaged attenuated population of IBV comprises Ser at amino acid position 213 of the S1 polypeptide; Arg at amino acid position 323 of the S1 polypeptide; Arg at amino acid position 386 of the S1 polypeptide, Gln at amino acid position 398 of the S1 polypeptide, and His at amino acid position 399 of the S1 polypeptide, and optionally, wherein at least about 95%, 96%, 97%, 98%, 99%, or 100% of the passaged attenuated population of IBV comprises an S1 polypeptide comprising the amino acid sequence of SEQ ID NO:6, or a variant or mutant thereof.

Embodiment 16. The vaccine of embodiment 15, wherein at least about 95%, 96%, 97%, 98%, 99%, or 100% of the passaged attenuated population further exhibits homogeneity at one or more amino acid positions in a polypeptide selected from NSP2, NSP3, NSP14, and S2.

Embodiment 17. A method for vaccinating a subject against infection by IBV, the method comprising administering to the subject the vaccine of embodiment 13.

Embodiment 18. The method of embodiment 17, wherein the vaccine comprises an effective amount of the passaged attenuated population of IBV for inducing an immune response against S1 polypeptide.

Embodiment 19. The method of embodiment 18, wherein the immune response is an antibody response.

Embodiment 20. The method of any of embodiments 17-19, wherein the vaccine is administered comprising in a prime/boost regimen.

Embodiment 21. A vaccine comprising a polypeptide comprising the amino acid sequence of SEQ ID NO:6, or a variant or mutant thereof, together with a suitable carrier or excipient.

Embodiment 22. A method for vaccinating a subject in need thereof against infection by IBV, the method comprising administering the vaccine of embodiment 21 to the subject.

Embodiment 23. An isolated virus obtained from passing a heterogeneous attenuated population of IBV in chicken embryonic kidney (CEK) cells, optionally back-passaging the passaged attenuated population in embryonated chicken eggs (ECE), and isolating a virus from the passaged attenuated population.

Embodiment 24. A vaccine comprising the isolated virus of embodiment 23, together with a suitable carrier or excipient.

Embodiment 25. A method for vaccinating a subject in need thereof against infection by IBV, the method comprising administering the vaccine of embodiment 24 to the subject.

EXAMPLES

The following examples are illustrative and are not intended to limit the claimed subject matter.

Example 1

Effects of Adaptation of Infectious Bronchitis Virus Arkansas Attenuated Vaccine to Embryonic Kidney Cells Reference is made to Ghetas et al., "Effects of Adaptation of Infectious Bronchitis Virus Arkansas Attenuated Vaccine to Embryonic Kidney Cells," Avian Diseases 59:106-113, 2015, published ahead of print on Dec. 11, 2014, the content of which is incorporated herein by reference in its entirety.

Abbreviations

ANOVA=analysis of variance; Ark=Arkansas; CEK=chicken embryo kidney; CEKp7=CEK passage 7; CPE=cytopathogenic effect; DPI=Delmarva Poultry Industry; ECE=embryonated chicken egg; ELISA=enzyme-linked immunosorbent assay; IBV=infectious bronchitis virus; RT-PCR=reverse transcriptase polymerase chain reaction; qRT-PCR=quantitative RT-PCR; S=spike protein; S/P ratio=sample to positive ratio; EID50=50% embryo infectious dose; amino acid=aa; nucleotide=nt; N=nucleocapsid protein; NSP=Nonstructural protein; UTR=untranslated region.

Summary

The population structure of an embryo-attenuated infectious bronchitis virus (IBV) Arkansas (Ark) Delmarva Poultry Industry (DPI)-derived vaccine was characterized during serial passages in chicken embryo kidney (CEK) cells and after back-passage in embryonated chicken eggs (ECE) and in chickens. Both conventional and deep sequencing results consistently showed population changes occurred during adaptation to CEK cells. Specifically, thirteen amino acid (aa) positions seemed to be targets of selection when comparing the vaccine genome prior to and after 7 passages in CEK (CEKp7). Amino acid changes occurred at four positions in the S gene, and at two positions in the S gene large shifts in frequencies of aa encoded were observed. CEK adaptation shifted the virus population towards homogeneity in S. The changes achieved in the S1 gene in CEKp7 were maintained after a backpassage in ECE. Outside the S gene, amino acid changes at three positions and large shifts in frequencies at four positions were observed. Synonymous nucleotide changes and changes in non-coding regions of the genome were observed at eight genome positions. Inoculation of early CEK passages into chickens induced higher antibody levels and CEKp4 induced increased respiratory signs compared to CEKp7. From an applied perspective, the fact that CEK adaptation of embryo-attenuated Ark vaccines reduces population heterogeneity and that changes do not revert after one replication cycle in ECE or in chickens provides an opportunity to improve commercial ArkDPI-derived vaccines.

Abundant epidemiological information indicates that most infectious bronchitis virus (IBV) outbreaks of respiratory disease during the last decade in the U.S. have been caused by Arkansas (Ark)-type strains in spite of extensive vaccination with Ark Delmarva Poultry Industry (ArkDPI)-derived vaccines (17, 27, 35). We and others have reported that commercially available Ark serotype IBV vaccines exhibit heterogeneity in the structure of their viral population despite being derived from the same ArkDPI isolate. The high number of Ark-like viruses obtained from Ark-vaccinated chickens suggests not only that these attenuated vaccines provide inadequate protection, but also that they may themselves be contributing to the problem.

The 5' two-thirds of the single-stranded positive-sense RNA IBV genome of ≥27 kb encode 15 non-structural proteins (NSP) including the RNA-dependent RNA polymerase. The remainder of the genome encodes four structural proteins including the spike (S), envelope, membrane, and nucleocapsid (N) proteins (6, 11, 12). S is post-translationally cleaved into the S1 and S2 subunits. S1 of ~550 amino acids (aa) constitutes the bulbous end, and S2 of ~620 aa forms the stalk anchoring S to the envelope (22). The role of S1 in viral attachment to cells and determining the species- and tissue/cell tropism of several corona viruses, including IBV, has been reported extensively [e.g. (3-5, 13, 14, 16, 24)]. The S1 subunit is important for host protective immune responses as it induces virus neutralizing-antibodies (7, 8, 18). Thus, the extensive variation among IBV populations exhibited by the S1 protein is relevant for immunological escape (9, 19, 20). IBV evolves by natural selection, i.e. generation of genetic diversity by high mutation frequency and recombination events followed by selection acting on diverse phenotypes (32). Earlier work showed that during adaptation of the chicken embryo-adapted IBV Beaudette strain to Vero cells a total of 49 aa changes took place. The majority of these aa substitutions (53%) were concentrated in the S protein (13). During attenuation of IBV ArkDPI by passages in embryonated chicken eggs (ECE) 17 aa changes occurred, with most located in the replicase 1a and S regions, again with changes in the S gene overrepresented (1). Based on S1 gene sequences, we previously identified five distinct virus subpopulations in ArkDPI-derived vaccines that became rapidly positively selected in the chicken upper respiratory tract, whereas the predominant IBV phenotype contained in the embryo-attenuated vaccines was negatively selected (15, 38). Differences in frequencies of phenotypes within IBV populations are associated with differences in the behavior of these viruses in the host (26). From an applied perspective, genetic and phenotypic shifts occurring in Ark-type IBV vaccine populations during replication in chickens are most likely responsible for the emergence of Ark-like viruses in the U.S. poultry industry.

In this study, we investigated genetic and phenotypic changes associated with adaptation of an attenuated IBV ArkDPI-derived vaccine to chicken embryo kidney (CEK) cells. We also evaluated the effects of back-passage of CEK-adapted Ark virus both in chickens and ECE.

Materials and Methods

Chickens and ECE. White-leghorn specific pathogen free (SPF) ECE (Sunrise Farms, Catskill, N.Y.) and SPF chickens hatched from them were used in all experiments. Animal experimental procedures and care were performed in biosafety level 2 facilities at Auburn University College of Veterinary Medicine in compliance with all applicable federal and institutional animal use guidelines. Auburn University College of Veterinary Medicine is an Association for Assessment and Accreditation of Laboratory Animal Care-accredited institution.

CEK Cell Cultures. Primary CEK cell cultures were prepared as described (30). In brief, kidneys were obtained from 17-20 day-old SPF chicken embryos. After trypsinization, cells were washed with phosphate buffer saline, centrifuged, and resuspended in minimal essential medium containing 10% fetal bovine serum. Cells were placed in 24-well tissue culture plates and incubated at 37° C. and 5% $CO_2$.

IBV Passage in CEK. A commercially available single-entity attenuated IBV ArkDPI-derived vaccine was used. The chosen Ark-type vaccine, previously coded as vaccine B, shows a wider variety of subpopulations selected in chickens than other Ark-type vaccines (15, 38). The lyophilized vaccine was reconstituted in sterile tryptose broth and titrated in 9-day-old embryonated chicken eggs as accepted (39). Tenfold dilutions from $10^{-1}$ through $10^{-5}$ were prepared from the vaccine suspension containing $10^{5.5}$ egg infectious doses 50%/100 μl and each dilution independently inoculated in CEK cultures by adding 25 μl of virus suspension to 500 μl cell culture suspension in each well (4 wells per dilution). Viruses in cell cultures were serially passaged every 48 hours. For each passage cells were harvested, pooled for each initial concentration of inoculum, subjected to 3 cycles of freezing and thawing, cell debris removed by low-speed centrifugation, and 100 μl of the supernatant used in the subsequent passage. This supernatant obtained from the freeze-thaw lysates is further referred to as culture supernatant. The remaining culture supernatant was stored at −80° C. until use for inoculation in chickens.

Effect of CEK-adapted IBV in Chickens. Fifty-three 5-day-old chickens, divided into 4 groups (n=12/group) and an uninoculated control group (n=5) were maintained in Horsfall-type isolators. Chickens in groups 1, 2, 3, and 4 were inoculated ocularly with 100 μl of culture supernatant of IBV Ark vaccine CEK passages 1, 3, 4, and 7 respectively. Five days postinoculation respiratory signs were blindly scored [O (negative), 1 (mild), 2 (moderate), 3 (severe)] for all chickens individually. On the same day tear fluids were collected as described (33) for IBV RNA detection by reverse transcriptase polymerase chain reaction (RT-PCR). Finally, serum samples were collected 18 and 27 days after inoculation and IBV specific antibodies determined by ELISA (Idexx Laboratories. Inc., Westbrook, Me.) using a 1:100 serum dilution. Data obtained from all groups were compared by analysis of variance (ANOV A) and multiple comparisons post-tests.

CEK-adapted IBV Back-passage in ECE. 0.1 ml of culture supernatant from each IBV CEK passage 1, 3, 4, and 7 were inoculated in 9 day-old ECE (n=2/group). Allantoic fluids were harvested 72 hours after inoculation, centrifuged, and stored at −80° C. until RNA extraction for IBV genome sequencing.

IBV RNA Extraction and RT-PCR. IBV RNA was extracted from IBV CEK cell culture passages, tear samples collected from individual chickens, and from allantoic fluids (described above) using the Qiagen QIAmp viral RNA mini kit (Qiagen, Valencia, Calif.) following the manufacturer's protocol. RT-PCR was carried out using the Qiagen one-step RT-PCR kit. Primers NEWS1OLIGO5' (10) and S1OLIGO3' (21) were used to amplify the S1 gene of IBV from CEK passages, from allantoic fluids, and tear samples. Primers S17F and S18R (15) and S2F (38) and S1OLIGO3' were also used to amplify portions of the IBV S1 gene from tear samples. RT-PCR products were visualized by gel green stain (Phoenix Research, Candler, N.C.) after agarose gel electrophoresis.

Sequencing of cDNA Generated by RT-PCR. The amplified cDNA was purified using the QIAquick PCR purification kit (Qiagen, Valencia, Calif.) and submitted to the Massachusetts General Hospital DNA core facility for sequencing using S1R, S2F (38), and S1OLIGO3' primers for cDNA amplified with primers NEWS1OOLIGO5", S1OLIGO3' from supernatants of CEK cell culture passages, allantoic fluids, and tear fluids; or S1R for cDNA amplified with S17F and S18R primers from tear samples. Sequences were aligned using Mac Vector 10.6.0 software (MacVector Inc., Cary, N.C.). All sequence chromatograms were examined to identify positions containing more than one peak indicating the presence of a mixed IBV population. The quantitative analysis of nucleotide peak heights in the chromatograms at heterogeneous positions was obtained after normalizing the height of major and minor peaks to peak heights obtained in samples with a single population.

Quantification of IBV RNA in CEK Cell Culture Supernatant by qRT-PCR. Viral RNA (5 μl) extracted from culture supernatant of each IBV CEK passage was used to determine relative IBV RNA concentration by fluorescence resonance energy transfer qRT-PCR. Primers and probes used amplified a portion of the Ark IBV N gene as previously described (36).

Sequence Analyses of Embryo-attenuated ArkDPI after CEK Adaptation by Deep Sequencing. RNA extracted from the IBV vaccine virus stock and from the virus after 7 passages in CEK (CEKp7) was subjected to next-generation sequencing. Because of heavy host cell nucleic acid contamination in the cell culture supernatant, the CEKp7 was replicated once in ECE prior to deep-sequencing. IBV RNA was extracted from allantoic fluid using TRI Reagent LS RNA Isolation Reagent (Molecular Research Center, Cincinnati, Ohio) according to the manufacturer's protocol and omitting the isopropanol precipitation step. RNA was further purified using the Qiagen RNeasy mini kit, following the RNA cleanup protocol. Purified RNA was submitted for next-generation Illumina Sequencing at HudsonAlpha (Huntsville, Ala.), (50 bp paired-end reads; 15 million reads). The resultant paired-end sequencing data were trimmed using CLC Genomics Workbench Software, using a trim setting (0.01) to achieve high quality sequences with low error probability. The trimmed sequences were then used for a reference assembly using the ArkDPI passage 101 genome (1) (Genbank accession# EU418975) as the reference genome using the default setting of 0.80 for sequence match. Single nucleotide polymorphism detection of nucleotides at >0.001% frequency was then performed on the reference assembly and analyzed using CLC Genomics Workbench.

Results

Virus Concentrations During Serial Passages in CEK Cells. Ten-fold serial dilutions (from $10^{-1}$ to $10^{-5}$) of an ArkDPI-derived IBV vaccine were initially inoculated into CEK cells to determine which virus concentration allowed the most successful replication and adaptation. A cytopathogenic effect (CPE) characterized by detachment of cells and formation of syncytia (not shown) was initially observed during the 2nd CEK passage and became more obvious during the $5^{th}$ passage in wells that had been inoculated with the higher vaccine virus concentrations ($10^{-1}$ and $10^{-2}$ dilutions). No CPE was observed in wells inoculated with higher ($10^{-3}$-$10^{-5}$) virus dilutions. IBV RNA was successfully amplified by qRT-PCR from cell cultures during all passages in wells inoculated with the $1^{st}$ and $2^{nd}$ tenfold dilutions (FIG. 1). In contrast, IBV RNA was only detected in the $1^{st}$ passage of the $3^{rd}$ tenfold dilution and not detected in cultures inoculated with the $4^{th}$ and $5^{th}$ tenfold dilutions. As seen in FIG. 1, IBV RNA levels declined from the $1^{st}$ or $2^{nd}$ through the $4^{th}$ passages and subsequently increased from the $5^{th}$ passage to reach maximal levels at the $7^{th}$ passage.

Genome Changes Detected During Adaptation to CEK Cells. The S1 gene sequence was determined for CEK cell IBV vaccine serial passages that allowed consistent IBV RNA amplification. In cells inoculated with the highest initial virus concentration changes were detected during serial passages at S1 aa positions 163, 323, 386, 398, and 399 (Table 1).

TABLE 1

S1 amino acid (aa) differences of IBV ArkDPI-derived embryo-attenuated vaccine during serial passages in CEK cells.

| | nt | | | | | |
|---|---|---|---|---|---|---|
| | 488 | 911 | 968 | 1157 | 1192 | 1195 |
| | aa | | | | | |
| | 163 | 304 | 323 | 386 | 398 | 399 |
| | Vaccine | | | | | |
| | R[1] | T | T(R) | R((H)) | E/Q | H((Y)) |
| A | | | | | | |
| CEK p1[2] | R(I)3 | T | T/R | R (L, H) | Q(E) | H((Y)) |
| CEK p2 | I(R) | T | R ((T)) | R ((L)) | Q | H |
| CEK p3 | I/R | T | R ((T)) | L/R((H)) | Q | H((Y)) |
| CEK p4 | I/R | T | R | L/R | Q | H |
| CEK p5 | I/R | T | R | L/R | Q | H |
| CEK p6 | I((R)) | T | R | R((L)) | Q | H |
| CEK p7 | I | T | R | R | Q | H |
| B | | | | | | |
| CEK p1 | R | T | R | R | Q | H |
| CEK p2 | R | T(I) | R | R | Q | H |
| CEK p3 | R | T/I | R | R | Q | H |
| CEK p4 | R | I((T)) | R | R | Q | H |
| CEK p5 | R | I((T)) | R | R | Q | H |
| CEK p6 | R | I | R | R | Q | H |
| CEK E7 | R | I | R | R | Q | H |

A = $10^{-1}$ initial dilution of vaccine stock;

B = $10^{-2}$ initial dilution used.

[1]Single letter aa code is used. Bold font used to facilitate identification of aa differing from vaccine.

[2]CEKp1-p7 = passage number in chicken embryonic kidney cells.

[3]Mixed populations inferred from double nucleotide peaks at some positions.

Quantitative analysis of chromatogram peak heights at these positions specified as follows: (( )) indicates minor peak <20%; ( ) minor 20% to 40%; / = minor 40% to 50%.

Changes were characterized by presence of mixed populations during early passages and establishment of a single population in passage 7, which was maintained after further passages (not shown). In the lower initial virus concentration ($10^{-2}$) aa changes during adaptation were observed at S1 aa positions 304, 323, 386, 398, and 399. Interestingly, changes at aa positions 163 and 304 during adaptation to CEK differed in the two passage series.

Further nucleotide and deduced aa changes within and outside the S gene resulting during ArkDPI adaptation to CEK cells were identified by next generation genome sequencing of the attenuated vaccine virus stock and CEKp7 obtained starting with the highest initial virus concentration. Large shifts in nucleotide frequencies in both protein coding regions (including both non-synonymous and synonymous changes) and non-protein coding regions were observed (Tables 2 and 3).

TABLE 2

Amino acid frequency differences 1 detected in non-structural (NSP) and spike (S) proteins of a commercial embryo-attenuated IBV ArkDPI-derived vaccine after 7 passages in chicken kidney cell cultures (CEKp7).

| Genome position | Protein | Major aa in vaccine | % | Minor aa in vaccine | % | Major aa in CEKp7 | % | Minor aa in CEK p7 | % |
|---|---|---|---|---|---|---|---|---|---|
| 1,097 | NSP2 | A | 92.4 | V | 7.6 | V | 94.9 | A | 5.0 |
| 1,107 | NSP2 | L | 78.7 | F | 21.3 | F | 96.4 | L | 3.5 |
| 2,488 | NSP2 | N[3] | 82.8 | H | 17.2 | N | 100 | — | <0.03 |
| 4,256 | NSP3 | G | 78.9 | D | 20.6 | D | 95.7 | G | 4.2 |
| 17,550 | NSP14 | K | 54.1 | Q | 45.9 | K | 100 | — | 0.01 |
| 17,641 | NSP14 | D | 100 | G | 0.03 | D | 87.0 | G | 13.0 |
| 20,798 | S1 (163)[2] | R | 97.7 | I | 2.3 | I | 97.2 | R | 2.8 |
| 20,947 | S1 (213) | S | 93.0 | A | 7.0 | S | 100 | — | <0.03 |
| 21,278 | S1 (323) | T | 73.4 | R | 26.2 | R | 99.9 | T | 0.03 |
| 21,467 | S1(386) | R | 90.1 | H | 7.5 | R | 97.2 | L | 2.8 |
| 21,502 | S1 (398) | E | 55.5 | Q | 44.5 | Q | 100 | — | <0.03 |
| 21,505 | S1 (399) | H | 93.8 | Y | 6.2 | H | 100 | — | <0.03 |
| 22,976 | S2 (889) | S | 100 | F/Y | 0.01 | F | 96.3 | S | 3.7 |
| 27,244 | ORF 6b | A | 100 | V | 0.04 | A | 84.5 | V | 15.5 |

[1] Only genome positions where nt frequencies change by >10% or minor codon >6% are shown.
[2] Numbers in parentheses indicate aa position in S.
[3] Bold font indicates aa predominant in CEKp7 to facilitate visual sizing proportion they were in vaccine.

TABLE 3

Synonymous nucleotide frequency differences and nucleotide frequency differences in non-protein-coding regions of a commercial embryo-attenuated IBV ArkDPI-derived vaccine after 7 passages in chicken kidney cell cultures (CEKp7).

| Genome position | Genome region | Major nt in vaccine | % | Minor nt in vaccine | % | Major nt in CEKp7 | % | Minor nt in CEKp7 | % |
|---|---|---|---|---|---|---|---|---|---|
| 1,917 | NSP2 | C | 89.1 | T | 10.9 | T | 96.8 | C | 3.2 |
| 6,468 | NSP3 | T | 99.9 | A | 0.04 | C | 96.5 | T | 3.5 |
| 16,229 | NSP13 | T | 96.8 | C | 3.2 | C | 96.3 | T | 3.7 |
| 24,837 | M | C | 100 | T | 0.02 | C | 88.9 | T | 11.1 |
| 25,481 | M ↔ ORF5 | C | 98.9 | A | 1.1 | C | 70.5. | A | 29.5 |
| 25,482 | M ↔ ORF5 | G | 98.9 | A | 1.1 | G | 70.4 | A | 29.6 |
| 26,802 | N | C | 100 | T | 0.03 | C | 88.1 | T | 11.9 |
| 27,244 | 3' UTR | C | 100 | T | 0.04 | C | 84.5 | T | 15.5 |

Bold font indicates nt that are predominant in CEKp7 to facilitate visualization of proportion they were in vaccine.
M = membrane;
N = nucleocapsid;
Arrow = between *27,244 is included in two tables, as belonging to ORF6b and as part of 3' UTR, because this part of the genome is traditionally considered part of the 3' UTR, and the significance of protein potentially encoded by ORF6b is unknown.

As seen in Table 2, a shift of populations based both on NSP and S genes was detected during CEK passage. In some cases changes indicate that the predominant population declined and a minor population became predominant. For example, the vaccine's predominant population (92.4%) displayed alanine in NSP2 at nt position 1097 and a minor population (7.6%) displayed valine at this position. After selection in CEK the predominant population (94.9%) displayed valine in NSP2 and populations displaying alanine became marginal (5%). As seen in Table 2, other examples of similar trends were observed for S1 (nt 20798) and S2 (nt 22976) genes. In other cases a different trend was observed; amino acids encoded by the initially predominant population increased even more, indicating that the amino acid encoded at these positions was shared between the minor subpopulations selected during CEK passage and the initially predominant population. Examples of this trend were seen for NSP2 gene at nt position 2,488, and S1 at nt position 20,947.

More interesting was the fact that, based on S1 sequencing, populations tended to become more homogeneous as evidenced at S1 nt positions 20,947; 21,278; and 21,502. Indeed, at these positions heterogeneity in the mixed populations contained in the vaccine was eliminated after CEK adaptation. However, this was not the case throughout the genome. For example at nucleotide position 17,641, in NSPI4 coding sequences, heterogeneity increased. An increase in heterogeneity was also observed in the 3' UTR and in the N gene, without affecting the amino acid encoded (Table 3).

CEK-adapted ArkDPI Back-passage in ECE. A single ECE passage of CEK ArkDPI passages 1, 3, 4, and 7 did not reverse the selection process occurring in the S1 gene during CEK passages. Amino acids encoded at selected S1 positions in back-passages of CEKpI and CEKp7 are shown in Table 4.

TABLE 4

S1 amino acid differences in CEK cell-passaged IBV Ark-derived vaccine after one back-passage in embryonated chicken eggs.

| Nt | Aa | Vacc | CEKp1[1] | CEKp1 Ep1[2] | CEKp7 | CEKp7 Ep1 |
|---|---|---|---|---|---|---|
| 488 | 163 | R | R (I)[3] | I | I | I |
| 968 | 323 | T (R) | T/R | R | R | R |
| 1157 | 386 | R ((H)) | R(L, H) | R | R | R |
| 1192 | 398 | E/Q | Q (E) | Q | Q | Q |

[1]EKp1, p3, or p7 = passage number in chicken kidney cells.
[2]CEKp1Ep1 = CEKp1 after 1 embryo passage.
[3]Mixed populations inferred from double nucleotide peaks at some positions.
Quantitative analysis of chromatogram peak heights at such positions specified by parenthesis: (( )) = minor peak <20% of total; ( ) = minor 20% to 40%.

For instance, the vaccine predominant population displaying arginine at S1 aa position 163, was replaced by a population displaying isoleucine in CEKp7, and maintained in CEKp7 embryo passage 1.

Figure 2:
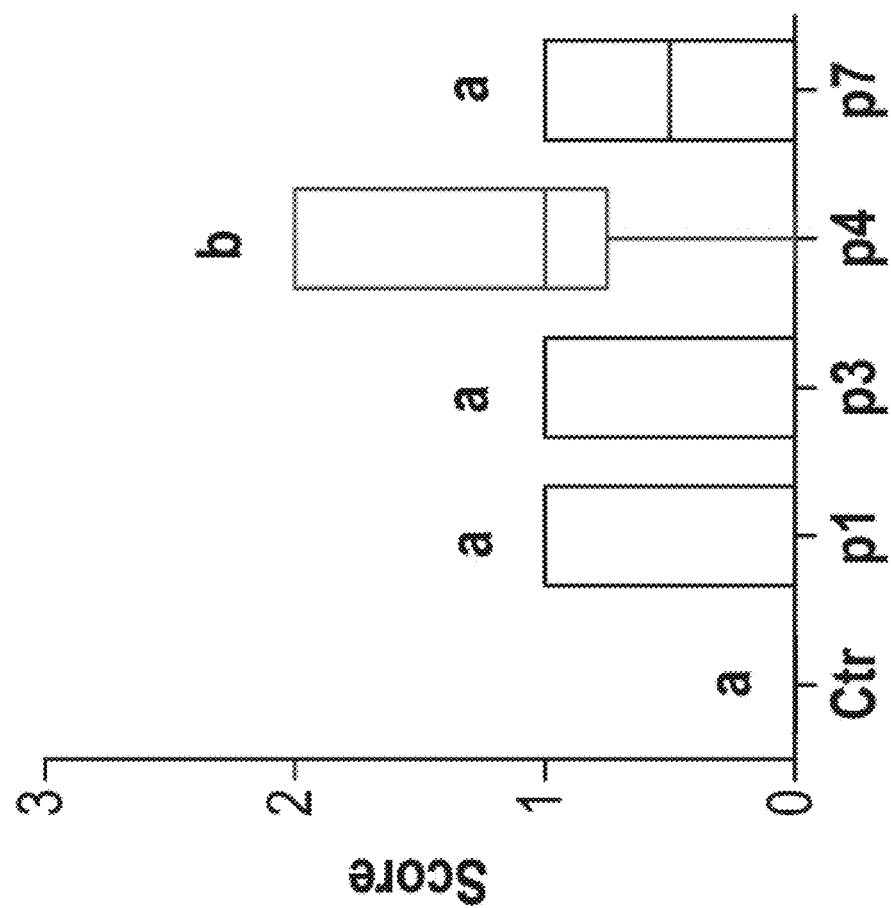
FIG. 2. Respiratory signs in chickens 5 days after inoculation at 5 days of age with a commercial attenuated ArkDPI-derived vaccine subjected to 1, 3, 4, or 7 passages (p) in CEK cells. Signs were scored individually and blindly. (Ctr)=non inoculated control. Boxes: 25th percentile, median, 75th percentile; Whiskers: Min & Max. Significant differences ($P<0.05$) indicated by different letters.
Figure 3:
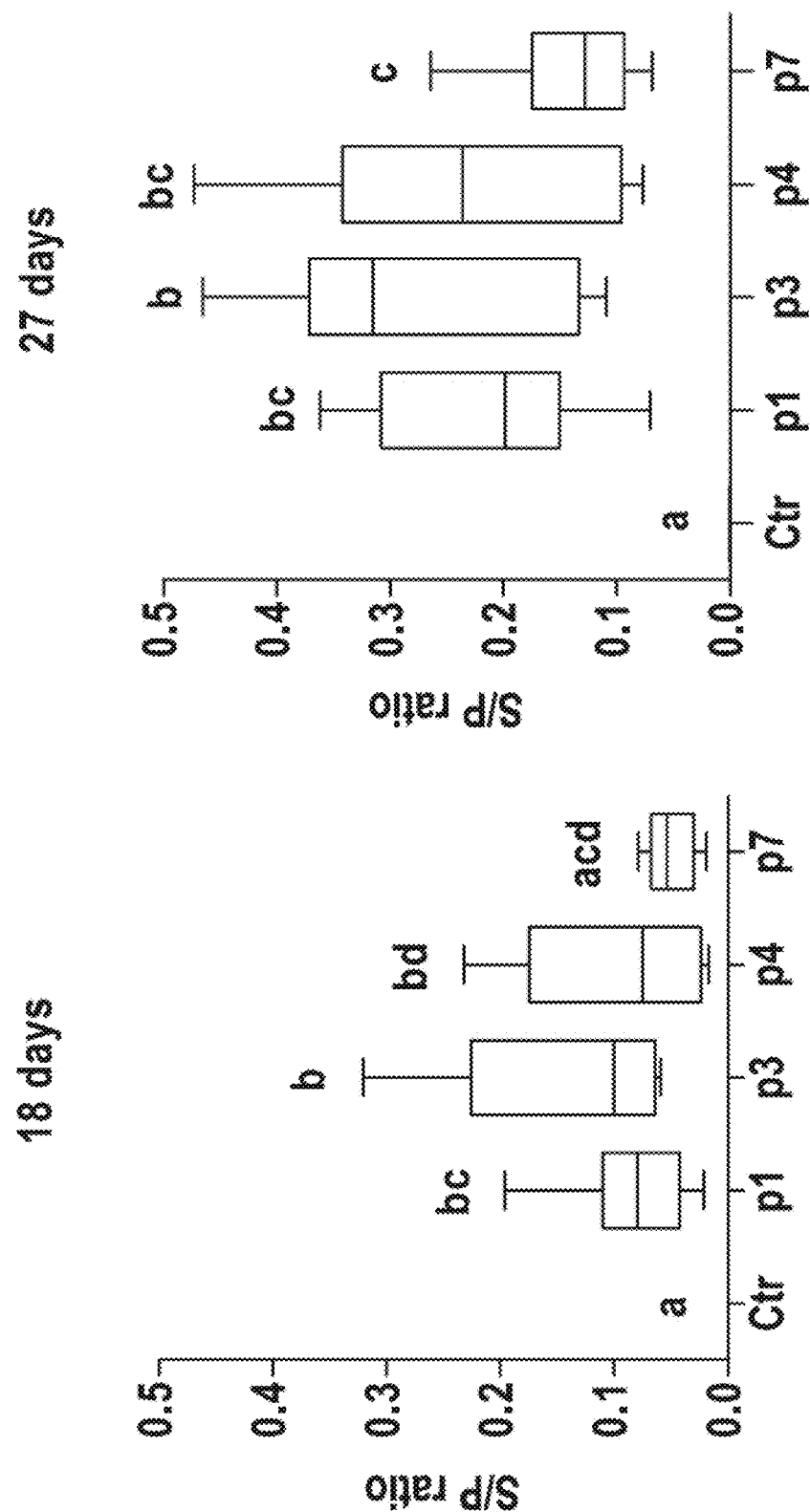
FIG. 3. IBV-specific antibody detected by ELISA [sample/positive ratio (S/P)] in sera of chickens 18 and 27 days post-inoculation with CEK cell culture passaged ArkDPI-derived vaccine. CEK passages (p) 1, 3, 4, or 7. Ctr=uninoculated control. Boxes: 25th percentile, median, 75th percentile; Whiskers: Min & Max. Significant differences ($P<0.05$) indicated by different letters.

CEK-adapted ArkDPI Passage in Chickens. Absent or mild respiratory signs were blindly detected in chickens inoculated with different passages of Ark in CEK cells (FIG. 2). Slightly increased incidence of mild signs detected in chickens inoculated with CEKp4 resulted in a statistically significant difference (P<0.05) compared to all other groups. Birds of all groups, except uninoculated controls, were positive for IBV RNA in the tear fluids by RT-PCR (not shown). As seen FIG. 3, CEK passages 1, 3, and 4 elicited specific antibodies by day 18 after inoculation while the rise of antibodies induced by CEKp7 did not achieve a significant difference compared to the uninoculated control. On day 27 post-inoculation all groups, including CEKp7, showed a significant increase (P<0.05) of IBV antibodies compared to uninoculated controls. However, antibodies induced in group CEKp3 were significantly higher than in group CEKp7 (FIG. 3). Amino acids encoded at positions that differ among S1 sequences of IBV recovered from tear fluids of individual chickens 5 days after inoculation with ArkDPI CEK passages 1, 3, and 7 are shown in Table 5.

TABLE 5

Amino acids (aa) encoded at positions that differ among IBV SJ sequences recovered from tear fluids of individual chicken 5 days after inoculation with IBV ArkDPI vaccine subjected to passages in CEK cells.

| Chicken # | nt 233 / aa 78 | nt 263 / aa 88 | nt 488 / aa 163 | nt 637 / aa 213 | nt 914 / aa 305 | nt 968 / aa 323 | nt 1052 / aa 351 | nt 1058 / aa 353 | nt 1157 / aa 386 | nt 1192 / aa 398 | nt 1195 / aa 399 |
|---|---|---|---|---|---|---|---|---|---|---|---|
| CEKp1[1] | A[2] | S | R (I)[3] | S | A | R/T | S | S | R(L/H) | Q(E) | H((Y)) |
| 1 | A | S | R/I | S(A) | A | R/T | S | F/S | H/R | Q(E) | H(Y) |
| 2 |   |   |   |   | A | T | S | S | R | E | H |
| 3 | A | S | R | A(S) | A | T | S | S | H | E | Y(H) |
| 4 | A | S | R | S | A | R | S | S | H | E | H |
| 5 |   |   |   |   | A | T | S | S | H | Q | Y |
| 6 | A | S | R | S(A) | A | T | S | S | H/R | E/Q | H/Y |
| 7 | V | S | R | S | A | T | S | S | R | E | H |
| 8 | A | N | R | S |   |   |   |   |   |   |   |
| 9 |   |   |   |   | A | T | S | S | H | Q | Y |
| 10 |   |   |   |   | A | T(R) | S | S | H/R | Q(E) | H(Y) |
| 11 |   |   |   |   | A | R(T) | S(F) | S | H(R) | Q | H(Y) |
| 12 |   |   |   |   | A | T | S | S | H(R) | Q((E)) | Y(H) |
| CEKp3 | A | S | I/R | S | A | R((T)) | S | S | L/R((H)) | Q | H((Y)) |
| 1 | A | S | I | S |   |   |   |   |   |   |   |
| 2 | A | S | I | S | A | R | R | S | R | Q | H |
| 3 | A | S | I | S | A | R | S | S | R | Q | H |
| 4 | A | S | I | S |   |   |   |   |   |   |   |
| 5 | A | S | I | S | A | R | S | S | R | Q | H |
| 6 | A | S | I | S | A | R | S | S | R | Q | H |
| 7 | A | S | I/R | S | A | R | S | S | L/R | Q | H |
| 8 | A | S | I/R | S |   |   |   |   |   |   |   |
| 9 | A | S | R | A | L | T | S | S | H | Q | Y |
| 10 |   |   |   |   | A | R | S | S | R | Q | H |
| 11 | A | S | R | S |   |   |   |   |   |   |   |
| CEKp7 | A | S | I | S | A | R | S | S | R | Q | H |
| 1 | A | S | I | S | A | R | S | S | R | Q | H |
| 2 | A | S | I | S | A | R | S | S | R | Q | H |
| 3 | A | S | I | S |   |   |   |   |   |   |   |
| 4 | A | S | I | S | A | R | S | S | R | Q | H |
| 5 | A | S | I | S | A | R | S | S | R | Q | H |
| 6 | A | S | I | S |   |   |   |   |   |   |   |

TABLE 5-continued

Amino acids (aa) encoded at positions that differ among IBV SJ sequences
recovered from tear fluids of individual chicken 5 days after inoculation
with IBV ArkDPI vaccine subjected to passages in CEK cells.

| Chicken | nt | | | | | | | | | |
|---|---|---|---|---|---|---|---|---|---|---|
| | 233 | 263 | 488 | 637 | 914 | 968 | 1052 | 1058 | 1157 | 1192 | 1195 |
| | | | | | | | aa | | | | |
| # | 78 | 88 | 163 | 213 | 305 | 323 | 351 | 353 | 386 | 398 | 399 |
| 7 | A | S | I | S | | | | | | | |
| 8 | A | S | I | S | A | R | S | S | R | Q | H |

[1]CEKp1-p7 = passage number in chicken embryonic kidney cells.
[2]Single letter amino acid code is used.
[3]Mixed populations inferred from double nucleotide peaks at some positions. Quantitative analysis of chromatogram peak heights at these positions specified as follows: (( )) indicates minor peak <20% of total; ( ) minor 20% to 40%; / = minor 40% to 50%.

As seen in Table 5, most chickens inoculated with CEKp1 showed abundant mixed populations (reflected by detection of more than one aa codon at distinct positions). In contrast, the frequency of mixed populations found in chickens inoculated with CEKp3 was considerably lower. Finally, only S1 homogeneous virus populations were rescued from chickens inoculated with CEKp7. It was also interesting to notice that changes in populations further adapted to CEK (i.e. CEKp7) were not reverted by a passage in chickens. Indeed, while a few differences were observed between the inoculated CEKp1 and CEKp3 and the viruses recovered from chickens, no differences in S1 were seen between the consensus of CEKp7 and the consensus of the virus rescued from chickens inoculated with CEKp7.

Discussion

The fact that only the higher concentrations of the ArkDPI vaccine stock ($1^{st}$ and $2^{nd}$ tenfold dilutions) induced CPE and could be successfully further passaged in CEK indicates that a minimum concentration of virus, even in the absence of an immune response, is required to establish successful expansion of a distinct virus population. Even more interesting is the kinetic pattern of the observed viral concentrations, i.e., declining virus concentration during initial serial passages and increasing concentrations concomitant with further passages. This kinetic pattern was observed using either initial dilution of the virus and thus strongly suggests adaptation to the new environment. During initial passages the predominant population in the vaccine was negatively selected likely due to lack of fitness, whilst after several replication cycles a minor subpopulation more fit in the new environment of the CEK, was able to replicate more successfully.

Both conventional and deep sequencing results consistently showed population changes resulting from adaptation of the embryo-attenuated vaccine virus to CEK cells (Tables 1 and 2). The fact that the virus replication dynamics (discussed above) were accompanied by changes in the population strongly indicates selection applied on diverse phenotypes resulted in adaptation to the kidney cell environment.

Interestingly, changes at S1 aa positions 163 and 304 differed during adaptation to CEK contingent with initial virus concentration used. Whilst it is possible that the initial virus concentration plays a relevant role on selection of IBV subpopulations, it is also plausible that the differences in subpopulations selected were the result of chance. Perhaps more interesting is the observation that subpopulations encoding the same aa at S1 position 398 quickly predominated in both passage series.

Additional nt and aa changes inside and outside the S gene resulting from adaptation to CEK cell cultures were identified by next generation sequencing of the vaccine genome prior to and after CEK cell passages. These results, which were consistent with the results of conventional sequencing, showed that, based on changes at several positions in S, the original population structure had changed during CEK adaptation (Table 2). Some changes were of particular interest. For example, the minor population in the vaccine identical to ArkDPI original passage 11 (ArkDPIp11) containing arginine at position 20,947 (1) becomes undetectable in CEKp7. The vaccine minor population identical to ArkDPIp11 in S at genome positions 21,278 and 21,502 was strongly selected in CEKp7. Interestingly, the phenylalanine codon encoding S amino acid 889 within the S2 subunit, which was detected at 96.3% frequency in CEKp7, was not the major codon in ArkDPIp11 nor ArkDPIp101 (1), suggesting that this change could be highly beneficial during adaptation of ArkDPI to CEK cell. The importance of this particular change during adaptation to CEK cells will require further studies using reverse genetics.

Outside the S gene, apparent selection was observed at seven positions, where nucleotide changes between the vaccine virus and CEK-adapted virus resulted in amino acid differences (Table 2). These include six positions where the frequency of minor nucleotides in the vaccine virus increased over 10% in CEK-adapted virus, reaching frequencies of at least 95% in four of those positions. At the seventh position, a minor nucleotide in the vaccine virus was eliminated in CEK-adapted virus. In NSP3 at nt position 4,256 the selected population encoded aspartic acid, the same as ArkDPIp11. Interestingly, we have observed the same pattern of selection at this position in a previous study (37) after inoculation of chickens with commercial ArkDPI-derived vaccine. Papain-like protease domain 2 encoded in the NSP3 of coronaviruses is an interferon antagonist (40, 41). Therefore, selection of this phenotype may be indicative of involvement in inhibition of the type 1 interferon pathway and subsequent evasion of the host innate immune response.

As discussed above, S is responsible for viral attachment and cell tropism. S has also been associated with pathogenicity (14, 23, 28) but pathogenicity of coronaviruses is also associated with genes outside S (31, 42). There is accumulating evidence that IBV virulence is influenced by NSPs encoded within the NSP 2-16 genome region (1, 2, 29). In the current study early CEK passages induced higher antibody levels and CEKp4 increased respiratory signs compared to CEKp7. CEK adaptation shifted the virus population towards homogeneity in S (Tables 2, 3). Several changes were also detected in NSPs (Table 3). Unfortunately the current study does not allow attributing distinct changes to the behavior observed in the chickens. Others have speculated that S heterogeneous viral populations may have an advantage over more homogeneous populations as they might more readily adapt to changes in the host environment (27). Thus, the lack of heterogeneity achieved in S after CEK passages may have precluded optimal replication of CEKp7 in chickens and consequently explains the lower antibody levels (FIG. 3) elicited in this group. However, the presence of increased phenotype diversity in the virus population might also result from absence of strong selective pressure which would prevent extinction of less fit phenotypes. This scenario would fit embryo-attenuated viruses because embryos harbor undifferentiated cells and lack strong immune responses at the stage used for IBV passage.

Both conventional and deep sequencing results consistently showed more homogeneous virus populations resulting from adaptation of the embryo-attenuated vaccine virus to CEK cells. As indicated above, previous work in our laboratories as well as by others has shown selection of distinct ArkDPI populations after replication in chickens (25, 38). However, other IBV attenuated vaccines, such as Mass-type vaccines, seem to be more stable as S1 sequences different from the original virus stock do not emerge during a single passage in chickens (38). We previously found that the ability of commercial Ark-type vaccines to protect chickens against Ark virulent challenge differs (34). In addition to different protection efficacy, the three vaccines compared differed in degree of variation in challenge virus following challenge. The vaccine used in the present study resulted in variation of challenge virus. The vaccines differ in their concentration of subpopulations subsequently selected in chickens as follows: while in all of these vaccines the previously identified subpopulations selected in chickens can be detected by RT-PCR, the vaccine used in the present study, coded as A in (34), shows a more homogeneous S1 population structure in the sequence chromatogram (38). Therefore, and from an applied perspective, the results presented herein indicate that CEK adaptation of current embryo-attenuated commercial Ark vaccines would reduce their heterogeneity. The current results also show that these changes are maintained after one passage in ECE, which is required for mass vaccine production, and do not revert after one replication cycle in the chicken. However, further studies to assess the protective capabilities of these more homogeneous virus populations against virulent Ark challenge are needed.

REFERENCES

1. Ammayappan, A., C. Upadhyay, J. Gelb Jr., and V. N. Vakharia. Identification of sequence changes responsible for the attenuation of avian infectious bronchitis virus strain Arkansas DPI. Arch. Virol. 154:495-499. 2009.

2. Armesto, M., D. Cavanagh, and P. Britton. The replicase gene of avian coronavirus infectious bronchitis virus is a determinant of pathogenicity. PLoS ONE 4:e7384. 2009.

3. Ballesteros, M. L., C. M. Sánchez, and L. Enjuanes. Two amino acid changes at the N-terminus of transmissible gastroenteritis coronavirus spike protein result in the loss of enteric tropism. Virology 227:378-388. 1997.

4. Baric, R. S., B. Yount, L. Hensley, S. A. Peel, and W. Chen. Episodic evolution mediates interspecies transfer of a murine coronavirus. J. Virol. 71:1946-1955. 1997.

5. Casais, R., B. Dove, D. Cavanagh, and P. Britton. Recombinant avian infectious bronchitis virus expressing a heterologous spike gene demonstrates that the spike protein is a determinant of cell tropism. J. Virol. 77:9084-9089. 2003.

6. Cavanagh, D. Severe acute respiratory syndrome vaccine development: experiences of vaccination against avian infectious bronchitis coronavirus. Avian Pathol. 32:567-582. 2003.

7. Cavanagh, D., and P. J. Davis. Coronavirus IBV: removal of spike glycopolypeptide S1 by urea abolishes infectivity and haemagglutination but not attachment to cells. J. Gen. Virol. 67:1443-1448. 1986.

8. Cavanagh, D., P. J. Davis, J. H. Darbyshire, and R. W. Peters. Coronavirus IBV: virus retaining spike glycopolypeptide S2 but not S1 is unable to induce virus-neutralizing or haemagglutination-inhibiting antibody, or induce chicken tracheal protection. J. Gen. Virol. 67:1435-1442. 1986.

9. Cavanagh, D., K. Mawditt, A. Adzhar, R. E. Gough, J. P. Picault, C. J. Naylor, D. Haydon, K. Shaw, and P. Britton. Does IBV change slowly despite the capacity of the spike protein to vary greatly? Adv. Exp. Med. Biol. 440:729-734. 1998.

10. Domingo, E., E. Baranowski, C. M. Ruiz-Jarabo, A. M. Martin-Hernandez, J. C. Saiz, and C. Escarmis. Quasispecies structure and persistence of RNA viruses. Emerg. Infect. Dis. 4:521-527. 1998.

11. Enjuanes, L., D. Brian, D. Cavanagh, K. Holmes, M. M. C. Lai, H. Laude, P. Masters, P. Rottier, S. G. Siddell, W. J. M. Spaan, F. Taguchi, and P. Talbot. Coronaviridae. In: Virus taxonomy. Classification and nomenclature of viruses. M. H. V. van Regenmortel, C. M. Fauquet, D. H. L. Bishop, E. B. Carstens, M. K. Estes, S. Lemon, J. Maniloff, M. Mayo, D. J. McGeoch, C. R. Pringle, and R. B. Wickner, eds. Academic Press, New York. pp. 835-849. 2000.

12. Enjuanes, L., W. J. Spaan, E. J. Snijder, and D. Cavanagh. Nidovirales. In: Virus taxonomy. Classification and nomenclature of viruses. M. H. V. van Regenmortel, C. M. Fauquet, D. H. L. Bishop, E. B. Carsten, M. K. Estes, S. M. Lemon, D. J. McGeoch, J. Maniloff, M. A. Mayo, C. R. Pringle, and R. B. Wickner, eds. Academic Press, New York. pp. 827-834. 2000.

13. Fang, S. G., S. Shen, F. P. Tay, and D. X. Liu. Selection of and recombination between minor variants lead to the adaptation of an avian coronavirus to primate cells. Biochem. Biophys. Res. Comm. 336:417-423. 2005.

14. Fazakerley, J. K., S. E. Parker, F. Bloom, and M. J. Buchmeier. The V5A13.1 envelope glycoprotein deletion mutant of mouse hepatitis virus type-4 is neuroattenuated by its reduced rate of spread in the central nervous system. Virology 187:178-188. 1992.

15. Gallardo, R. A., V. L. van Santen, and H. Toro. Host intraspatial selection of infectious bronchitis virus populations. Avian Dis. 54:807-813. 2010.

16. Hingley, S. T., J. L. Gombold, E. Lavi, and S. R. Weiss. MHV-A59 fusion mutants are attenuated and display altered hepatotropism. Virology 200:1-10. 1994.

17. Jackwood, M. W., D. A. Hilt, C. W. Lee, H. M. Kwon, S. A. Callison, K. M. Moore, H. Moscoso, H. Sellers, and S. Thayer. Data from 11 years of molecular typing infectious bronchitis virus field isolates. Avian Dis. 49:614-618. 2005.

18. Koch, G., L. Hartog, A. Kant, and D. J. van Roozelaar. Antigenic domains on the peplomer protein of avian infectious bronchitis virus: correlation with biological functions. J. Gen. Virol. 71:1929-1935. 1990.

19. Kusters, J. G., E. J. Jager, J. A. Lenstra, G. Koch, W. P. Posthumus, R. H. Meloen, J. and B. A. van der Zeijst. Analysis of an immunodominant region of infectious bronchitis virus. J. Immunol. 143:2692-2698. 1989.

20. Kusters, J. G., H. G. Niesters, N. M. Bleumink-Pluym, F. G. Davelaar, M. C. Horzinek, and B. A. van der Zeijst. Molecular epidemiology of infectious bronchitis virus in The Netherlands. J. Gen. Virol. 68:343-352. 1987.

21. Kwon, H. M., M. W. Jackwood, and J. Gelb Jr. Differentiation of infectious bronchitis virus serotypes using polymerase chain reaction and restriction fragment length polymorphism analysis. Avian Dis. 37:194-202. 1993.

22. Lai, M. M. C., and K. V. Holmes. Coronaviridae: the viruses and their replication. In: Fundamental virology. D. M. Knipe and P. M. Howley, eds. Lippincott Williams and Wilkins, Philadelphia. pp. 641-663. 2001.

23. Leparc-Goffart, I., S. T. Hingley, M. M. Chua, X. Jiang, E. Lavi, and S. R. Weiss. Altered pathogenesis of a mutant of the murine coronavirus MHV-A59 is associated with a Q159L amino acid substitution in the spike protein. Virology 269:1-10. 1997.

24. Li, W., C. Zhang, J. Sui, J. H. Kuhn, M. J. Moore, S. Luo, S. K. Wong, I. C. Huang, K. Xu, N. Vasilieva, A. Murakami, Y. He, W. A. Marasco, Y. Guan, H. Choe, and M. Farzan. Receptor and viral determinants of SARS-coronavirus adaptation to human ACE2. EMBO J. 24:1634-1643. 2005.

25. McKinley, E. T., D. A. Hilt, and M. W. Jackwood. Avian coronavirus infectious bronchitis attenuated live vaccines undergo selection of subpopulations and mutations following vaccination. Vaccine 26:1274-1284. 2008.

26. Ndegwa, E. N., K. S. Joiner, H. Toro, F. W. van Ginkel, and V. L. van Santen. The proportion of specific viral subpopulations in attenuated ArkDPI infectious bronchitis vaccines influences vaccination outcome. Avian Dis. 56:642-653. 2012.

27. Nix, W. A., D. S. Troeber, B. F. Kingham, C. L. Keeler Jr., and J. Gelb Jr. Emergence of subtype strains of the Arkansas serotype of infectious bronchitis virus in Delmarva broiler chickens. Avian Dis. 44:568-581. 2000.

28. Ontiveros, E., T. S. Kim, T. M. Gallagher, and S. Perlman. Enhanced virulence mediated by the murine coronavirus, mouse hepatitis virus strain JHM, is associated with a glycine at residue 310 of the spike glycoprotein. J. Virol. 77:10260-10269. 2003.

29. Phillips, J. E., M. W. Jackwood, E. T. McKinley, S. W. Thor, D. A. Hilt, N. D. Acevedol, S. M. Williams, J. C. Kissinger, A. H. Paterson, J. S. Robertson, and C. Lemke. Changes in nonstructural protein 3 are associated with attenuation in avian coronavirus infectious bronchitis virus. Virus Genes 44:63-74. 2012.

30. Schat, K. A., and H. G. Purchase. Cell-culture methods. In: A laboratory manual for the isolation and identification of avian pathogens. D. E. Swayne, J. Glisson, M. W. Jackwood, J. E. Pearson, and W. M. Reed, eds. American Association of Avian Pathologists, Inc., Kenneth Square, Pa. pp. 223-234. 1998.

31. Sperry, S. M., L. Kazi, R. L. Graham, R. S. Baric, S. R. Weiss, and M. R. Denison. Single-amino-acid substitutions in open reading frame (ORF) 1b-nsp14 and ORF 2a proteins of the coronavirus mouse hepatitis virus are attenuating in mice. J. Virol. 79:3391-3400. 2005.

32. Toro, H., J. W. Jackwood, and V. L. van Santen. Genetic diversity and selection regulates evolution of infectious bronchitis virus. Avian Dis. 56:449-455. 2012.

33. Toro, H., P. Lavaud, P. Vallejos, and A. Ferreira. Transfer of IgG from serum to lachrimal fluid in chickens. Avian Dis. 37:60-66. 1993.

34. Toro, H., D. Pennington, R. A. Gallardo, V. L. van Santen, F. W. van Ginkel, J. F. Zhang, and K. S. Joiner. Infectious bronchitis virus subpopulations in vaccinated chickens after challenge. Avian Dis. 56:501-508. 2012.

35. Toro, H., V. L. van Santen, L. Li, S. B. Lockaby, E. van Santen, and F. J. Hoerr. Epidemiological and experimental evidence for immunodeficiency affecting avian infectious bronchitis. Avian Pathol. 35:1-10. 2006.

36. van Ginkel, F. W., V. L. van Santen, S. L. Gulley, and H. Toro. Infectious bronchitis virus in the chicken Harderian gland and lachrymal fluid: viral load, infectivity, immune cell responses, and effects of viral immunodeficiency. Avian Dis. 52:608-617. 2008.

37. van Santen, V. L., G. E. Thaxton, E. N. Ndegwa, R. A. Gallardo, and H. Toro. ArkDPI-derived IBV vaccines and their subpopulations selected in chickens: differences outside the S gene VII. International Symposium Avian Corona- and Pneumoviruses and Complicating Pathogens. pp. 94-97. Rauischholzhausen, Germany. 2012.

38. van Santen, V. L., and H. Toro. Rapid selection in chickens of subpopulations within ArkDPI-derived infectious bronchitis virus vaccines. Avian Pathol. 37:293-306. 2008.

39. Villegas, P. Titration of biological suspensions. In: A laboratory manual for the isolation, identification and characterization of avian pathogens. L. Dufour-Zavala, D. E. Swayne, J. Glisson, M. W. Jackwood, J. E. Pearson, W. M. Reed, and P. R. Woolcock, eds. American Association of Avian Pathologists, Athens, Ga. pp. 217-221. 2008.

40. Wang, G., G. Chen, D. Zheng, G. Cheng, and H. Tang. PLP2 of mouse hepatitis virus A59 (MHV-A59) targets TBK1 to negatively regulate cellular type I interferon signaling pathway. PLoS ONE 6:17192. 2011.

41. Zheng, D., G. Chen, B. Guo, G. Cheng, and H. Tang. PLP2, a potent deubiquitinase from murine hepatitis virus, strongly inhibits cellular type I interferon production. Cell Res. 18:1105-1113. 2008.

42. Zust, R., L. Cervantes-Barragan, T. Kuri, G. Blakqori, F. Weber, B. Ludewig, and V. Thiel. Coronavirus non-structural protein 1 is a major pathogenicity factor: implications for the rational design of coronavirus vaccines. PLoS Pathog 3:e109. 2007.

Example 2

Kidney Cell-Adapted Infectious Bronchitis ArkDPI Vaccine Confers Effective Protection Against Challenge Abbreviations Ark=Arkansas; CEK=chicken embryo kidney; CEKp7-Ep1=seven passages in CEK and one passage in chicken embryo; DPI=Delmarva Poultry Industry; EID50=50% embryo infectious dose; IBV=infectious bronchitis virus; NSP=non-structural protein; qRT-PCR=quantitative RT-PCR; RT-PCR=reverse transcriptase PCR; S=spike; SPF=specific pathogen free Summary We previously demonstrated that adaptation of an embryo-attenuated infectious bronchitis Arkansas Delmarva Poultry Industry (ArkDPI)-derived vaccine to chicken embryo kidney (CEK) cell shifted the virus population towards homogeneity in spike (S) and non-structural protein (NSP) genes. Moreover, the typical Ark subpopulations emerging in chickens vaccinated with commercial Ark vaccines were not detected in chickens vaccinated with the CEK-adapted virus. In this study, chickens vaccinated with a low dose ($1.6 \times 10^3$ $EID_{50}$/bird) of CEK-adapted Ark vaccine at 5 days of age showed a significant reduction of IBV RNA in the lachrymal fluids and decreased incidence of IBV RNA detection in tracheal swabs 5 days after challenge compared to unvaccinated challenged chickens. In a second experiment 5-day-old chickens were vaccinated with $10^4$ or $10^5$ $EID_{50}$/chicken of CEK-adapted Ark and protection was compared to chickens vaccinated with $10^5$ $EID_{50}$/chicken of the commercially available ArkDPI-derived vaccine. All vaccinated chicken groups showed a significant reduction of respiratory signs and viral load 5 days after Ark virulent challenge compared to unvaccinated-challenged controls. No subpopulations different from the challenge virus were detected in chickens vaccinated with CEK-Ark after challenge. In contrast, IBV S1 sequences differing from the predominant in the challenge virus were detected in chickens vaccinated with the commercial Ark attenuated vaccine. From an applied perspective, the CEK-adapted IBV ArkDPI-derived vaccine is an improved and effective vaccine candidate to protect chickens against virulent Ark-type strains.

Background Information

In the United States IBV Arkansas (Ark)-type wild and vaccine-like strains have accounted for more than 50% of IBV respiratory disease in chickens during the last decade and beyond (7, 9, 12, 15). The high prevalence of Ark viruses occurs despite extensive vaccination with different commercial embryo-attenuated Ark vaccines which all originate from the same Ark Delmarva Poultry Industry (DPI) IBV isolate. ArkDPI-derived vaccine viruses show increased persistence in commercial broilers compared to IBV vaccines belonging to other serotypes (8) which increases the opportunities for viral recombination and/or mutation. Furthermore, gene sequence analyses have revealed ArkDPI-derived vaccines containing multiple viral minor subpopulations which become predominant in the chickens after vaccination (9, 18). These viral subpopulations, which show distinct behaviors in chickens (3, 4, 10, 11), likely provide a source for the emergence of vaccine-like viruses commonly isolated from broiler respiratory disease. Finally, the varying proportions of viral subpopulations contained in the commercial Ark-derived vaccines influence the vaccine replication ability in the host and subsequently induced immune responses. Weaker immune responses after Ark vaccination have been shown to result in rise of virus subpopulations from a wild Ark challenge virus (14), a phenomenon that might also contribute to emergence of novel Ark variants.

IBV evolves by natural selection, i.e. generation of genetic diversity from mutation and recombination events followed by selection of the most fit IBV phenotypes (13). We previously investigated genetic and phenotypic changes associated with adaptation of an embryo-attenuated IBV ArkDPI-derived vaccine virus to chicken embryo kidney (CEK) cells. The virus population shifted towards homogeneity in spike (S) and nonstructural (NSP) genes after seven passages in CEK. Based on S gene sequencing the changes of the predominant Ark population after CEK adaptation were not reverted after one back-passage in embryonated chicken eggs nor after a passage in chickens (6). Because of the advantages of this more stable and homogeneous CEK-adapted ArkDPI virus, this study was aimed at evaluating its ability to confer protection against homologous challenge.

Materials and Methods

Chickens. White leghorn chickens hatched from specific pathogen free (SPF) fertile eggs (Sunrise Farms, Catskill, N.Y.) were used in two experiments. Hatched chickens were maintained in Horsfall-type isolators in biosafety level 2 facilities. Experimental procedures and animal care were performed in compliance with all applicable federal and institutional animal use guidelines. Auburn University College of Veterinary Medicine is an Association for Assessment and Accreditation of Laboratory Animal Care-accredited institution.

Viruses. The previously described CEK passage 7ArkDPI vaccine virus subjected to one additional passage in embryonated chicken eggs (CEKp7-Ep1) (6) was used a 3 different dose levels as indicated in the experimental design below. In the second experiment a commercially available ArkDPI-type embryo-attenuated vaccine, from which the CEK-adapted virus originated, was used as an additional control. An IBV Ark-type virulent strain (GenBank accession #JN861120) previously described (2) was used for challenge purposes. Viruses were titered in embryonated chicken eggs as generally accepted (5, 19) but in addition to embryo macroscopic changes, we used the embryo weight and detection of IBV RNA in embryo kidneys to determine virus replication and subsequently calculate the virus titer. In brief, embryos were evaluated macroscopically for IBV typical changes which are usually obvious at lower dilutions of the virus. Live embryos without obvious lesions were weighed and considered positive if the value fell below 2 standard deviations of the average of uninfected controls. Finally, kidney samples were obtained from embryos inoculated with higher virus dilutions and presence of IBV RNA determined by RT-PCR as previously described (17). Thus, the titration method is more sensitive than the generally accepted method. Vaccinations and challenge were performed with a total volume of 100 μl of virus stock; i.e., each bird was inoculated with 25 μl in each nostril and each eye.

Experimental Design

Experiment 1. Two groups of chickens were established. Chickens in group 1 (n=14) were vaccinated with $1.6 \times 10^3$ $EID_{50}$/bird of CEKp7-EP1 at 5 days of age. Chickens in group 2 (n=17) were the unvaccinated controls. Chickens of groups 1 and 2 were challenged 23 days after vaccination with $10^{5.0}$ $EID_{50}$/bird 100 μl of virulent IBV Ark. An additional non-vaccinated/non-challenged chicken group (n=10) served as the negative control. Protection conferred by CEKp7-EP1 was evaluated 5 day after challenge by relative viral load in the tears by qRT-PCR and incidence of detectable IBV RNA in the trachea detectable by RT-PCR. Extraction of RNA from lachrymal fluids and tracheal swabs was performed with the Qiagen QIAamp viral RNA mini kit (Qiagen, Valencia, Calif.). Relative viral load in lachrymal fluids was determined by Taqman® quantitative reverse transcriptase PCR (qRT-PCR) (1) using Bio-Rad CFX96 Real-Time PCR detection system to quantitate viral RNA. The incidence of detectable IBV RNA in tracheal swabs was determined by conventional RT-PCR detecting the N gene as previously described (15).

Experiment 2. Four chicken treatment groups were established (each n=18). Chickens in group 1 were vaccinated with $10^5$ $EID_{50}$/bird of a commercially available ArkDPI-type vaccine at 5 day of age. Chickens in groups 2 and 3 were vaccinated with $10^4$ $EID_{50}$/bird and $10^5$ $EID_{50}$/bird of CEKp7-EP1 at 5 days of age respectively. Chickens in group 4 served as non-vaccinated/challenged controls. All birds were challenged 15 day after vaccination with $10^{5.0}$ $EID_{50}$/bird 100 μl of the virulent IBV Ark. An additional non-vaccinated/non-challenged chicken group (n=10) served as the negative control. Protection against challenge was evaluated 5 days after challenge by clinical signs, viral load, and tracheal histopathology. Respiratory rales (nasal and/or tracheal) were evaluated blindly by close listening to each bird and scored as 0 (absent), 1 (mild), 2 (moderate), or 3 (severe)

as described (15). Viral load in tears was determined by qRT-PCR as described above for tears (15, 16). In addition, IBV RNA obtained from chickens vaccinated with the commercial Ark vaccine or CEK7Ep1 after challenge was submitted for spike gene (S1) sequencing performed as previously described (14). In addition, the spike (S1) gene sequence of IBV RNA obtained from tears after challenge from chickens vaccinated with the commercial Ark vaccine or CEK7-Ep1 was determined as previously described (14). Finally, tracheal histopathology was evaluated and histomorphometry was performed essentially as previously described (15, 16). In brief, necrosis and deciliation in the tracheal mucosa were evaluated blindly and scored 1 through 5 based on severity (i.e., normal, mild, moderate, marked, severe). Histomorphometry was performed on a single digitally photographed microscopic field (200× magnification) containing a representative longitudinal section of the cranial one-third of the tracheal mucosa and the supporting cartilage ring. Histomorphometric data for mucosal thickness and lymphocyte infiltration were collected using the ImageJ morphometry program (rsb.info.nih.gov/ij/download.html). Five measurements were performed at regular intervals along the length of a single tracheal ring with the linear tool. Values for each chicken group were analyzed by one-way ANOVA followed by Tukey multiple comparisons test. Differences were considered significant with P values of <0.05.

Results

Figure 4:
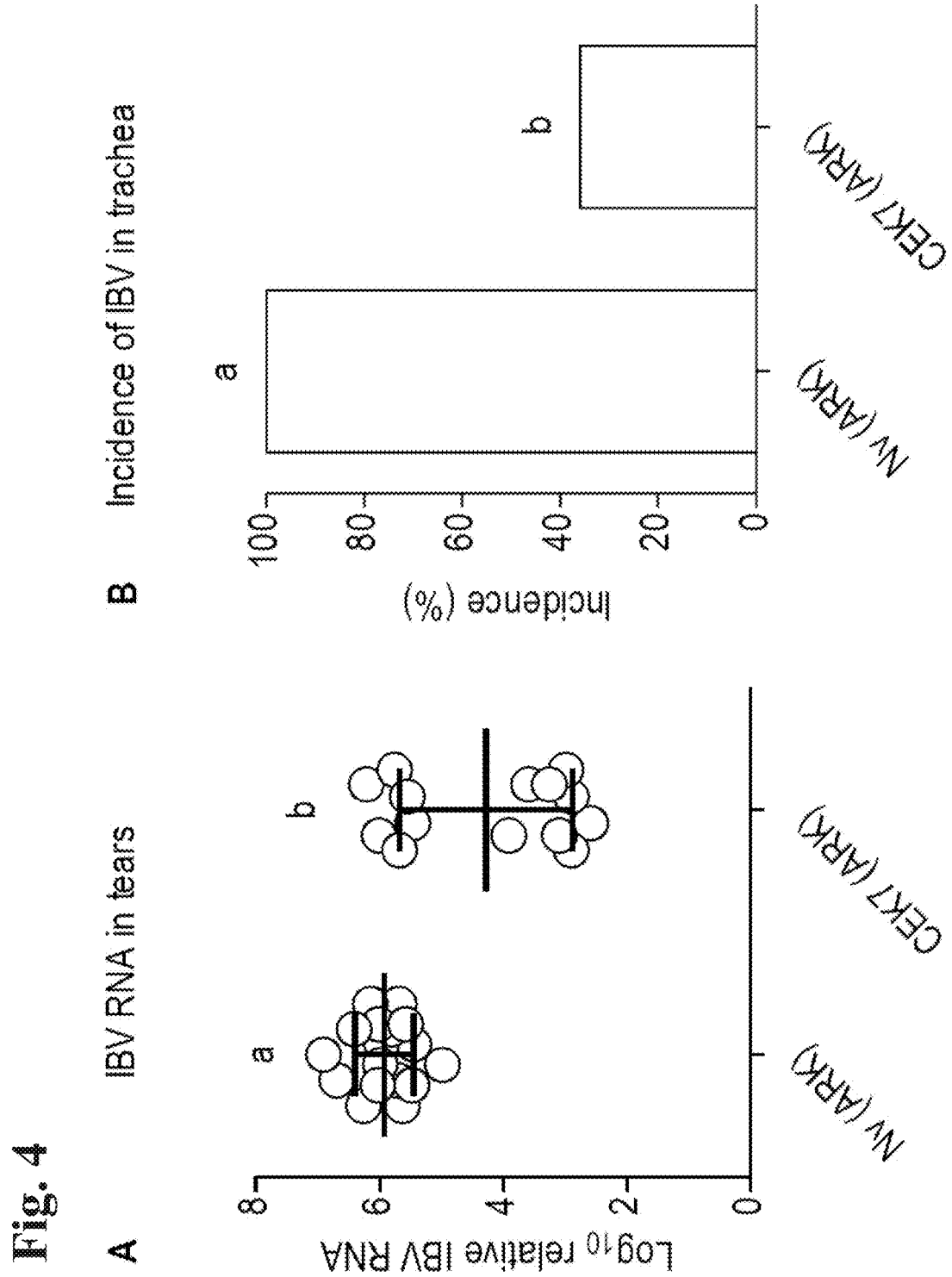
FIG. 4. (A) IBV RNA in lachrymal fluids (individual values, average and SD) detected 5 days after challenge in chickens vaccinated with $1.6\times10^3$ $EID_{50}$ bird of CEK7-Ep1 and challenged with $10^5$ $EID_{50}$/bird of a virulent IBV Ark strain (ARK) 23 days after vaccination. (B) Incidence of IBV RNA in tracheal swabs 5 day post-challenge detected by conventional RT-PCR (N gene). Nv (ARK)=unvaccinated/Ark-challenged. Different letters indicate significant differences in A by ANOVA and in B by Fisher's exact test ($P<0.05$).

The results of experiment 1 are shown in FIG. 4. As seen in FIG. 4, chickens vaccinated with CEKp7-Ep1 at 5 day of age showed a significant reduction of viral load in the lachrymal fluids (FIG. 4A) and a significant reduction of the incidence of IBV RNA in the tracheas (FIG. 4B) 5 days after challenge compared to unvaccinated challenged controls.

Figure 5:
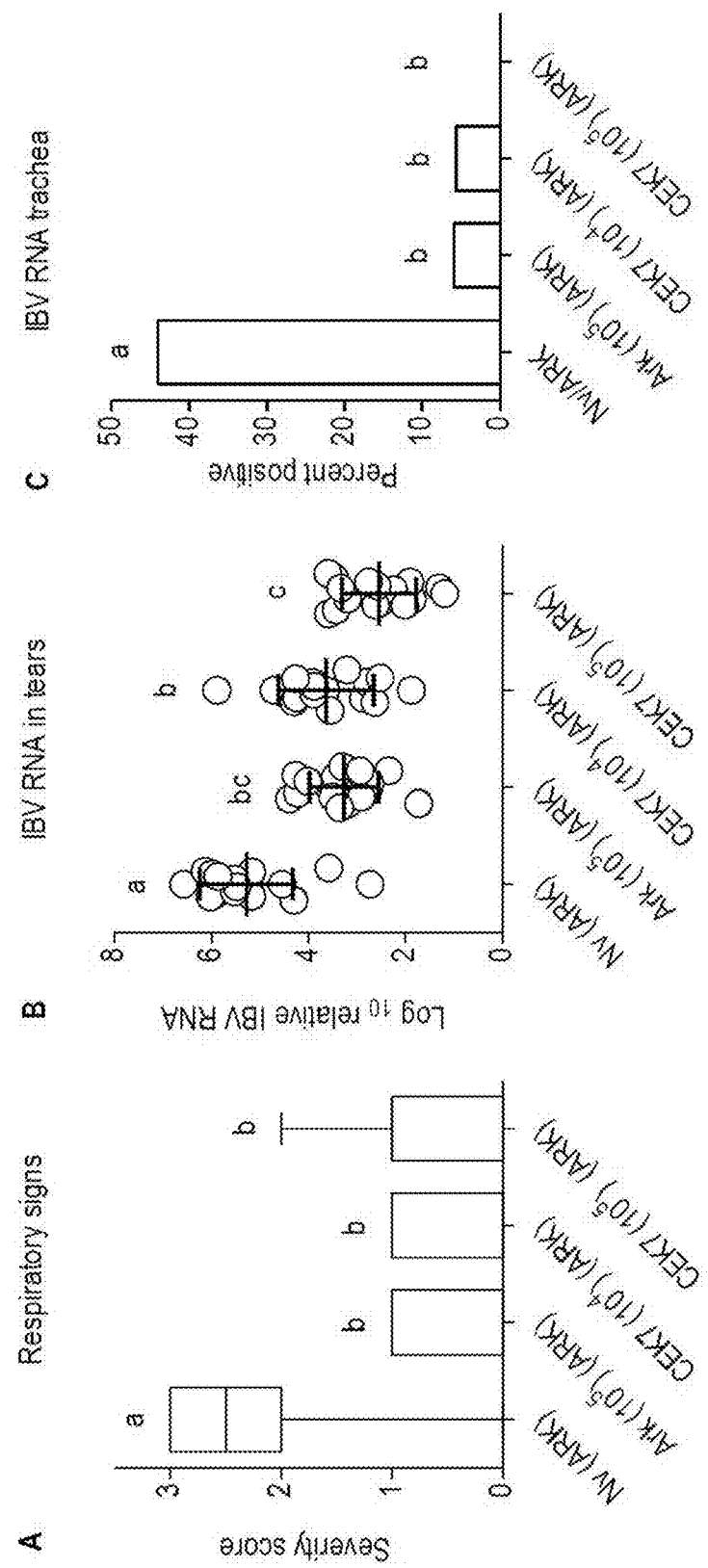
FIG. 5. (A) Respiratory signs (boxes: 25th percentile, median, 75th percentile; whiskers: minimum & maximum); (B) IBV RNA in tears (individual values, average, and SD) and incidence of detection of IBV RNA by Taqman qRT-PCR in tracheal swabs 5 days post challenge with virulent IBV Ark (ARK) in chickens (n=18/group) at 20 days-old that had been vaccinated at 5 days of age either with a $10^5$ $EID_{50}$ bird of commercial attenuated ArkDPI-derived vaccine (Ark) or the CEK-adapted ArkDPI (CEK7) at two dosage levels ($10^4$ or $10^5$ $EID_{50}$/bird). Nv (ARK)=unvaccinated/Ark-challenged. Different letters indicate significant differences ($P<0.05$).
Figure 6:
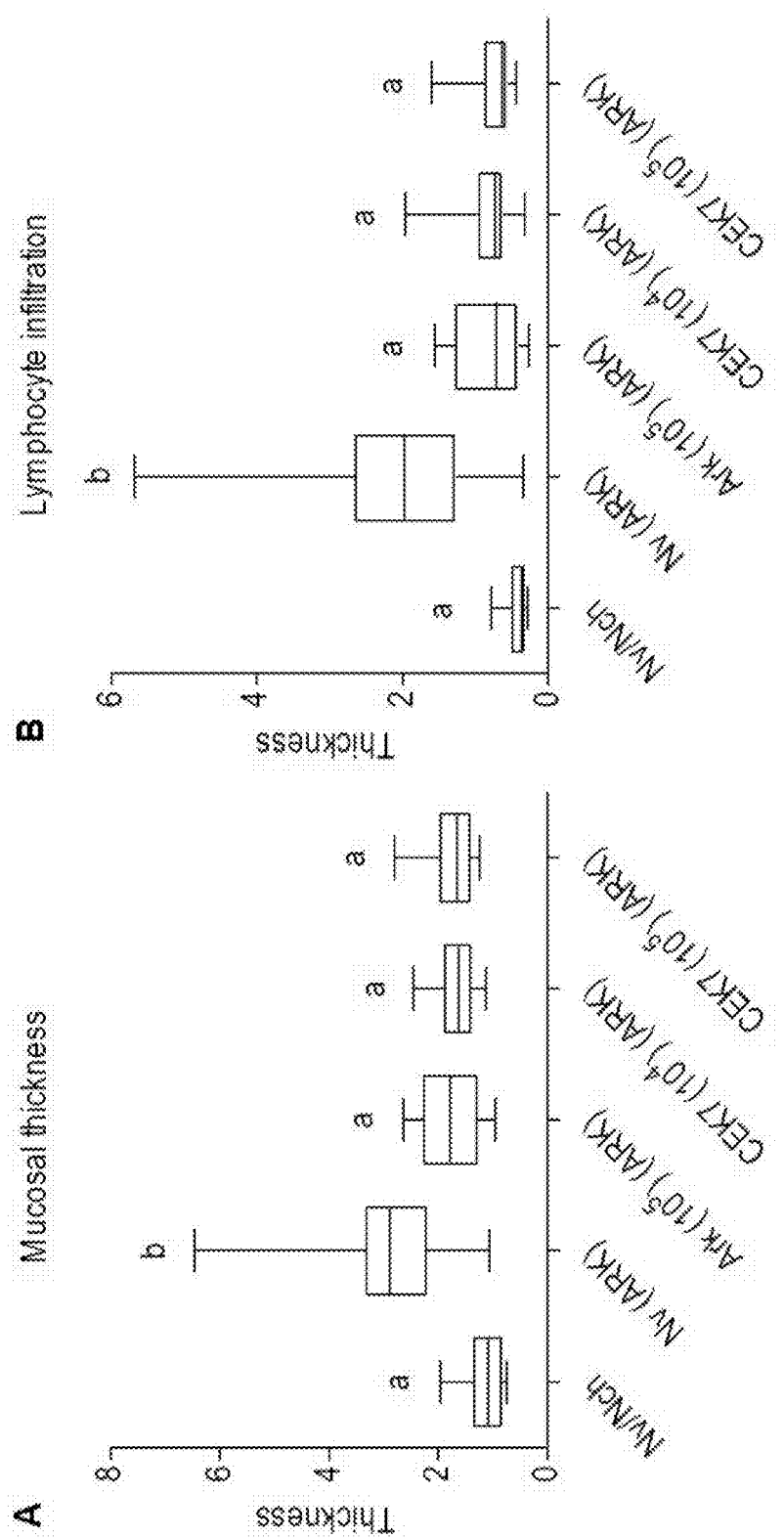
FIG. 6. (A) Tracheal mucosal thickness and (B) lymphocyte infiltration (boxes: $25^{th}$ percentile, median, 75th percentile; whiskers: minimum & maximum); were evaluated blindly by histomorphometry 5 days post-challenge in chickens (n=18/group) vaccinated at 5 days of age either with a commercially available attenuated ArkDPI-derived vaccine (Ark) or the CEK-adapted ArkDPI virus at two different doses and subsequently challenged with a wild IBV Ark strain at 20 days of age. Nv (ARK) unvaccinated/Ark challenged. Nv/Nch=unvaccinated/not challenged (n=10); Different letters indicate significant differences between groups by ANOVA ($P<0.05$).

The results of experiment 2 are shown in FIGS. 5-7. As seen in FIG. 5, all vaccinated chickens, i.e., chickens vaccinated with the commercial ArkDPI-derived vaccine, as well as chickens vaccinated with CEKp7-Ep1 at 2 different dosage levels, were protected from respiratory signs 5 days after challenge (FIG. 5A), while unvaccinated controls showed severe respiratory disease. Similarly, both vaccines significantly reduced the IBV viral load in the lachrymal fluids (FIG. 5B) compared to unvaccinated challenged controls 5 days after challenge. Moreover, chickens vaccinated with $10^5$ $EID_{50}$ of CEKp7-EP1 showed a significantly lower viral load in tears compared to chickens vaccinated with the lower dose ($10^4$ $EID_{50}$/chicken) of this virus. Both vaccines also eliminated detection of viral RNA in tracheal swabs by qRT189 PCR 5 days after challenge in all but at most one chicken per vaccinated group, compared to detection of challenge virus in tracheas of 44% of unvaccinated challenged chickens (FIG. 5C). Consistent with results of viral load and clinical signs, both tracheal histomorphometry (FIG. 6) and histopathology (FIG. 7) showed that all vaccines protected similarly without significant differences, based on tracheal mucosal thickness (FIG. 6A) lymphocyte infiltration (FIG. 6B) and tracheal lesion scores (FIG. 7 A,B,C) compared to unvaccinated challenged chickens.

IBV populations based on S1 sequences recovered 5 days after challenge from the tears of chickens vaccinated with the Ark commercial vaccine are shown in Table 6.

TABLE 6

Predominant virus populations identified in chickens 5 days after challenge at 20 days-old with a wild type Ark IBV strain. Chickens had been vaccinated at 5 days of age with a commercial ArkDPI-type IBV vaccine.

| Number of chickens[B] | S1 AA position[A] | | | | | | | | Virus Population[C] |
|---|---|---|---|---|---|---|---|---|---|
| | 56 | 76 | 95 | 95 | 95 | 115 | 144 | 160 | 171 | |
| 14 | Asn | Phe | Ser | Ser | Ser | Phe | Thr | Pro | His | P1 |
| 1 | Asn | Phe | Ser | Ser | Ser | Phe | Thr | Leu/Pro | His | P2/P1 |
| 1 | Ser | Leu | Asn | Asn | Asn | Tyr | Met | Pro | Tyr | P5[D] |
| 1 | Ser/Asn | Leu/Phe | Asn/Ser | Asn/Ser | Asn/Ser | Tyr/Phe | Met/Thr | Pro | Tyr/His | P5/P1 |

[A]Only amino acid positions where viral populations recovered differ are shown. Bold letters indicate amino acids different from challenge virus major population (P1).
[B]Tears from one of the 18 chickens in the group vaccinated with commercial ArkDPI-type vaccine and challenged with wild Ark IBV strain did not yield an S1 sequence.
[C]Virus populations as designated in Toro et al., 2012 (14).
[D]The virus population designated P5 in Toro et al., 2012 (14) was a mixture of at least two distinct populations. The virus population designated P5 here contains only one of those two populations.

As seen in Table 6, while IBV recovered from most chickens had S1 sequences identical to the challenge virus, subpopulations differing from the predominant population of the challenge virus predominated in 3 chickens vaccinated with the commercial Ark vaccine. The IBV S1 sequences found correspond to two distinct populations detected in chickens vaccinated with Ark attenuated vaccines in a previous study, which were designated P2 and P5 (14). In contrast, no subpopulations different from the challenge virus were detected in chickens vaccinated with CEKp7-Ep1.

Discussion

Genetic heterogeneity has been demonstrated among commercial IBV Ark serotype vaccines from different manufacturers (9, 18) and different production stocks (9) despite being derived from the same ArkDPI original IBV isolate. Selection of distinct ArkDPI phenotypes has also been reported after replication of IBV ArkDPI-derived vaccines in chickens (4, 9, 18). Additionally, new Ark-like isolates continue to emerge (7). We previously compared the effectiveness of three ArkDPI-derived attenuated vaccines from different companies to protect against Ark virulent challenge (14). These vaccines differed in the proportion of subpopulations prior to selection in the host and behaved differently in terms of vaccine viral load and respiratory reactions (10). Vaccinated chickens were protected against challenge but slight differences in the severity of signs and lesions were observed. In addition, chickens in the group with the strongest immune response were able to successfully impede replication of the challenge virus in most chickens, and only the population predominant in the challenge strain was detected in a few IBV-positive birds. In contrast, in groups showing less than optimal specific immune responses, IBV was detected in most chickens, and subpopulations different from the predominant one in the challenge strain were selected and became predominant. Therefore, improvement of this type of vaccine is necessary.

Adaptation of an embryo attenuated IBV ArkDPI-derived vaccine to CEK cell culture shifted the virus population towards homogeneity in S and NSP genes, and the changes achieved in the S1 gene in CEK-adapted virus were maintained after one back-passage in embryonated chicken eggs or chickens (6). Results of the present vaccination/challenge study indicate effective protection against challenge following immunization with the CEK-adapted virus. No adverse clinical vaccine reactions were detected in vaccinated chickens and when used at the same dose or even a 10-fold lower dose than the commercial vaccine, protection was as effective. Moreover, the CEKp7Ep1 Ark vaccine successfully reduced replication of the challenge virus, and only the virus population predominant in the challenge strain was detected. Therefore, the homogeneous kidney cell-adapted IBV ArkDPI-derived vaccine (CEKp7-Ep1) offers an improvement/refinement of current ArkDPI-derived vaccines by both eliminating emergence of vaccine subpopulations after vaccination and eliminating subpopulations after wild Ark challenge.

REFERENCES

1. Callison, S. A., D. A. Hilt, T. O. Boynton, B. F. Sample, R. Robison, D. E. Swayne, and M. W. Jackwood. Development and evaluation of a real-time taqman rt-PCR assay for the detection of infectious bronchitis virus from infected chickens. J. Virol. Methods 138:60-65. 2006.

2. Gallardo, R. A., F. J. Hoerr, W. D. Berry, V. L. van Santen, and H. Toro. Infectious bronchitis virus in testicles and venereal transmission. Avian Dis 55:255-258. 2011.

3. Gallardo, R. A., V. L. van Santen, and H. Toro. Effects of chicken anemia virus and infectious bursal disease virus-induced immunodeficiency on infectious bronchitis virus replication and genotypic drift. Avian Pathol. 41:451-458. 2012.

4. Gallardo, R. A., V. L. van Santen, and H. Toro. Host intraspatial selection of infectious bronchitis virus populations. Avian Dis. 54:807-813. 2010.

5. Gelb, J., Jr., and M. W. Jackwood. Infectious bronchitis. In: A laboratory manual for the isolation, identification and characterization of avian pathogens. L. Dufour-Zavala, D. E. Swayne, J. R. Glisson, J. E. Pearson, W. M. Reed, M. W. Jackwood, and P. R. Woolcock, eds. American Association of Avian Pathologists, Athens, Ga. pp 146-149. 2008.

6. Ghetas, A. M., G. E. Thaxton, C. Breedlove, V. L. v. Santen, and H. Toro. Effects of Adaptation of Infectious Bronchitis Virus Arkansas Attenuated Vaccine to Embryonic Kidney Cells. Avian Dis. 59:106-113. 2015.

7. Jackwood, M. W., D. A. Hilt, C. W. Lee, H. M. Kwon, S. A. Callison, K. M. Moore, H. Moscoso, H. Sellers, and S. Thayer. Data from 11 years of molecular typing infectious bronchitis virus field isolates. Avian Dis. 49:614-618. 2005.

8. Jackwood, M. W., D. A. Hilt, A. W. McCall, C. N. Polizzi, E. T. McKinley, and S. M. Williams. Infectious bronchitis virus field vaccination coverage and persistence of Arkansas-type viruses in commercial broilers. Avian Dis. 53:175-183. 2009.

9. McKinley, E. T., D. A. Hilt, and M. W. Jackwood. Avian coronavirus infectious bronchitis attenuated live vaccines undergo selection of subpopulations and mutations following vaccination. Vaccine 26:1274-1284. 2008.

10. Ndegwa, E. N., K. S. Joiner, H. Toro, F. W. van Ginkel, and V. L. van Santen. The proportion of specific viral subpopulations in attenuated ArkDPI infectious bronchitis vaccines influences vaccination outcome. Avian Dis. 56:642-653. 2012.

11. Ndegwa, E. N., H. Toro, and V. van Santen. Comparison of vaccine subpopulation selection, viral loads, vaccine virus persistence in trachea and cloaca, and mucosal antibody responses after vaccination with two different Arkansas Delmarva Poultry Industry-derived infectious bronchitis virus vaccines Avian Dis 58:102-110. 2014.

12. Nix, W. A., D. S. Troeber, B. F. Kingham, C. L. Keeler, Jr., and J. Gelb, Jr. Emergence of subtype strains of the Arkansas serotype of infectious bronchitis virus in Delmarva broiler chickens. Avian Dis. 44:568-581. 2000.

13. Toro, H., J. W. Jackwood, and V. L. van Santen. Genetic diversity and selection regulates evolution of infectious bronchitis virus Avian Dis. 56:449-455. 2012.

14. Toro, H., D. Pennington, R. A. Gallardo, V. L. van Santen, F. W. van Ginkel, J. F. Zhang, and K. S. Joiner. Infectious bronchitis virus subpopulations in vaccinated chickens after challenge Avian Dis. 56:501-508. 2012.

15. Toro, H., V. L. van Santen, L. Li, S. B. Lockaby, E. van Santen, and F. J. Hoerr. Epidemiological and experimental evidence for immunodeficiency affecting avian infectious bronchitis. Avian Pathol. 35:1-10. 2006.

16. Toro, H., J. F. Zhang, R. A. Gallardo, V. L. v. Santen, F. W. v. Ginkel, K. S. Joiner, and C. Breedlove. S1 of Distinct IBV Population Expressed from Recombinant Adenovirus Confers Protection Against Challenge. Avian Dis 58:211-215. 2014.

17. van Ginkel, F. W., V. L. van Santen, S. L. Gulley, and H. Toro. Infectious bronchitis virus in the chicken Harderian gland and lachrymal fluid: viral load, infectivity, immune cell responses, and effects of viral immunodeficiency. Avian Dis. 52:608-617. 2008.

18. van Santen, V. L., and H. Toro. Rapid selection in chickens of subpopulations within ArkDPI-derived infectious bronchitis virus vaccines. Avian Pathol. 37:293-306. 2008.

19. Villegas, P. Titration of biological suspensions. In: A laboratory manual for the isolation, identification and characterization of avian pathogens. L. Dufour-Zavala, D. E. Swayne, J. R. Glisson, J. E. Pearson, W. M. Reed, M. W. Jackwood, and P. R. Woolcock, eds. American Association of Avian Pathologists, Athens, Ga. pp 217-221. 2008.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. A vaccine comprising a passaged attenuated population of IBV strain ArkDPI and a suitable carrier or excipient, wherein the passaged attenuated population of IBV strain ArkDPI exhibits at least about 95% homogeneity at one or more amino acid positions in the S1 polypeptide including Arg at amino acid position 323 of the S1 polypeptide.

2. The vaccine of claim 1, wherein the passaged attenuated population of IBV strain ArkDPI further exhibits at least about 95% homogeneity with respect to Ser at amino acid position 213 of the S1 polypeptide.

3. The vaccine of claim 1, wherein the passaged attenuated population of IBV strain ArkDPI further exhibits at least about 95% homogeneity with respect to Ser at amino acid position 213 of the S1 polypeptide; Arg at amino acid position 386 of the Spolypeptide, Gln at amino acid position 398 of the S1 polypeptide, and His at amino acid position 399 of the S1 polypeptide.

4. The vaccine of claim 3, wherein the passaged attenuated population of IBV strain ArkDPI further exhibits homogeneity at one or more amino acid positions in a polypeptide selected from NSP2, NSP3, NSP14, and S2.

5. A method for vaccinating a subject against infection by IBV, the method comprising administering to the subject the vaccine of claim 1.

6. The method of claim 5, wherein the vaccine comprises an effective amount of the passaged attenuated population of IBV for inducing an immune response against S1 polypeptide.

7. The method of claim 6, wherein the immune response is an antibody reponse.

8. The method of claim 5, wherein the vaccine is administered in a prime/boost regimen.

9. The vaccine of claim 1, wherein the passaged attenuated population of IBV strain ArkDPI further exhibits at least about 95% homogeneity with respect to Arg at amino acid position 386 of the S1 polypeptide, Gln at amino acid position 398 of the S1 polypeptide, His at amino acid position 399 of the S1 polypeptide, or any combination thereof.

* * * * *